US007670812B2

(12) United States Patent
Kajiura et al.

(10) Patent No.: US 7,670,812 B2
(45) Date of Patent: Mar. 2, 2010

(54) METHOD OF PRODUCING GLYCOGEN

(75) Inventors: Hideki Kajiura, Higashiosaka (JP); Hiroki Takata, Kobe (JP); Takeshi Takaha, Kobe (JP); Takashi Kuriki, Suita (JP)

(73) Assignee: Ezaki Glico Co., Ltd., Osaka (JP)

( * ) Notice: Subject to any disclaimer, the term of this patent is extended or adjusted under 35 U.S.C. 154(b) by 66 days.

(21) Appl. No.: 11/575,794

(22) PCT Filed: Sep. 28, 2005

(86) PCT No.: PCT/JP2005/017900

§ 371 (c)(1),
(2), (4) Date: Nov. 14, 2007

(87) PCT Pub. No.: WO2006/035848

PCT Pub. Date: Apr. 6, 2006

(65) Prior Publication Data
US 2008/0131941 A1 Jun. 5, 2008

(30) Foreign Application Priority Data
Sep. 30, 2004 (JP) ............................. 2004-289337

(51) Int. Cl.
*C12P 19/04* (2006.01)
*C12N 9/00* (2006.01)
*C12N 9/10* (2006.01)
*C12N 1/20* (2006.01)
*C12N 15/00* (2006.01)
*C07H 21/04* (2006.01)

(52) U.S. Cl. .................. 435/101; 435/183; 435/193; 435/252.3; 435/320.1; 536/23.2

(58) Field of Classification Search .................. None
See application file for complete search history.

(56) References Cited

FOREIGN PATENT DOCUMENTS

| JP | 57-138387 | 8/1982 |
|---|---|---|
| WO | 00/58445 | 10/2000 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
International Search Report for corresponding Application No. PCT/JP2005/017900 mailed Dec. 20, 2005.
Hiroki Takata et al.; "Properties and Application of Enzymes for Bacterial Glycogen Biosynthesis and Degradation"; Journal of Applied Glycoscience, 2004, vol. 51, pp. 55 to 61; Full text, particularly p. 57, left column, paragraph No. [0003].
Hiroki Takata et al.; "Properties of Branching Enzyme from Hyperthermophilic Bacterium, *Aquifex aeolicus*, and Its Potential for Production of Highly-branched Cyclic Dextrin"; Journal of Applied Glycoscience, 2003, vol. 50, pp. 15-20; Full text.

Kazuo Matsuda et al.; "Role Branching Enzyme in Glycogen Biosynthesis in *Neuroapora crassa*"; J. Jpan. Soc. Starch Sci., 1983, vol. 30(2), pp. 212-222; Full text.
J.S. Hawker et al.; "Interaction of Spinach Leaf Adenosine Diphosphate Glucose α-1, 4-Glucan α-1, 4-Glucan-6-Glycosyl Transferase in Synthesis of Branched α-Glucan", Archives of Biochemistry and Biophysics, 1974, vol. 160, pp. 530-551; Full text, particularly p. 537, left column, paragraph No. [0002] from the bottom to p. 539, left column, line 20.
Charles Boyer et al.; "Biosynthesis of Bacterial Glycogen Purifixation and Properties of the *Escherichia coli* B α-1, 4-Glucan: α-1, 4-Glucan 6-Glycosyltransferase"; Biochemistry, 1977, vol. 16 (16), pp. 3693-3699; Full text, particularly, p. 3696, right column, 16 lines from the bottom to p. 3697, left column, line 19.
Elaine Rumbak et al.; "Characterization of the Butyrivibrio fibrisolvens glgB Gene, with Encodes a Glycoge-Branching Enzyme with Starch-Clearing Activity"; Journal of Bacteriology, 1991, vol. 173 (21), pp. 6732 to 6741.
Nelly Lavintiman et al.; "The α-glucan-branching glycosyltransferase of sweet corn"; Biochim. Biophys. Acta, 1964, vol. 89, pp. 193-196.
Hiroki Takata et al.; "Properties and Active Center of the Thermostable Branching Enzyme from *Bacillus stearothermophilus*", Applied and Environmental Microbiology, Sep. 1994, pp. 3096-3104.
Takashi Kuriki et al.; "Review—The Concept of the α-Amylase Family: Structural Similarity and Common Catalytic Mechanism", Journal of Bioscience and Bioengineering, vol. 87, No. 5, 1999, pp. 557-565.
Takashi Kuriki et al.; "Analysis of the Active Center of Branching Enzyme II from Maize Endosperm", Journal of Protein Chemistry, vol. 15, No. 3, 1996, pp. 305-313.
Kim Binderup et al.; "Glutamate-459 Is Important for *Escherichia coli* Branching Enzyme Activity", Biochemistry, vol. 37, No. 25, 1998, pp. 9033-9037.
Rene Mikkelsen et al.; "Tyrosine Residue 300 Is Important for Activity and Stability of Branching Enzyme from *Escherichia coli*", Archives of Biochemistry and Biophysics, vol. 385, No. 2, Jan. 15, 2001, pp. 372-377.
Mari L. Shinohara et al.; "A novel thermostable braching enzyme from an extremely thermophilic bacterial species, *Thodothermus obamensis*", Appl. Microbiol Biotechnol, 57, 2001, pp. 653-659.

(Continued)

*Primary Examiner*—Christian L Fronda
(74) *Attorney, Agent, or Firm*—Renner, Otto, Boisselle & Sklar, LLP

(57) ABSTRACT

A method of producing glycogen comprising a step of: allowing a branching enzyme having the ability to synthesize glycogen to act on a substrate in a solution to produce a glycogen, wherein the substrate is an α-glucan being linked mainly with α-1,4-glucosidic bonds and having a degree of polymerization of 4 or more, and the number-average molecular weight of saccharides in the solution before initiation of the reaction is more than 180 but not more than 150,000. (The branching enzyme activity of the branching enzyme)/(the molecular-weight-decreasing activity of the branching enzyme) can be 500 or less. The branching enzyme can be a thermostable branching enzyme.

21 Claims, 11 Drawing Sheets

OTHER PUBLICATIONS

Ida Hilden et al.; "Characterization and crystallization of an active N-terminally truncated form of the *Escherichia coil* glycogen branching enzyme", Eur. J. Biochem, 267, Feb. 2000, pp. 2150-2155.

"Handbook of Amylases and Related Enzymes—*Their Sources, Isolation Methods, Properties and Applications*", Edited by The Amylase Research Society of Japan, Oxford, Pergamon Press, pp. 143-154, (1988).

Hiroki Takata; "Confirmation of the Solubility of the Product Obtained from 1000Kda Amylose by *Aquifex aeolicus* Be", Experimental Report, Apr. 12, 2006, Ezaki Glico Co., Ltd., Biochemical Research Laboratory and translation thereof.

* cited by examiner

A: Intermolecular branching reaction

B: Cyclization reaction

C: Intramolecular branching reaction

○: Glucosyl residue
⌀: Reducing terminus
—: $\alpha$-1,4-glucosidic bond
|: $\alpha$-1,6-glucosidic bond
▽: Action point of BE
⊚: Glucosyl residue serving as acceptor Some glucosyl residues are omitted and shown as a broken line.

Amylose

Glycogen

METHOD OF PRODUCING GLYCOGEN

TECHNICAL FIELD

The present invention relates to a method of producing a highly branched α-glucan of high molecular weight, particularly a glycogen.

BACKGROUND ART

α-Glucan is an α-D-glucose polymer. Various forms of α-glucan occur in nature. Among α-glucans, typical examples are glycogen and starch. However, glycogen and starch are significantly different from each other in structural and physical features.

Glycogen is the major storage polysaccharide in animals, fungi, yeasts and bacteria. Glycogen is water-soluble and forms a milky white solution. The molecular structure of glycogen in animals is well studied. Native glycogen is a homoglucan wherein a saccharide chain of grape sugars (glucoses) bonded linearly via α-1,4-glucosidic bond is branched via α-1,6-glucosidic bonds and the resulting branch is further branched to form a network structure. Native glycogen is composed of α-1,4-glucoside-linked chains having an average degree of polymerization of about 10 to about 14 and binding via α-1,6-glucosidic bonds. The molecular weight of native glycogen is described variously, and is estimated to be about $10^5$ to about $10^8$. Native glycogen occurs as a particle having a molecular weight of about $10^7$ (β-particle) or as a larger particle (α-particle) formed by aggregation of β-particles. It is considered that the structure of glycogen in bacteria is similar to the structure of glycogen in animals. A glucan similar in structure to glycogen occurs in certain plants (for example, sweet corn) and is called vegetable glycogen (phytoglycogen).

Starch is the major storage polysaccharide in plants and occurs as a water-insoluble particle. This particle contains two different polysaccharides. The two polysaccharides are amylose and amylopectin. Amylose is composed of substantially linear D-glucose units linked with α-1,4 bonds. Amylopectin is a branched polymer considered to have a cluster structure. Each cluster unit is composed of α-1,4-linked glucosyl chains having an average degree of polymerization of about 12 to about 24 and binding to one another via α-1,6-glucosidic bonds. The cluster unit is further linked with a longer α-1,4-linked glucosyl chain having an average degree of polymerization of about 30 to about 100. The average chain length of the whole amylopectin is about 18 to about 25 in terms of a degree of polymerization. Starch amylopectin, similar to glycogen, is glucan bound via α-1,4-glucosidic bonds and α-1,6-glucosidic bonds, but glycogen is branched at a higher degree than amylopectin.

Recently, glycogen was proven to have an immunostimulating effect. Accordingly, glycogen can be expected for use as an immunostimulant, health food material and the like. In addition, the application of glycogen as a cosmetic material, a food material (flavoring material), and other industrial materials can be expected. Glycogen is utilized in various industrial fields. Applications of glycogen include, for example, a therapeutic agent for microbial infections, a humectant (for example, a cosmetic effective for improving the moisture retention of skin, a cosmetic for prevention of roughening of lips), a complex seasoning (for example, a complex seasoning having the taste of the eye of a scallop), an antitumor agent, an accelerator for formation of fermented milk, a colloid particle aggregate, a substance improving abrasion resistance of a hair surface, which influences ease in combing and luster of hair, a cellular stimulant (an epidermal cell stimulant, a fibroblast growth stimulant, and the like), an ATP production accelerator, an agent for ameliorating skin aging symptoms such as wrinkles, an agent for ameliorating skin roughening, a surface treatment agent for fluorescent particle, and a substrate in the synthesis of cyclic tetrasaccharide (CTS; cyclo{→6}-α-D-glcp-(1→3)-α-D-glcp-(1→6)-α-D-glcp-(1→3)-α-D-glcp-(1→}). Glycogen can be used in external preparations for skin (for example, skin lotion, emulsion, cream, essence, hair-growth medicine, hair growth tonic, mask, lip stick, lip cream, makeup base lotion, makeup base cream, foundation, eye color, cheek color, shampoo, rinse, hair liquid, hair tonic, permanent wave agent, hair color, treatment, bath agent, hand cream, leg cream, neck cream, body lotion, and the like), in a solution for eyes or the like.

Glycogen derived from mussels (moule) and vegetable glycogen (phytoglycogen) derived from sweet corn are marketed but is expensive and used mainly as a humectant in cosmetics. As a reagent, glycogen derived from various kinds of shellfish or animal livers is also marketed but extremely expensive and hardly industrially applicable.

Accordingly, it is desired to provide glycogen inexpensively in a large amount.

A branching enzyme (systematic name: 1,4-α-D-glucan: 1,4-α-D-glucan 6-α-D-(1,4-α-D-glucano)-transferase, EC2.4.1.18, which is also referred to in this specification as BE) is an enzyme which cleaves α-1,4-glucosidic bonds and transfers the bond to an OH group at the 6-position of another glucosyl residue to form α-1,6-glucosidic bond. BE is distributed widely in animals, plants, mould fungi, yeasts and bacteria and catalyzes synthesis of a branched bond of glycogen or starch.

The catalytic action of potato-derived BE was examined in detail in the 1970's, and BE has been proven to catalyze an intermolecular branching reaction (FIG. 1A). It was proven in the late 1990's that BE catalyzes a cyclization reaction (FIG. 1B). By proving this cyclization reaction, it was logically estimated that an intramolecular branching reaction (FIG. 1C) is also catalyzed by BE. This is because from the microscopic viewpoint of cleavage of α-1,4-glucosidic bonds, transfer of the bond to an OH group at the 6-position of another glucosyl residue, and formation of α-1,6-glucosidic bond, these 3 reactions can be said to be identical. BE is regarded as one member of the glycoside hydrolase 13 family (α-amylase family) and considered to catalyze, at a single active center, cleavage of α-1,4-glucosidic bonds and transfer of the bond to an OH group at the 6-position by basically the same mechanism as that of α-amylase.

It is known that glycogen similar in structure and properties to native glycogen can be synthesized by allowing BE, together with another enzyme, α-glucan phosphorylase, to act on glucose-1-phosphate and oligosaccharide, or by allowing BE, together with glycogen synthase (or starch synthase), to act on UDP-glucose (or ADP-glucose). However, α-glucan phosphorylase is marketed as a reagent, but is extremely expensive. Further, acquisition of glycogen synthase and starch synthase is difficult. Glucose-1-phosphate, UDP-glucose, and ADP-glucose are extremely expensive. Accordingly, the problem of providing glycogen inexpensively in a large amount could not be solved by this method.

A macromolecule such as glucan is generally not a uniform molecule but a mixture of molecules having various sizes, and thus its molecular weight is evaluated in terms of a number-average molecular weight (Mn) or a weight-average molecular weight (Mw). The Mn is determined by dividing the total mass of the system by the number of molecules contained in the system. That is, the Mn is an average by number fraction. On the other hand, the Mw is an average by weight fraction. Given a completely homogeneous material, Mw=Mn, but a macromolecule generally has a molecular weight distribution, and therefore Mw>Mn. It follows that as Mw/Mn exceeds 1 and becomes higher, a degree of heterogeneity of the molecular weight becomes higher (that is, the molecular weight distribution is broader).

Amylose synthesized using an enzyme (for example, enzymatically synthesized amylose manufactured by Ajinoki Co., Ltd.) is known to have a narrow molecular weight distribution (the Mw/Mn <1.2 in Nonpatent Document 4; and the Mw/Mn=1.005 to 1.006 in Fujii, K. et al. (2003) *Biocatalysis and Biotransformation*, Vol. 21, pp. 167-172). On the other hand, amylose extracted from nature has a relatively broader molecular weight distribution, and the Mw/Mn is about 2 to about 5 (described in pp. 347-429 in Carbohydrates in food, edited by Eliasson, A.-C., Marcel Dekker, Inc., New York (1996); a degree of polymerization DP (number-average DPn, weight-average DPw) in Table 15 in Hizukuri, S., Starch: analytical aspects. By multiplying these DP by 162, the respective average molecular weights are given).

The Mn can be determined by evaluating the number of molecules. That is, the Mn of amylose or the like can be determined by measuring the number of reducing termini. The number of reducing termini can be determined, for example, by a modified Park-Johnson method described in Nonpatent Document 7. The Mn can also be determined for example by gel filtration chromatography (MALLS method) of using a differential refractometer in combination with a multi-angle laser-light scattering detector as described in Nonpatent Document 8. The Mw can be determined by the MALLS method described in Nonpatent Document 8.

In this specification, the molecular weight of a substrate is evaluated mainly in terms of the number-average molecular weight (Mn), while the molecular weight of produced glucan is evaluated mainly in terms of weight-average molecular weight (Mw). This is because when the product undergoes the cyclization reaction shown in FIG. 1B, Mn cannot be correctly evaluated by the method of evaluating the number of reducing termini, also because when the molecular weight of a very large molecule is evaluated, the number of reducing termini is relatively low, thus making accurate measurement of Mn difficult, and further, because the method of evaluating Mn by the MALLS method is based on the premise that fractionation by gel filtration is complete, so when the fractionation is incomplete, accurate evaluation of Mn is not feasible.

There are examples where BE is allowed to act on amylopectin or starch to give high molecular weight α-glucan. There are a large number of examples where BE alone is allowed to act on α-glucan (for example, amylose). However, there is no example where BE is allowed to act on amylose to give high molecular weight α-glucan having a molecular weight of about 1,000,000 or more. High molecular weight α-glucan obtained by allowing BE to act on amylopectin is considered to have increased branches on a fundamental structure of amylopectin, as shown in Nonpatent Document 17, and it can be said that glycogen (having a globular structure) was not synthesized. For example, Nonpatent Documents 1 and 2 describe that *Neurospora crassa*-derived BE is allowed to act on amylopectin or amylose thereby converting them into a highly branched glycogen-like molecule consisting of unit chains of 6-glucose units. However, the term "glycogen-like" merely means that a degree of coloration of the molecule by iodine is similar to that of glycogen. Amylose used therein as the substrate has number-average degrees of polymerization of 15, 22 or 130, indicating an Mn of about 2430, about 3600 and about 21000, respectively. Particularly, Nonpatent Document 2 describes that *N. crassa*-derived BE can act on short-chain amylose having an average degree of polymerization of 15 or 22, and the minimum degree of polymerization in amylose on which the plant-derived BE can act is 30 to 40 or more. Nonpatent Document 2 also describes that *N. crassa*-derived BE was suggested to act on a glucose chain of 12 residues or more thereby effecting transfer reaction of hexasaccharide as the minimum unit. As it can be seen from FIGS. 1 and 2 in Nonpatent Document 1 and FIGS. 3 and 4 in Nonpatent Document 2, when *N. crassa*-derived BE was allowed to act on amylopectin and amylose, the molecular weights of such substrates did not change. Further, FIGS. 4 and 5 in Nonpatent Document 1 and FIGS. 5 and 6 in Nonpatent Document 2 show that molecules slightly greater and slightly smaller than the substrate molecule are obtained, and a significantly high-molecular weight product was not observed.

For example, Nonpatent Document 3 describes that when maize BE I was allowed to act on amylose having an average chain length of greater than 300, a delay of the elution time of the product in gel filtration occurred, and this delay is due to a change in shape, but not to a change in molecular weight.

For example, Nonpatent Document 4 describes that the molecular weight of an amylopectin-like molecule obtained by allowing BE (particularly, Q enzyme) to act on amylose is decreased as the reaction time is increased.

For example, Nonpatent Document 5 describes that when potato-derived BE (Q enzyme) is allowed to act on amylose having an Mw of 67600, a reaction product having an Mw of 33500 can be obtained.

For example, Nonpatent Document 6 describes that when potato-derived BE is allowed to act on amylose having an Mn of 200,000, glucan having an Mw of 22,000 can be obtained.

For example, Nonpatent Document 7 describes that when *Bacillus stearothrmophilus*-derived BE is allowed to act on enzymatically synthesized amylose having an Mw of 302,000, a cyclization reaction is occurred to reduce the molecular weight of them. It is noted that the enzymatically synthesized amylose used as the substrate is known to have a narrow molecular weight distribution. For example, an enzymatically synthesized amylose's Mw/Mn <1.2 according to Nonpatent Document 4, and an enzymatically synthesized amylose's Mw/Mn=1.005 to 1.006, according to Fujii, K. et al. (2003) *Biocatalysis and Biotransformation*, Vol. 21, pp. 167-172. An enzymatically synthesized amylose's Mw/Mn <1.1, according to a pamphlet of a manufacturer Ajinoki Co., Ltd. Accordingly, the approximate Mn of the enzymatically synthesized amylose used in this document is about 252,000 to 302,000. Therefore, the Mn of the enzymatically synthesized amylose can be approximately estimated by dividing Mw by 1.1.

For example, Nonpatent Document 8 describes that when *Aquifex aeolicus*-derived BE is allowed to act on α-glucan, cyclized glucan can be obtained. This means that glucan is degraded into lower-molecular-weight products, as is evident from FIG. 1B.

For example, Nonpatent Document 9 describes that when *Bacillus cereus*-derived BE was allowed to act on enzymatically synthesized amylose of various sizes, glucan of almost the same size was obtained from all enzymatically synthesized amylose (FIG. 5.8). Further, from FIG. 5.9 in this document, it is evident that no component with a molecular weight of greater than about 1,000,000 was detected. Further, from a reaction model in FIG. 5.13 in this document, formation of highly branched and high molecular weight α-glucan cannot be expected. As is evident from FIG. 1, both larger and smaller molecules than the original molecule are generated in the intermolecular branching reaction by BE (FIG. 1A); a molecule smaller than the original molecule is generated in the cyclization reaction (FIG. 1B); and in the intramolecular branching reaction (FIG. 1C), the molecular weight is not changed before and after there action. Because the mechanisms of these reactions are the same, it cannot be expected that the 3 reactions occur at significantly different frequencies. Actually, the result in FIG. 5.8 in Nonpatent Document 9 reveals that all 3 reactions are catalyzed with some difference depending on the molecular weight of the substrate, resulting in formation of glucan of the same size from amylose of any size. In order to obtain high molecular weight glucan having a molecular weight of 1,000,000 or more from amylose, the intermolecular branching reaction of (A) is needed to be catalyzed at an overwhelmingly higher frequency, and among the resulting molecules, greater molecules are needed to undergo the reaction in the direction of further continuing polymerization. This cannot be expected from the conventional catalytic mechanism of BE, and no results obtained which suggest this.

Patent Document 2 describes a method of producing glucan having a degree of polymerization in the range of 50 to 5000 having an internal branched cyclic structural moiety and an external branched structural moiety, which comprises allowing BE (particularly, a branching enzyme) to act on amylose, partially degraded starch, debranched starch, amylose enzymatically synthesized with phosphorylase, maltooligosaccharide, and the like. In this method, the substrate is cyclized and formed by BE into a lower-molecular-weight molecule thereby producing cyclic glucan having a degree of polymerization of 50 to 5000 and a maximum degree of polymerization of 10,000. In this method, the product is obtained by forming the substrate into a lower-molecular-weight molecule, and thus high molecular weight amylose is used as the substrate. This is evident from paragraph 0066 describing that amylose having a degree of polymerization of about 400 or more can be preferably used. The molecular weight of amylose having a degree of polymerization of 400 is about 65,000, and whether or not high molecular weight α-glucan can be obtained using low molecular weight amylose as the substrate is not evident from this patent publication.

As described above, so far, it is believed that when BE is allowed to act on amylose, the amylose is converted into a lower-molecular-weight molecule, or even if the molecular weight of a certain molecule may be increased, there are few molecules undergoing polymerization to increase the molecular weight, and the molecular weight of the products are hardly changed.

Further, it is reported that α-glucan obtained by allowing BE to act on amylose is different from glycogen in that the α-glucan is easily degraded with pullulanase (Nonpatent Documents 10 and 16). There is also a document describing that "glycogen" was obtained by allowing BE to act on amylose (for example, Nonpatent Document 18 (Walker et al., *Eur. J. Biochem.* (1971) Vol. 20, pp. 14-21)), but in this document, the molecular weight of the resulting glucan is not measured, nor is digestibility analyzed.

Further, there are many examples wherein BE is allowed to act on amylose in order to examine the properties of the enzyme (for example, Patent Document 3 and Nonpatent Documents 11 to 12). In none of these examples, however, is the molecular weight of the reaction product measured.

It is known that BE (particularly plant-derived BE) hardly acts on short-chain amylose. For example, Nonpatent Document 13 describes that BE hardly acts on amylose having a degree of polymerization of 40 or less (molecular weight of about 6480). This is possibly because BE requires substrate amylose to have a certain higher order structure, but amylose not having a certain length can not have such higher order structure (Nonpatent Document 14). Further, it is considered that such higher order structure is related to temperature, and when the temperature is high, amylose cannot have such higher order structure.

Bacterium-derived BE seems to act on a short substrate (Nonpatent Document 15), but its action is known to be weak (Nonpatent Document 9, FIG. 4.5).

From the foregoing, it cannot be expected that highly branched and high molecular weight glucan having a molecular weight of 1,000,000 or more can be synthesized from amylose as the substrate by BE, and still more, it cannot be expected that the digestibility of the high molecular weight glucan with pullulanase and α-amylase is low. Further, because of the low activity thereof on enzymatically synthesized amyloses having Mns of 4800 and 9,300 (about 7% and 12% activity as compared the maximum activity thereof when enzymatically synthesized amylose having an Mn 270,000 is used as a substrate. FIG. 4.5 in Nonpatent Document 9), advantages of using amylose having an Mn of 8,000 or less (particularly an Mn of 4,000 or less) as a substrate have not been contemplated.

Further, in the conventional methods of producing glycogen, there is also the problem that significantly high expenditure is necessary for obtaining high-purity glycogen because the contents of electrolytes and monosaccharides are high unless the product is highly purified. For example, in the method of producing glycogen by adding BE to sucrose phosphorylase and α-glucan phosphorylase, addition of about 10 mM phosphoric acid to the reaction solution is needed, and the resulting reaction product contains a large amount of fructose and a small amount of phosphoric acid (sucrose+phosphoric acid+oligosaccharides→α-glucan+fructose+phosphoric acid). In the method wherein GP is combined with BE, the product contains a larger amount of electrolyte (glucose-1-phosphate+oligosaccharide→α-glucan+phosphoric acid). This also applies to the method wherein glycogen synthase (GS) is combined with BE (ADP-glucose+oligosaccharides→α-glucan+ADP).

Even if glycogen is extracted from a natural product, the glycogen is contaminated with various substances such as proteins, lipids and other carbohydrates in addition to electrolytes, and thus there is a problem of significantly high expenditure in obtaining high-purity glycogen.

Patent Document 1: Japanese Laid-open Publication No. 2000-316581
Patent Document 2: Japanese Patent No. 3107358, claim 1, column 0066
Patent Document 3: Japanese Patent National Phase PCT Laid-Open Publication No. 2002-539822
Nonpatent Document 1: Matsumoto et al., J. Biochem, Vol. 107, 118-122 (1990) (FIG. 2)
Nonpatent Document 2: Matsumoto and Matsuda, "Denpun Kagaku" (Starch Science), Vol. 30, pp. 212-222 (1983) (FIGS. 3 & 4)
Nonpatent Document 3: Boyer et al., *Starch/staerke* 34 Nr. 3, S. 81-85 (1982) (Table 1, FIG. 2 and FIG. 3)
Nonpatent Document 4: Kitamura, *Polymeric Materials Encyclopedia*, Vol. 10, pp. 7915-7922 (Table 2)
Nonpatent Document 5: Praznik et al., *Carbohydrate Research*, 227 (1992) pp. 171-182
Nonpatent Document 6: Griffin and Victor, *Biochemistry* Vol. 7, No. 9, September 1968

Nonpatent Document 7: Takata, H. et al., Cyclization reaction catalyzed by branching enzyme. *J. Bacteriol.*, 1996. 178: pp. 1600-1606

Nonpatent Document 8: Takata, H. et al., *J. Appl. Glycosci.*, 2003. 50: pp. 15-20

Nonpatent Document 9: Hiroki Takata Thesis For A Doctorate (Kyoto University, JP) 1997 (Studies on Enzymes Involved in Glycogen Metabolism of *Bacillus* Species)

Nonpatent Document 10: Charles Boyer and Jack Preiss, *Biochemistry* 1977, Vol. 16, No. 16, pp. 3693-3699

Nonpatent Document 11: Shinohara, M. L. et al., *Appl Microbiol Biotechnol*, 2001. 57(5-6): pp. 653-9

Nonpatent Document 12: Takata, H. et al., *Appl. Environ. Microbiol.*, 1994. 60: pp. 3096-3104

Nonpatent Document 13: Borovsky, D., Smith, E. E. and Whelan, W. J. (1976) *Eur. J. Biochem.* 62, 307-312

Nonpatent Document 14: Borovsky, D., Smith, E. E. and Whelan, W. J. (1975) *FEBS Lett.* 54, 201-205

Nonpatent Document 15: Okada et al., "Denpun Kagaku" (Starch Science), Vol. 30, pp. 223-230 (1983)

Nonpatent Document 16: Kitahata, S, and Okada, S. (1988) in Handbook of amylase and related enzymes. Their sources, isolation methods, properties and applications. (The Amylase Research Society of Japan ed), pp. 143-154, Pergamon Press, Oxford Nonpatent Document 17: Kawabata et al. (2002) *J. Appl. Glycosci.* Vol. 49, No. 3, 273-279

Nonpatent Document 18: Walker et al., *Eur. J. Biochem.* (1971) Vol. 20, pp. 14-21

DISCLOSURE OF THE INVENTION

Problems to be Solved by the Invention

The object of the present invention is to provide a production method of highly branched and high molecular weight α-glucan, particularly glycogen, in order to solve the aforementioned problems.

Means for Solving the Problems

In order to solve the aforementioned problems, the present inventors continued to intensively study and, as a result, finally found that BE having a ratio (the branching enzyme activity)/(the molecular-weight-decreasing activity) of 500 or less has the ability to synthesize glycogen, which resulted in completion of the present invention.

The production method of the present invention is a method of producing glycogen, which comprises a step of allowing a BE having the ability to synthesize glycogen to act on a substrate to produce a glycogen, wherein the substrate is an α-glucan being linked mainly with α-1,4-glucosidic bonds and having a degree of polymerization of 4 or more, and the number-average molecular weight (Mn) of saccharides in the solution before initiation of the reaction is more than 180 but not more than 150,000.

In one embodiment, (the branching enzyme activity of the branching enzyme)/(the molecular-weight-decreasing activity of the branching enzyme) can be 500 or less.

In one embodiment, the BE can be a thermostable branching enzyme.

In one embodiment, the BE can be derived from a thermophilic bacterium or mesophilic bacterium.

In one embodiment, the BE can be derived from a bacterium belonging to a genus selected from the group consisting of the genera *Aquifex*, *Rhodothermus*, *Bacillus*, *Thermosynechococcus* and *Escherichia*.

In one embodiment, the BE can be derived from a bacterium selected from the group consisting of *Aquifex aeolicus*, *Aquifex pyrophilus*, *Rhodothermus obamensis*, *Rhodothermus marinus*, *Bacillus stearothermophilus*, *Bacillus caldovelox*, *Bacillus thermocatenulatus*, *Bacillus caldolyticus*, *Bacillus flavothermus*, *Bacillus acidocaldarius*, *Bacillus caldotenax*, *Bacillus smithii*, *Thermosynechococcus elongatus* and *Escherichia coli*.

In one embodiment, the BE can be derived from a bacterium selected from the group consisting of *Aquifex aeolicus*, *Rhodothermus obamensis*, *Bacillus stearothermophilus*, *Bacillus caldovelox*, *Bacillus thermocatenulatus*, *Bacillus caldolyticus* and *Escherichia coli*.

In one embodiment, the optimum reaction temperature of the BE can be not less than 45° C. and no more than 90° C.

In one embodiment, the substrate can be debranched starch, debranched dextrin, or enzymatically synthesized amylose.

In one embodiment, the Mn of the saccharides in the solution before initiation of the reaction can be greater than 180 and less than 4,000.

In one embodiment, the Mn of the saccharides in the solution before initiation of the reaction can be 4,000 or more and less than 8,000, and the amount of the BE used and the reaction time can be adjusted such that the product of the amount of the BE used and the reaction time becomes 25,000 U·hour/g substrate or more.

In one embodiment, the Mn of the saccharides in the solution before initiation of the reaction can be 8,000 or more and less than 100,000, and the amount of the BE used and the reaction time can be adjusted such that the product of the amount of the BE used and the reaction time becomes 40,000 U·hour/g substrate or more.

In one embodiment, the Mn of the saccharides in the solution before initiation of the reaction can be 100,000 or more and 150,000 or less, and the amount of the BE used and the reaction time can be adjusted such that the product of the amount of the BE used and the reaction time becomes 150,000 U·hour/g substrate or more.

In one embodiment, the method of the present invention can further comprise a step of allowing 4-α-glucanotransferase to act on α-glucan having an Mn of greater than 180 and less than 1,500 to produce the substrate.

In one embodiment, the α-glucan having the Mn of greater than 180 and less than 1,500 can contain a maltooligosaccharide having a degree of polymerization of 4 to 7.

In one embodiment, the method of the present invention can further comprise a step of allowing a debranching enzyme to act on low-branched α-glucans having an Mn of 500 or more to produce the substrate.

In one embodiment, the method of the present invention uses neither α-glucan phosphorylase nor glycogen synthase.

In one embodiment, 4-α-glucanotransferase can be coexistent with the BE.

EFFECTS OF THE INVENTION

According to the present invention, glycogen can be produced inexpensively in a large amount.

The method of the present invention has an advantage that glycogen with very low content of electrolytes and monosaccharides can be obtained without high purification. Accordingly, there is the advantage that high-purity glycogen can be obtained at low cost.

BRIEF DESCRIPTION OF THE DRAWINGS

FIG. 1A is a drawing showing that BE catalyzes an intermolecular branching reaction. FIG. 1B is a drawing showing that BE catalyzes a cyclization reaction. FIG. 1C is a drawing showing that BE catalyzes an intramolecular branching reaction.

SEQUENCE LISTING FREE TEXT

Figure 1:
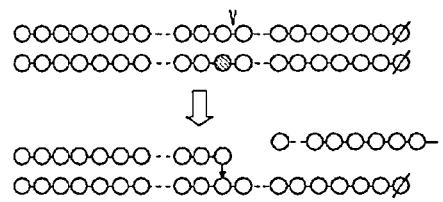
FIG. 1 is a drawing schematically showing various actions of BE.
Figure 1:
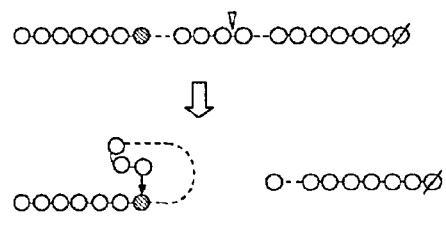
Figure 1:
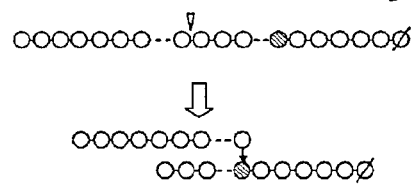

SEQ ID NO: 1: the base sequence encoding wild type BE from *Aquifex aeolicus* VF5;
SEQ ID NO: 2: the amino acid sequence of wild type BE from *Aquifex aeolicus* VF5;
SEQ ID NO: 3: the base sequence encoding wild type BE from *Rhodothermus obamensis* JCM9785;
SEQ ID NO: 4: the amino acid sequence of wild type BE from *Rhodothermus obamensis* JCM9785;
SEQ ID NO: 5: the base sequence encoding wild type BE from *Bacillus stearothermophilus* TRBE14;
SEQ ID NO: 6: the amino acid sequence of wild type BE from *Bacillus stearothermophilus* TRBE14;
SEQ ID NO: 7: the base sequence encoding wild type BE from *Bacillus stearothermophilus* 1503-4R var. 4;
SEQ ID NO: 8: the amino acid sequence of wild type BE from *Bacillus stearothermophilus* 1503-4R var. 4;
SEQ ID NO: 9: the base sequence encoding wild type BE from *Bacillus caldovelox* IFO15315;
SEQ ID NO: 10: the amino acid sequence of wild type BE from *Bacillus caldovelox* IFO15315;
SEQ ID NO: 11: the base sequence encoding wild type BE from *Bacillus thermocatenulatus*;
SEQ ID NO: 12: the amino acid sequence of wild type BE from *Bacillus thermocatenulatus*;
SEQ ID NO: 13: the base sequence encoding wild type BE from *Bacillus caldolyticus* IFO15313;
SEQ ID NO: 14: the amino acid sequence of wild type BE from *Bacillus caldolyticus* IFO15313;
SEQ ID NO: 15: the base sequence encoding wild type BE from *Thermosynechococcus elongatus* BP-1;
SEQ ID NO: 16: the amino acid sequence of wild type BE from *Thermosynechococcus elongatus* BP-1;
SEQ ID NO: 17: the base sequence encoding wild type BE from *Escherichia coli* W3110;
SEQ ID NO: 18: the amino acid sequence of wild type BE from *Escherichia coli* W3110;
SEQ ID NO: 19: the base sequence encoding TaqMalQ derived from *Thermus aquaticus*;
SEQ ID NO: 20: the amino acid sequence of TaqMalQ derived from *Thermus aquaticus*;
SEQ ID NO: 21: the sequence of primer ECBEN-NCO;
SEQ ID NO: 22: the sequence of primer ECBEC-HIN;
SEQ ID NO: 23: the sequence of primer ROBEN-ECO; and
SEQ ID NO: 24: the sequence of primer ROBEC-PST.

BEST MODE FOR CARRYING OUT THE INVENTION

Hereinafter, the present invention is described in detail.

The method of the present invention is a method of producing highly branched and high molecular weight α-glucan (that is, glycogen), which comprises a step of allowing a BE having the ability to synthesize glycogen to act on a substrate in a solution to produce glycogen, wherein the substrate is an α-glucan being linked mainly with α-1,4-glucosidic bonds and having a degree of polymerization of 4 or more, and the Mn of the saccharides in the solution before initiation of the reaction is more than about 180 but not more than about 150,000.

In this specification, "glycogen" refers to a saccharide containing D-glucoses as constituent units linked only via α-1,4-glucosidic bonds and α-1,6-glucosidic bonds, having a molecular weight of 1,000,000 Da or more, and when subjected to reaction with pullulanase in an amount of 50 U/g substrate under the conditions in Evaluation Example 1, gives a product having an Mw of 500,000 Da or more as determined by the MALLS method and when subjected to reaction with α-amylase in an amount of 300 U/g substrate under the conditions in Evaluation Example 2, gives a product having an Mw of 500,000 Da or more as determined by the MALLS method. When a certain saccharide upon subjection to reaction with pullulanase in an amount of 50 U/g substrate under the conditions in Evaluation Example 1 gives a product having a molecular weight Mw of 500,000 Da or more, the saccharide is referred as "being resistant to degradation by pullulanase." When a certain saccharide upon subjection to reaction with α-amylase in an amount of 300 U/g substrate under the conditions in Evaluation Example 2 gives a product having a molecular weight Mw of 500,000 Da or more, the saccharide is referred as "being resistant to degradation by α-amylase." Wherein, with respect to α-amylase activity, 1 U α-amylase activity refers to the amount of the enzyme which causes release of 1 mg maltose in 3 minutes from starch when the enzyme is reacted with the starch at pH 6.9 at 20° C. With respect to pullulanase activity, 1 U pullulanase activity refers to the amount of the enzyme necessary to generate reducing power corresponding to 1 μmol glucose in 1 minute in the early stage of the reaction when the enzyme is reacted on pullulan of a final concentration of 1% at pH 5.0 at 40° C.

(1. Branching Enzyme)

The "branching enzyme having an ability to synthesize glycogen" refers to a BE having the ability to synthesize glycogen, among BEs. Whether a certain BE has the ability to synthesize glycogen or not can be determined by a method known in the art. That is, whether a certain BE has the ability to synthesize glycogen can be determined for example by allowing the BE to act on amylose and thereafter examining whether high molecular weight α-glucan having a molecular weight of 1,000,000 Da or more is produced in the solution as well as by determining whether or not the produced high molecular weight α-glucan is resistant to degradation with pullulanase and degradation with α-amylase. Whether high molecular weight α-glucan is present in solution or not can be determined by an HPLC gel filtration analysis method using a differential refractometer in combination with a multi-angle laser-light scattering detector as detectors, as described in Nonpatent Document 8. Resistance to degradation with pullulanase can be determined according to the method in Evaluation Example 1. Resistance to degradation with α-amylase can be determined according to the method in Evaluation Example 2.

According to the inventors' study, a BE which among BEs, has (the branching enzyme activity)/(the molecular-weight-decreasing activity) of 500 or less has the ability to synthesize glycogen, while the BE which among BEs, has (the branching enzyme activity)/(the molecular-weight-decreasing activity) of more than 500 does not have the ability to synthesize glycogen.

The branching enzyme activity is an activity decreasing the absorbance of an amylose-iodine complex at 660 nm and is based on the ability of BE to cleave α-1,4-glucosidic bonds and transfer the bond to an OH group on the 6-position of another glucosyl residue thereby forming α-1,6-glucosidic bonds to reduce a linear-chain moiety of amylose.

Methods of measuring the branching enzyme activity of BE are known in the art and described, for example, in Nonpatent Document 8. The branching enzyme activity of a BE is measured for example as follows: First, 50 μL of enzyme solution is added to 50 μL of substrate solution (0.12% (w/v) amylose (Type III, manufactured by Sigma Chemical)) to initiate the reaction. The reaction is carried out at the optimum reaction temperature of the BE. After the BE is allowed to act for 10 minutes, 1 mL of 0.4 mM hydrochloric acid solution is added to terminate the reaction. Thereafter, 1 mL of iodine solution is added to, and mixed well, the reaction mixture which is then measured for its absorbance at 660 nm. As a control solution, the solution to which the 0.4 mM hydrochloric acid solution is added before addition of the enzyme solution is simultaneously prepared. The substrate solution is prepared by adding 200 μl of 50 mM potassium phosphate buffer (pH 7.5) to 100 μL of 1.2% (w/v) amylose type III solution (dissolved in dimethyl sulfoxide), then adding 700 μL distilled water thereto, and mixing the resulting mixture well. Provided that the pH of the buffer is adjusted to the optimum reaction pH of the BE used. The iodine solution is prepared by mixing 0.5 mL of 1 N hydrochloric acid with 0.125 mL of stock solution (2.6 wt % $I_2$, 26 wt % KI aqueous solution) and adjusting the volume of the mixture to 65 mL with distilled water. The BE activity of the enzyme solution is determined according to the following equation:

BE activity (unit (U)/mL)={[(absorbance of the control solution at 660 nm)−(absorbance of the sample solution at 660 nm)]/(absorbance of the control solution at 660 nm)}×100/10×20

The BE activity is used in principle as the measure of activity of BE in this specification. Accordingly, simple "activity" refers to "BE activity", and simple "unit" or "U" refers to "unit" or "U" measured in BE activity.

The molecular-weight-decreasing activity is an activity defined by the present inventors. The molecular-weight-decreasing activity is also referred to as amylopectin molecular-weight-decreasing activity. In this specification, 1 U molecular-weight-decreasing activity is defined as the amount of the enzyme which is necessary for decreasing the Mw of 1 g substrate (waxy cornstarch) to 400 kDa when the enzyme is reacted at the same temperature and pH as the measurement temperature and pH for BE activity (preferably, the optimum reaction temperature and optimum pH of the enzyme) for 16 hours.

The molecular-weight-decreasing activity is measured, for example, in the following manner. First, 100 μl distilled water is added to 50 mg waxy cornstarch (WCS, manufactured by Sanwa Cornstarch Co., Ltd.) and stirred sufficiently. Then, 900 μl dimethyl sulfoxide is added thereto, and stirred for 20 minutes in a boiling water bath. 8.9 ml distilled water is added thereto, and stirred well for an additional 10 minutes in a boiling water bath. 100 μl of 1 M Tris-HCl (pH 7.5) or 1 M phosphate buffer (pH 7.5) is added to this solution, stirred and used as a substrate solution. The pH of the buffer is adjusted to the pH for the measurement of BE activity.

The substrate solution is dispensed in a volume of 800 μL/tube. That is, each tube contains 4 mg WCS. Then, a suitably diluted BE solution is added in a suitable amount X μL per tube and a diluent is added in an amount of (200−X) μL per tube, to initiate the reaction. The reaction temperature is adjusted to the temperature for the measurement of BE activity. The diluent is 10 mM potassium phosphate buffer containing 0.05% Triton X-100 (pH is adjusted to the pH for the measurement of BE activity). When the reaction time reaches 16 hours, the pH of the reaction solution is reduced to 3 to 4 by addition of 1 N HCl, and the reaction solution is heated at 100° C. for 10 minutes to terminate the reaction. In the case of BE whose thermostability is sufficiently low, the reaction can be terminated by merely heating the reaction solution at 100° C. for 10 minutes.

After the reaction is terminated, the reaction solution is filtered through a 0.45-μm filter, and the Mw of the product contained in the reaction solution is measured. The amount of BE is adjusted such that the Mw falls within the range of 2500 kDa to 200 kDa. Measurement of Mw is carried out by a method described in "Method of Measurement of Weight-Average Molecular Weight (Mw) of Glucan Produced" below.

The logarithm of the calculated Mw (kDa) is plotted on the longitudinal axis (y-axis) while the amount of the enzyme used (μL) is plotted on the horizontal axis (x-axis), and the soft MS-Excel manufactured by Microsoft Corporation is used to prepare a power approximation curve. That is, the approximation curve is prepared with equation $y=cx^b$ (each of c and b is a constant). By assigning y=400 (kDa) to the equation obtained, the amount V1 (μL) of the enzyme necessary for decreasing the Mw of WCS (4 mg) as substrate to 400 kDa is calculated. By converting the amount V1 of the enzyme to the amount of the enzyme per 1 g substrate, the amount V2 (mL) of the enzyme (=(V1 μL/1000)×(1000 mg/4 mg) (mL)) necessary for 1 U molecular-weight-decreasing activity is calculated. The molecular-weight-decreasing activity E1 of the enzyme solution is a reciprocal of unit molecular-weight-decreasing activity (E1=1/V2) (U/mL).

The upper limit of (the BE activity)/(the molecular-weight-decreasing activity) is about 500, more preferably about 400, still more preferably about 300, further more preferably about 200, most preferably about 100. There is no particular lower limit of (the BE activity)/(the molecular-weight-decreasing activity). The lower limit can be about 1 or more, about 5 or more, or about 10 or more.

Figure 11A:
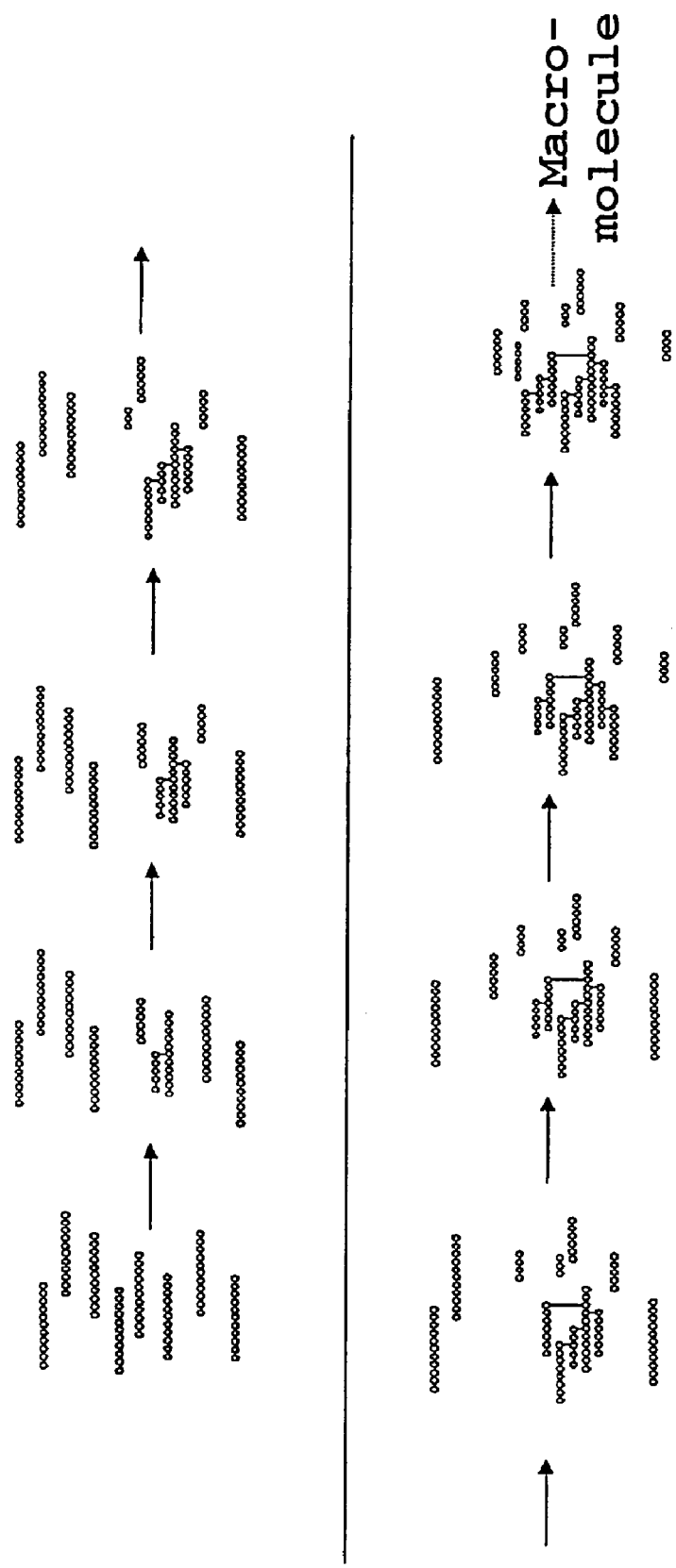
FIG. 11A is a reaction model of BE having the ability to synthesize glycogen.

The mechanism by which BE having (the BE activity)/(the molecular-weight-decreasing activity) of about 500 or less has the ability to synthesize glycogen is not evident. This mechanism is probably based on the principle described below, but is not bound by this principle:

In order for synthesis of high molecular weight α-glucan by BE to occur, the intermolecular branching reaction shown in FIG. 1 must to occur at a higher frequency than the cyclization reaction and the intramolecular branching reaction. The high-frequency intermolecular branching reaction is achieved using low molecular weight amylose as the substrate. Not only the high-frequency intermolecular branching reaction, but also continuous and preferential use of a branched molecule as the substrate, is necessary. The branched molecules, while maintaining their large structural unit, have to be subjected to the action of BE. This is described by reference to a reaction model (FIG. 11A). First, 2 molecules of amylose are converted into a molecule having one α-1,6-bond. Then, the resulting molecule is used as the substrate to generate a molecule having two α-1,6-bonds. Further, by preferentially using the branched molecule as the substrate, a few macromolecular α-glucan molecules and a large number of low-molecular molecules are generated.

Figure 11B:
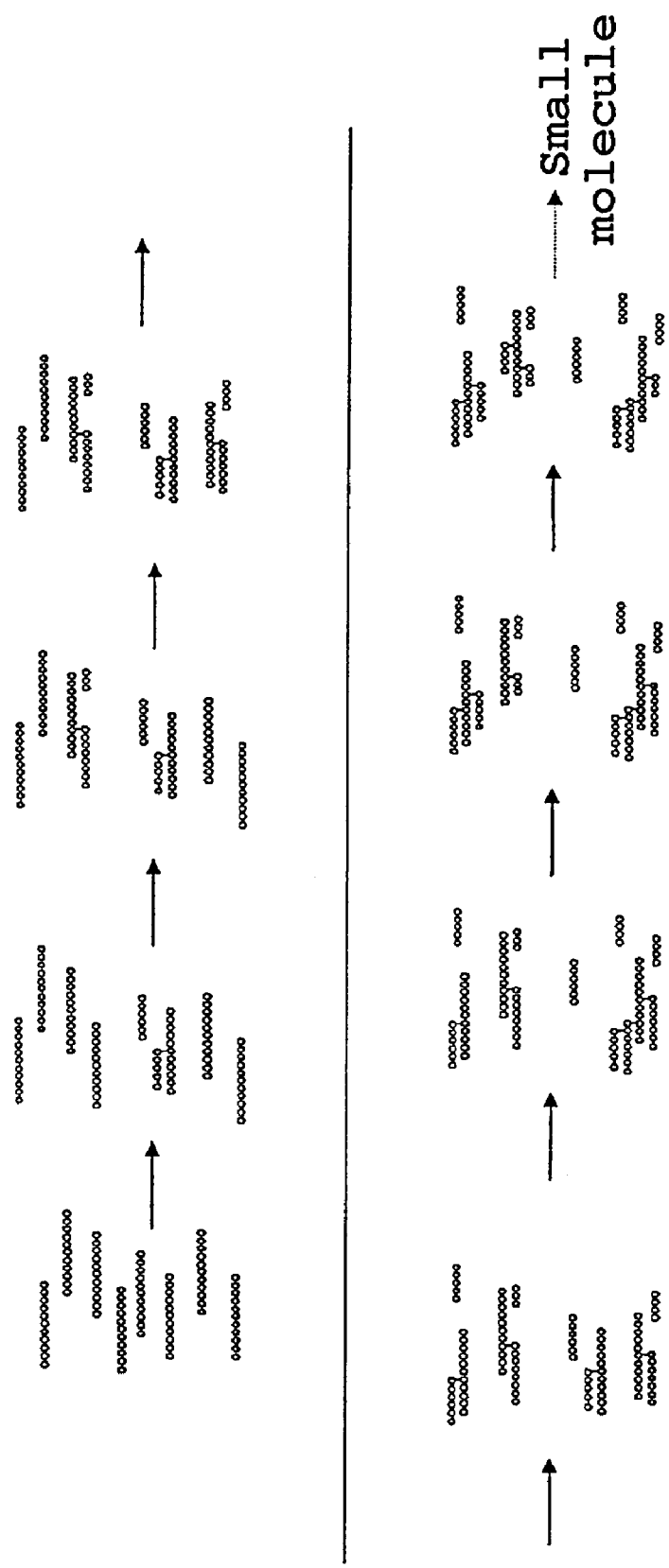
FIG. 11B is a reaction model of BE not having the ability to synthesize glycogen.

On the other hand, in the case of BE not using a branched molecule preferentially as the substrate, or even if a branched molecule is used, when the branched molecule is used in such a manner as to break the large structural unit, a large number of branched molecules are generated and a further macromolecule is scarcely generated (FIG. 11B).

When the percentage of α-1,6-bonds in the whole reaction system are about 10 to 12%, the reaction of BE does not proceed any more in either case.

Here, the amylopectin molecular-weight-decreasing action of BE is described. As shown in Japanese Patent No. 3107358, this reaction is caused by allowing BE to act on a cluster structure of amylopectin and cyclizing it. In this case, BE acts on a branched molecule thereby cyclizing a unit chain in a joint of the cluster structure while maintaining the large structural unit. Accordingly, it is considered that a BE having a relatively high amylopectin molecular-weight-decreasing activity has the property of using a branched molecule preferentially and using it as a reaction substrate while maintaining the large structural unit.

Further, according to the inventors' study, all of the thermostable BEs known at present have the ability to synthesize glycogen. On the other hand, among mesophilic BEs having a low optimum reaction temperature, there are those which do not have the ability to synthesize glycogen.

The BE having the ability to synthesize glycogen are preferably a thermostable BE. The thermostable BE refers to a BE having an optimum reaction temperature of 45° C. or more when the measurement of the BE activity is conducted at varying reaction temperatures.

The optimum reaction temperature of BE having an ability to synthesize glycogen is preferably about 45° C. or more and about 90° C. or less. In this specification, the "optimum reaction temperature" refers to the temperature at which the BE activity is the highest when the aforementioned measurement of the BE activity is conducted varying only the temperatures. The optimum reaction temperature is preferably about 45° C. or more, more preferably about 50° C. or more, still more preferably about 55° C. or more, particularly preferably about 60° C. or more, most preferably about 65° C. or more. Although there is no upper limit of the optimum reaction temperature, the optimum reaction temperature is preferably about 90° C. or less, more preferably about 85° C. or less, still more preferably about 80° C. or less, particularly preferably about 75° C. or less.

The BE having the ability to synthesize glycogen is more preferably BE derived from a thermophilic bacterium or mesophilic bacterium. In this specification, the "thermophilic bacterium" is a microorganism having an optimum growth temperature of about 50° C. or more and hardly growing at about 40° C. or less. Thermophilic bacteria are divided into moderately-thermophilic bacteria and extremely-thermophilic bacteria. The "moderately-thermophilic bacterium" refers to a microorganism having an optimum growth temperature of about 50° C. to about 70° C. The "extremely-thermophilic bacterium" refers to a microorganism having an optimum growth temperature of about 70° C. or more. Among the extremely-thermophilic bacteria, microorganisms having an optimum growth temperature of about 80° C. or more are referred to as "hyperthermophilic bacteria." In contrast, the "mesophilicbacteria" refer to microorganisms having a growth temperature in a usual temperature environment, and particularly to microorganisms having a optimum growth temperature of about 20° C. to about 40° C.

The thermophilic bacterium producing BE having the ability to synthesize glycogen belongs preferably to the genera *Aquifex*, *Rhodothermus*, *Bacillus*, or *Thermosynechococcus*. The mesophilic bacterium producing BE having the ability to synthesize glycogen belongs preferably to the genus *Escherichia*.

BE having the ability to synthesize glycogen is derived more preferably from a bacterium selected from the group consisting of *Aquifex aeolicus*, *Aquifex pyrophilus*, *Rhodothermus obamensis*, *Rhodothermus marinus*, *Bacillus stearothermophilus*, *Bacillus caldovelox*, *Bacillus thermocatenulatus*, *Bacillus caldolyticus*, *Bacillus flavothermus*, *Bacillus acidocaldarius*, *Bacillus caldotenax*, *Bacillus smithii*, *Thermosynechococcus elongatus* and *Escherichia coli*, and derived further more preferably from a bacterium selected from the group consisting of *Aquifex aeolicus*, *Rhodothermus obamensis*, *Bacillus stearothermophilus*, *Bacillus caldovelox*, *Bacillus thermocatenulatus*, *Bacillus caldolyticus* and *Escherichia coli*. Please note that recently, thermophilic bacteria of the genus *Bacillus* are often described as bacteria of the genus *Geobacillus*. For example, the bacterium *Bacillus stearothermophilus* is the same bacterium as *Geobacillus stearothermophilus*.

In this specification, the fact that the enzyme is "derived" from a certain organism means not only that the enzyme is isolated directly from the organism, but also that the organism is utilized in any form to give the enzyme. For example, in the case where an enzyme is isolated from *Escherichia coli* into which a gene encoding the enzyme obtained from an organism was introduced, the enzyme is "derived" from the organism.

The base sequence encoding wild type BE from *Aquifex aeolicus* VF5 is shown in SEQ ID NO: 1, and the amino acid sequence thereof is shown in SEQ ID NO: 2. In this specification, the "wild type" BE encompasses not only BE isolated from a bacterium originally producing BE, but also BE obtained by genetic recombination, having the same amino acid sequence as that of the wild type BE. The method of cloning the base sequence encoding the wild type BE derived from *Aquifex aeolicus* VF5 is described in Nonpatent Document 8 and van der Maarel, M. J. E. C. et al., *Biocatalysis and Biotransformation*, 2003, Vol. 21, pp. 199-207. *Aquifex aeolicus*-derived BE has the excellent property of producing glycogen extremely well from substrates of various Mn.

The base sequence encoding wild type BE from *Rhodothermus obamensis* JCM9785 is shown in SEQ ID NO: 3, and the amino acid sequence thereof is shown in SEQ ID NO: 4. The method of cloning the base sequence encoding wild type BE derived from *Rhodothermus obamensis* JCM9785 is described in Nonpatent Document 11 and Patent Document 3.

The base sequence encoding wild type BE from *Bacillus stearothermophilus* TRBE14 is shown in SEQ ID NO: 5, and the amino acid sequence thereof is shown in SEQ ID NO: 6. The method of cloning the base sequence encoding wild type BE derived from *Bacillus stearothermophilus* TRBE14 is described in Nonpatent Documents 9 and 12. *Bacillus stearothermophilus*-derived BE has the excellent property of producing glycogen extremely well from particularly a low molecular weight substrate. Please note that in bacteria of the genera *Bacillus* and *Escherichia*, TTG and GTG in addition to ATG are used as an initiation codon and translated into methionine, and thus TTG in positions 1-3 in SEQ ID NO: 5 acts as an initiation codon and is translated into methionine. When BE is expressed in other organism using a nucleic acid molecule having the base sequence of SEQ ID NO: 5, T at position 1 is replaced generally by A.

The base sequence encoding wild type BE from *Bacillus stearothermophilus* 1503-4R var. 4 is shown in SEQ ID NO: 7, and the amino acid sequence thereof is shown in SEQ ID NO: 8. The method of cloning the base sequence encoding wild type BE derived from *Bacillus stearothermophilus* 1503-4R var. 4 is described in Kiel, J. A. K. W. et al., *Mol. Gen. Genet.*, 1991, 230: pp. 136-144 and EP0418945B1. TTG in positions 1-3 in SEQ ID NO: 7 acts as an initiation codon and is translated into methionine. When BE is expressed in other organisms using a nucleic acid molecule having the base sequence of SEQ ID NO: 7, T at position 1 is replaced generally by A.

The base sequence encoding wild type BE from *Bacillus caldovelox* IFO15315 is shown in SEQ ID NO: 9, and the amino acid sequence thereof is shown in SEQ ID NO: 10. TTG in positions 1-3 in SEQ ID NO: 9 acts as an initiation codon and is translated into methionine. When BE is expressed in other organisms using a nucleic acid molecule having the base sequence of SEQ ID NO: 9, T at position 1 is replaced generally by A.

The base sequence encoding wild type BE from *Bacillus thermocatenulatus* is shown in SEQ ID NO: 11, and the amino acid sequence thereof is shown in SEQ ID NO: 12. TTG in positions 1-3 in SEQ ID NO: 11 acts as an initiation codon and is translated into methionine. When BE is expressed in other organisms using a nucleic acid molecule having the base sequence of SEQ ID NO: 11, T at position 1 is replaced generally by A.

The base sequence encoding wild type BE from *Bacillus caldolyticus* IFO15313 is shown in SEQ ID NO: 13, and the amino acid sequence thereof is shown in SEQ ID NO: 14. TTG in positions 1-3 in SEQ ID NO: 13 acts as an initiation codon and is translated into methionine. When BE is expressed in other organisms using a nucleic acid molecule having the base sequence of SEQ ID NO: 13, T at position 1 is replaced generally by A.

The base sequence encoding wild type BE from *Thermosynechococcus elongatus* BP-1 is shown in SEQ ID NO: 15, and the amino acid sequence thereof is shown in SEQ ID NO: 16.

The base sequence encoding wild type BE from *Escherichia coli* W3110 is shown in SEQ ID NO: 17, and the amino acid sequence thereof is shown in SEQ ID NO: 18.

The base sequences and amino acid sequences of these wild type BEs are illustrative, and it is known that variants (so-called allele variants) having a slightly different sequence from these sequences can occur naturally. Such naturally occurring variants and variants created by artificially mutating the wild type BEs, in addition to the BEs having these exemplary sequences, can be used in the method of the present invention insofar as they have an ability to synthesize glycogen. For example, the pamphlet WO2000/058445 and Patent Document 3 describe variants of BE derived from *Rhodothermus obamensis*. BE variants preferably have activity equal to, or higher than, that of BE before modification. For example, the amino acid sequence of BE used in the present invention, in a certain embodiment, may be identical with (that is, 100% identical with) an amino acid sequence (that is, a reference amino acid sequence) selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16 and SEQ ID NO: 18; or this amino acid sequence may, in another embodiment, be altered in up to a certain number of amino acids compared with a reference amino acid sequence. Such alterations can be selected from the group consisting of a deletion, a substitution including conservative and non-conservative substitution, or an insertion of at least 1 (preferably 1 or several) amino acids. This alteration may occur at a position of an amino terminus or a carboxyl terminus of a reference amino acid sequence, or may occur at any position other than these termini. Alteration of an amino acid residue may be interspersed with one residue, or a few residues may be contiguous. Those skilled in the art can easily select a BE having a desired property. Alternatively, a gene encoding the objective BE may be directly chemically synthesized. Methods for such chemical synthesis are well-known in the art.

Modification to BE can be carried out using a method well-known in the art, for example, by carrying out site-directed mutagenesis, mutagenesis with a mutagen (treatment of a subject gene with a mutagenic agent such as nitrite, or treatment with UV rays), or error-prone PCR. It is preferable to use site-directed mutagenesis from the viewpoint that the objective mutation is easily obtained, because the objective modification can be introduced at an objective site when site-directed mutagenesis is used. Alternatively, a nucleic acid molecule having an objective sequence may be directly synthesized. Such chemical synthesis methods are well-known in the art. Techniques of site-directed mutagenesis are described in, for example, Nucleic Acids Research, Vol. 10, pp. 6487-6500 (1982).

Upon design of the aforementioned modification, the hydrophobicity index of an amino acid can be considered. Significance of a hydrophobic amino acid index upon impartation interacting biological function to a protein is generally recognized in the art (Kyte, J and Doolittle, R. F. J. *Mol. Biol.* 157(1):105-132, 1982). The hydrophobic nature of an amino acid contributes to the secondary structure of a produced protein and, then, defines interaction between the protein with other molecules (for example, enzyme, substrate, receptor, DNA, antibody, antigen, and the like). An amino acid is assigned a hydrophobicity index based on hydrophobicity and the nature of the charge thereof. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

It is well-known in the art to substitute a certain amino acid with another amino acid having a similar hydrophobicity index, thereby, a protein still having substantially similar biological functions (for example, a protein substantially equivalent in enzyme activity) can be produced. In such amino acid substitutions, the hydrophobicity index is preferably within ±2, more preferably within ±1, still more preferably within ±0.5. It is understood in the art that such a substitution of an amino acid based on hydrophobicity is efficient. As described in U.S. Pat. No. 4,554,101, the following hydrophilicity index is assigned to amino acid residues: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted with another amino acid which has a similar hydrophilicity index, and can still provide a biological equivalent. In such amino acid substitutions, the hydrophilicity index is preferably within ±2, more preferably within ±1, and further preferably within ±0.5.

In the present invention, "conservative substitution" refers to substitution in which a hydrophilicity index or/and a hydrophobicity index are similar, as described above, between the original amino acid and the amino acid to be substituted, in the amino acid substitution. Examples of conservative substitution are well-known to those skilled in the art, and include, but are not limited to substitution among the following each group, for example: arginine and lysine; glutamic acid and aspartic acid; serine and threonine; glutamine and asparagine; and valine, leucine, and isoleucine.

The BE used in the method of the present invention may be isolated from naturally occurring microorganisms producing BE. A wild type BE can be isolated from, for example, *Aquifex aeolicus* VF5, *Bacillus stearothermophilus*, or the like. To exemplify a procedure for isolating BE from *Bacillus stearothermophilus* TRBE14, firstly, *Bacillus stearothermophilus* TRBE14 is inoculated into a suitable medium (for example, L broth (1% Bacto-Tryptone (Difco Laboratories, Detroit, Mich., USA), 0.5% Bacto-Yeast Extract (Difco), 0.5% NaCl, pH 7.3) and cultured at about 50° C. to about 60° C. overnight with shaking. Then, this culture is centrifuged to collect the microbial cells. The resulting cell pellet is suspended in 20 mM Tris-HCl buffer (pH 7.0) and then disrupted by sonication to result in a cell-free extract. The cell-free extract is heated in a water bath at about 60° C. for about 30 minutes. After heating, the cell-free extract is centrifuged by a centrifuge (AVANTI J-25I manufactured by Beckmann) to remove insoluble proteins, and thus obtaining a supernatant. The resulting supernatant is passed through previously equilibrated anion-exchange resin Q-Sepharose to allow BE to be adsorbed onto the resin. The resin is washed with a buffer containing 100 mM sodium chloride to remove impurities. Then, the BE is eluted with a buffer containing 400 mM sodium chloride, to give a *Bacillus stearothermophilus* TRBE14-derived BE enzyme solution. When further purification is necessary, a purified *Bacillus stearothermophilus* TRBE14-derived BE-containing solution can be obtained by combining fractionation with gel filtration chromatography on Sephacryl S-200HR (manufactured by Pharmacia) or the like with fractionation with hydrophobic chromatography on Phenyl-TOYOPEARL 650M (manufactured by Tosoh Corporation) or the like, if necessary. Purification of BE derived from other microbial species can also be carried out in the same manner.

Alternatively, BE used in the method of the present invention can be obtained by introducing a nucleic acid molecule containing a base sequence encoding BE into a suitable host cell, to express BE, and purifying the expressed BE from the host cell or its culture liquid.

Purified BE obtained thusly is treated with trypsin, the resulting trypsin treated fragment is separated by HPLC, and the amino acid sequence of the N-terminus of any of the separated peptide fragments is determined using a peptide sequencer. Then, using synthetic oligonucleotide probes prepared based on the identified amino acid sequence, a suitable genome library or a cDNA library is screened, thereby, a nucleic acid molecule (also referred to as a gene) comprising a base sequence encoding wild type BE can be obtained. Fundamental strategies for preparing the oligonucleotide probes and DNA libraries, and screening them by hybridization of nucleic acids, are well-known to those skilled in the art. For example, see Sambrook et al., *Molecular Cloning: A Laboratory Manual* (1989); *DNA Cloning*, Volumes I and II (edited by D. N. Glover, 1985); *Oligonucleotide Synthesis* (edited by M. J. Gait, 1984); and *Nucleic Acid Hybridization* (edited by B. D. Hames & S. J. Higgins, 1984).

Alternatively, based on homology to a base sequence of a certain BE gene for which a base sequence encoding BE is known, screening can be conducted by hybridization using nucleic acid probes containing at least a part of this base sequence, thereby, a nucleic acid molecule containing another kind of BE gene may be acquired. Such methods are known in the art.

Alternatively, degenerate primers corresponding to a region which is conserved in the amino acid sequence of various BEs are prepared, and PCR is performed, and the base sequence of the BE may be acquired. Such methods are known in the art.

When a genome library is screened, the resulting nucleic acid molecule can be subcloned using methods well-known to those skilled in the art. For example, by mixing λ phage containing an objective gene, suitable *Escherichia coli* and suitable helper phage, a plasmid containing an objective gene can be easily obtained. Thereafter, by transforming suitable *Escherichia coli* using a solution containing the plasmid, an objective gene can be subcloned. By culturing the resulting transformant, a plasmid DNA may be obtained, for example, by an alkaline SDS method, and the base sequence of the objective gene can be determined. A method of determining a base sequence is well-known to those skilled in the art. Further, using primers synthesized based on a base sequence of a DNA fragment, and using a polymerase chain reaction (PCR) employing, for example, the genomic DNA of *Aquifex aeolicus, Rhodothermus obamensis, Bacillus stearothermophilus, Bacillus caldovelox, Bacillus thermocatenulatus, Bacillus caldolyticus* or the like as a template, a BE gene may be directly amplified.

Alternatively, the BE gene can also be chemically synthesized based on a known base sequence (a base sequence (for example, the base sequence of SEQ ID NO: 1, 3, 5, 7, 9, 11, 13, 15 or 17) encoding the amino acid sequence of, for example, SEQ ID NO: 2, 4, 6, 8, 10, 12, 14, 16 or 18).

A base sequence encoding an amino acid sequence of the BE used in the method of the present invention may be altered in up to certain number of nucleotides as compared with the nucleotide sequence (that is, the reference nucleotide sequence) encoding the reference amino acid sequence described above. Such alterations can be selected from the group consisting of a deletion of at least one nucleotide, substitution with at least one nucleotide, including transition and transversion, or an insertion of at least one nucleotide. This alteration may occur at a position of the 5' terminus or the 3' terminus of a reference nucleotide sequence, or may occur at any position other than these termini. Alteration of a base may be interspersed with one base, or a few bases may be contiguous.

A nucleotide alteration can generate a nonsense, missense or frame shift mutation in a code sequence, and thus alteration of the BE encoded by such a altered base sequence can be effected.

When two amino acid sequences are directly compared with each other, these amino acid sequences are preferably identical between these amino acid sequences, in typically at least about 20%, preferably at least about 30%, more preferably at least about 40%, still more preferably at least about 50%, particularly preferably at least about 60%, about 70%, about 80%, about 90%, about 95%, about 96%, about 97%, about 98% or about 99% of amino acids.

In the present specification, the percentage identity of sequences is calculated using maximum matching of GENETYX-WIN Ver.4.0 (Genetics Co., Ltd.). This program aligns sequence data to be analyzed, and sequence data to be compared so that amino acid pairs matched between sequences become greatest while substitution and deletion are considered, and thereupon, gives a score to each of Matches, Mismatches, and Gaps, calculates a sum, outputs alignment at the smallest sum, and calculates identity thereupon (Reference: Takashi, K., and Gotoh, 0.1984. Sequence Relationships among Various 4.5 S RNA Species J. Biochem. 92:1173-1177). In the present specification, the percentage identity of sequences is calculated using maximum matching of GENETYX-WIN Ver. 4.0 under the condition of Matches=−1; Mismatches=1; Gaps=1; *N+=2.

As a wild type enzyme or nucleic acid molecule, an enzyme or nucleic acid molecule having a sequence that is not identical with, but is homologous to, the amino acid sequence of the BE or the base sequence encoding the amino acid sequence of the BE, as specifically described in the present specification (for example, SEQ ID NOS: 1, 2 and the like) can be used. Such an enzyme or nucleic acid molecule having homology with the wild type enzyme or nucleic acid molecule includes, but are not limited to, in the case of a nucleic acid, nucleic acid molecules containing a base sequence having at least about 30%, about 35%, about 40%, about 45%, about 50%, about 55%, about 60%, about 65%, about 70%, about 75%, about 80%, about 85%, about 90%, about 95%, or about 99% identity with a comparison subject sequence, and, in the case of an enzyme, includes, but are not limited to, enzymes having an amino acid sequence having at least about 40%, about 45%, about 50%, about 55%, about 60%, about 65%, about 70%, about 75%, about 80%, about 85%, about 90%, about 95%, or about 99% identity with a comparison subject sequence, when compared in maximum matching in for example GENETYX-WIN Ver. 4.0 under the conditions described above.

A BE encoded by a nucleic acid molecule which hybridizes under stringent condition with a nucleic acid molecule consisting of a base sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15 and SEQ ID NO: 17 as set forth in the Sequence Listing can be used in the present method, as long as the BE has the ability to synthesize glycogen. A BE encoded by a nucleic acid molecule comprising a modified base sequence obtained by modifying a nucleic acid molecule which hybridizes under stringent condition with a nucleic acid molecule consisting of a base sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15 and SEQ ID NO: 17 as set forth in the Sequence Listing can also be used in the present method, as long as the BE has the ability to synthesize glycogen. Those skilled in the art can easily select a desired BE gene.

As used herein, the term "stringent conditions" refers to conditions under which a sequence hybridizes with a specific sequence, but not with a non-specific sequence. Selection of appropriate stringent conditions is well-known to those skilled in the art, and is described, for example, in Molecular Cloning (Sambrook, et al., supra). Specifically, the conditions mean, for example, that a polynucleotide which can be identified using the conditions under which hybridization is performed at 65° C. in a solution containing 50% formamide, 5×SSC (750 mM NaCl, 75 mM trisodium citrate), 50 mM sodium phosphate (pH 7.6), 5× Denhardt's solution (0.2% BSA, 0.2% Ficoll 400 and 0.2% polyvinyl pyrrolidone), 10% dextran sulfate, and 20 µg/ml denatured sheared salmon sperm DNA using a filter on which a DNA derived from a colony or a plaque has been immobilized, and a filter is washed under the condition of 65° C. using a SSC (saline-sodium citrate) solution having a 0.1 to 2-fold concentration (a composition of a SSC solution having a 1-fold concentration is 150 mM sodium chloride, 15 mM sodium citrate).

A nucleic acid molecule used for producing a BE used in the present method may be a nucleic acid molecule which was conservatively modified relative to a nucleic acid molecule comprising a base sequence encoding a wild type BE. The "nucleic acid molecule which was conservatively modified relative to a nucleic acid molecule comprising a base sequence encoding wild type BE" refers to a nucleic acid molecule comprising a base sequence encoding an amino acid sequence which is the same or essentially the same as an amino acid sequence of the wild type BE. The "amino acid sequence which is essentially the same as an amino acid sequence encoded of the wild type BE" refers to an amino acid sequence having essentially the same enzyme activity as that of the wild type BE. Due to the degeneracy of the genetic code, many functionally equivalent base sequences encode a prescribed amino acid sequence. For example, codons GCA, GCC, GCG and GCU all encode the amino acid alanine. Therefore, at all positions where alanine is specified by a GCA codon, the codon can be changed to GCC, GCG or GCU without changing the encoded alanine. Similarly, regarding an amino acid which can be encoded by a plurality of codons, at all positions where the amino acid is specified by a codon, the codon can be changed to any another codon encoding the amino acid without changing the particular amino acid coded. Such a variation in a base sequence is a "silent mutation" which is one kind of conservatively modified mutation. All base sequences in the present specification which encode a polypeptide also include all possible silent mutations of the nucleic acid. Silent mutation includes "silent substitution" in which a coded amino acid is not changed, and the case where a nucleic acid does not originally encode an amino acid (for example, a mutation at an intron portion, a mutation at other untranslated region and the like). When a certain nucleic acid encodes an amino acid, silent mutation has the same meaning as that of silent substitution. In the present specification, "silent substitution" refers to substitution of a base sequence encoding a certain amino acid with another base sequence encoding the same amino acid, in a base sequence. Based on the phenomenon of degeneracy in the genetic code, in the case where there are a plurality of base sequences encoding a certain amino acid (for example, glycine and the like), such silent substitution is possible. Therefore, a polypeptide having an amino acid sequence encoded by a base sequence produced by silent substitution has the same amino acid sequence as that of the original polypeptide. In the art, it is understood that each codon in a nucleic acid (except for AUG which is the only codon usually encoding methionine, and TGG which is the only codon usually encoding tryptophan) can be modified in order to produce functionally the same molecule. Therefore, each silent mutation of a nucleic acid encoding a polypeptide is implicitly included in each described sequence. Preferably, such a modification can be performed so that substitution of cysteine, which is an amino acid that greatly influences the conformation of a polypeptide, is avoided.

A base sequence encoding BE used in the present invention can be changed in conformity with a codon usage in an organism into which the sequence is introduced for expression. Codon usage reflects the usage in a gene which is highly expressed in the organism. For example, when expression is intended in *Escherichia coli*, the sequence can be made to be optimal for expression in *Escherichia coli* according to the published codon usage table (for example, Sharp, et al., Nucleic Acids Research 16, No. 17, p. 8207 (1988)).

An expression vector can be made using a nucleic acid molecule comprising the base sequence modified as described above. A method for preparing an expression vector using a particular nucleic acid sequence is well-known to those skilled in the art.

When a nucleic acid molecule is referred to in the present specification, a "vector" refers to a nucleic acid molecule which can transfer an objective base sequence into an objective cell. Examples of such vectors include a vector which can autonomously replicate in an objective cell, or can be incorporated into a chromosome of an objective cell, and has a promoter at a position suitable for transcribing a modified base sequence. In the present specification, the vector may be a plasmid.

As used herein, an "expression vector" refers to a vector which can express a modified base sequence (i.e. base sequence encoding modified BE) in an objective cell. An expression vector contains, in addition to a modified base sequence, various regulation elements such as a promoter regulating expression thereof and, if necessary, factors necessary for replication in an objective cell and selection of a recombinant (e.g. origin of replication (ori), and a selectable marker such as a drug resistant gene). In an expression vector, a modified base sequence is operably linked so that it is transcribed and translated. Regulation elements include a promoter, a terminator and an enhancer. In addition, when secretion of an expressed enzyme outside a cell is intended, a base sequence encoding a secretion signal peptide is linked upstream of a modified base sequence in the correct reading frame. It is well-known to those skilled in the art that both the type of an expression vector used for introduction into a particular organism (e.g. bacterium), and the kind of a regulation element and other factors used in the expression vector, can vary depending on an objective cell.

As used herein, a "terminator" is a sequence which is situated downstream of a protein coding region, and is involved in termination of transcription upon transcription of a base sequence into an mRNA, and in the addition of a poly A sequence. It is known that a terminator influences the expression level of a gene by involving the stability of an mRNA.

As used herein, a "promoter" refers to a region on a DNA which determines a transcription initiation site of a gene, and directly regulates the transcription frequency, and is a base sequence to which a RNA polymerase binds, thereby, initiating transcription. Since the region of a promoter is usually a region about 2 kbp or less upstream of a first exon of a putative protein coding region in many cases, when a protein coding region in a genome base sequence is predicted using a DNA analyzing software, a promoter region can be putative. A putative promoter region varies with every structural gene, and is usually upstream of a structural gene without limitation, and may be downstream of a structural gene. Preferably, a putative promoter region is present about 2 kbp or less upstream of a first exon translation initiation point.

As used herein, an "enhancer" can be used for enhancing the expression efficiency of an objective gene. Such an enhancer is well-known in the art. A plurality of enhancers can be used, or only one may be used, or may not be used at all.

As used herein, "operably linked" refers to when a desired base sequence is placed under the control of a transcription and translation regulating sequence (e.g. promoter, enhancer and the like) or a translation regulating sequence which effect expression (i.e. operation). In order that a promoter is operably linked to a gene, usually, a promoter is disposed immediately upstream of the gene, but it is not necessary that the promoter is disposed adjacent to the gene.

In order to operably link a modified nucleic acid sequence to the aforementioned regulation element, an objective BE gene should be processed in some cases. Examples include the case where the distance between a promoter and a coding region is too long, and reduction in a transcription efficiency is predicted, the case where the distance between a ribosome binding site and a translation initiation codon is not suitable, and the like. Examples of the procession means include digestion with a restriction enzyme, digestion with an exonuclease such as Bal31 and ExoIII, or introduction of site-directed mutagenesis using a single-stranded DNA such as M13 or PCR.

Then, the expression vector prepared as described above is introduced into a cell, thereby, the BE is expressed.

As used herein, "expression" of an enzyme refers to in vivo or in vitro transcription and translation of a base sequence encoding the enzyme, and production of the encoded enzyme.

A cell into which an expression vector is introduced (also referred to as a host) includes prokaryotes and eukaryotes. A cell into which an expression vector is introduced can be easily selected, taking various conditions such as ease of expression of BE, ease of culturing, growth rate, and safety into consideration. For example, when BE is used in synthesizing glycogen, since it is preferable that the BE does not contain amylase as a contaminant, it is preferable to use a cell which does not produce amylase or produces amylase only at a low level. Examples of such cells include microorganisms such as bacteria and fungi. Examples of more preferable cells include mesophilic microorganisms (e.g. *Escherichia coli*,

*Bacillus subtilis*). A cell may be a microorganism cell, or may be a plant or animal cell. Depending on the cell to be used, an enzyme of the present invention can be an enzyme which has undergone post-translational processing.

In the method of the present invention, the technique of introducing an expression vector into a cell may be any technique known in the art. Examples of such techniques include, for example, transformation, transduction, and transfection. Such techniques of introducing a nucleic acid molecule are well-known in the art, and are conventional, and are described, for example, in Ausubel F. A., et al. ed. (1988), Current Protocols in Molecular Biology, Wiley, New York, N.Y.; Sambrook J, et al. (1987) Molecular Cloning: A Laboratory Manual, 2nd Ed., Cold Spring Harbor Laboratory Press, Cold Spring Harbor, N.Y., and Bessatsu Jikken-igaku "Idenshidounyu & Hatsugen kaiseki jikkenhou", Yodosha, 1997.

(2. Substrate)

In the present invention, α-glucan linked mainly with α-1,4-glucosidic bonds, having a degree of polymerization of 4 or more, is used as the substrate.

In this specification, "α-glucan" refers to a saccharide containing D-glucose as a structural unit, and having at least 2 glucosyl residues or more of a glucosyl residue linked with an α-1,4-glucosidic bond. An α-glucan can be a linear, branched or cyclic molecule. A linear α-glucan has the same meaning as that of α-1,4-glucan. In a linear α-glucan, glucosyl residues are linked only with an α-1,4-glucosidic bonds. A α-glucan containing one or more α-1,6-glucosidic bonds is a branched α-glucan. An α-glucan preferably contains a linear section to some extent. A linear α-glucan having no branching is more preferable.

In this specification, "linked mainly with α-1,4-glucosidic bonds" means that glucosyl residues are linked mainly with α-1,4-glucosidic bonds. The term "mainly" means that α-1,4-glucosidic bonds account for 50% or more of the bonds between glucosyl residues. Bonds between glucosyl residues, other than α-1,4-glucosidic bonds, can be possibly any bonds, usually α-1,6-glucosidic bonds.

It is preferable that the α-glucan used as a substrate has a small number of branches (i.e. the number of α-1,6-glucosidic bonds) in some cases. In such a case, the number of branches per molecule is typically about 0 to about 100, preferably about 0 to about 50, more preferably about 0 to about 25, about 0 to about 10, about 0 to about 5, further preferably about 0.

α-1,6-glucosidic bonds may be distributed in an α-glucan randomly, or may be distributed uniformly. A distribution to such an extent that a linear part of 5 or more of glucosyl residues is formed in an α-glucan is preferable.

α-Glucan used as a substrate in the present invention has a degree of polymerization of 4 (molecular weight 666) or more. α-glucan as a substrate may be a pure substance of uniform molecular weight or a mixture of molecules having various molecular weights. Besides the substrate, a mixture containing glucose not acting as a substrate may be added to the solution. Industrially, a mixture of molecules having various molecular weights is often used as raw saccharide.

The Mn of the saccharides in a solution before initiation of the reaction is greater than about 180, preferably about 181 or more, more preferably about 182 or more, still more preferably about 183 or more, even more preferably about 184 or more, further more preferably about 185 or more. The number-average molecular weight of the saccharide in the solution before initiation of the reaction may be for example about 190 or more, about 195 or more, about 200 or more, about 250 or more, about 300 or more, about 350 or more, about 400 or more, about 450 or more, about 500 or more, about 550 or more, about 600 or more, about 650 or more, about 700 or more, about 750 or more, about 800 or more, about 850 or more, about 900 or more, about 950 or more, about 1,000 or more, about 1,500 or more, about 2,000 or more, or about 2,500 or more. Glucose (molecular weight 180) or α-glucan having a degree of polymerization of 3 or less cannot serve as a substrate for BE, but α-glucan having a degree of polymerization of 4 or more can serve as a substrate for BE. A large amount of glucose is added to a small amount of substrate (for example, those having a degree of polymerization of 4), the Mn of the mixture approximates 180. Even if the Mn of the saccharides in the solution before initiation of the reaction is in the vicinity of 180, the reaction can occur when α-glucan having a degree of polymerization of 4 or more is present. Accordingly, even if the Mn of the saccharides in the solution before initiation of the reaction is in the vicinity of 180, the solution can be used in the reaction as long as it contains α-glucan having a degree of polymerization of 4 or more.

There is no upper limit of the molecular weight of α-glucan used as a substrate in the present invention. The Mn of the saccharides in the solution before initiation of the reaction is about 150,000 or less, preferably about 120,000 or less, more preferably about 100,000 or less, still more preferably about 80,000 or less, further more preferably about 50,000 or less, even more preferably about 20,000 or less, even more preferably less than about 8,000, most preferably less than about 4,000. Particularly, when a low molecular weight α-glucan containing solution wherein the Mn of the saccharides in the solution before initiation of the reaction is about 1,500 or more and less than about 4,000, is used as a substrate, there is an advantage that highly branched α-glucan having an Mw of 1,000,000 or more, highly soluble in water, and with high resistance to pullulanase and α-amylase, can be extremely easily obtained.

α-Glucan used as a substrate in the present invention may be composed exclusively of D-glucoses, or may be a derivative modified to such an extent that the reaction rate by BE is not reduced to 20% or less. The α-glucan is preferably not modified.

α-Glucan used as a substrate in the present invention may be native amylose, preferably debranched starch, debranched dextrin or enzymatically synthesized amylose. The native amylose has some branching structure in some cases. Debranched starch and debranched dextrin also have some branching structure in some cases where the debranching reaction is insufficient. Debranched starch can be a product obtained by degrading starch known in the art with isoamylase or pullulanase. Examples of starch used for obtaining debranched starch include under ground starches such as potato starch, tapioca starch, sweet potato starch and kudzu starch; above-ground starches such as cornstarch (waxy cornstarch, high-amylose cornstarch, and the like), wheat starch, rice starch (for example, waxy rice starch, non waxy rice starch), sago starch and bean starch. Debranched starch is inexpensive, readily available and thus particularly preferable. An α-1,6-glucosidic bond cleaved product of high amylose cornstarch is also preferably used.

(3. Other Enzymes)

(i. 4-α-Glucanotransferase)

The production method of the present invention can further comprise a step of allowing 4-α-glucanotransferase to act on an α-glucan having a degree of polymerization of 2 or more in a solution in which the Mn of saccharides in the solution before initiation of the reaction is greater than 180 and less than 1,500, thereby to produce the substrate.

In the production method of the present invention, 4-α-glucanotransferase may be coexistent with BE.

4-α-Glucanotransferase which can be used in the present invention is an enzyme which transfers a glucosyl group, or a unit consisting of two or more glucoses from a non-reducing terminus of a donor molecule to a non-reducing terminus of an acceptor molecule. Accordingly, this enzyme reaction leads to disproportionation of the degree of polymerization of the maltooligosaccharide initially given. When a donor molecule and an acceptor molecule are the same, an intramolecular transfer is caused and, as a result, a product having a cyclic structure is obtained. 4-α-Glucano transferases are classified into the following 6 types based on their primary structure: types I, II, III, IV, V and Others (Takaha, T. and Smith, S. M. Biotechnol. Genet. Eng. Rev. Vol. 16, pp. 257-280 (1999)). Type I is called cyclodextrin glucanotransferase (referred to herein after as CGTase) (EC 2.4.1.19). Type II is an enzyme also called a disproportionating enzyme, D-enzyme, amylomaltase or the like (EC2.4.1.25) (herein after, referred to as MalQ). Type III is a glycogen debranching enzyme, that is, an enzyme having both 4-α-glucanotransferase activity and amylo-1,6-glucosidase activity (EC 3.2.1.33+EC 2.4.1.25). Hyperthermophilic bacterium-derived 4-α-glucanotransferase is classified into types IV and V. Some enzymes for which no primary structure information has been obtained, but 4-α-glucanotransferase activity is reported, have been classified into "Others." 4-α-Glucanotransferase activity can be determined based on Terada et al. (Applied and Environmental Microbiology, Vol. 65, pp. 910-915 (1999)). According to the properties of 4-α-glucanotransferase, the reaction temperature, reaction pH, and the like for measurement can be adjusted.

4-α-Glucanotransferase is present in microorganisms and plants. Examples of microorganisms producing 4-α-glucanotransferase include *Aquifex aeolicus, Streptococcus pneumoniae, Clostridium butylicum, Deinococcus radiodurans, Haemophilus influenzae, Mycobacterium tuberculosis, Thermococcus litralis, Thermotoga maritima, Thermotoga neapolitana, Chlamydia psittaci, Pyrococcus sp., Dictyoglomus thermophilum, Borrelia burgdorferi, Synechosystis sp., E. coli, Saccharomyces cerevisiae, Thermus aquaticus, Thermus thermophilus*, and the like. Examples of plants producing 4-α-glucanotransferase include tuber and root crops such as potatoes, sweet potatoes, yarn and cassaya; cereals such as corn, rice and wheat; and beans such as peas and soybeans. An organism producing 4-α-glucanotransferase is not limited to these. The 4-α-Glucanotransferase may be commercially available or may be prepared from these organisms by methods known in the art, or may be prepared using a gene of a debranching enzyme of these organisms in a genetic recombination method. Any 4-α-glucanotransferase known in the art can be used.

CGTase (EC 2.4.1.19) is also one kind of 4-α-glucanotransferase and can be used in the production method of the present invention. CGTase which can be used in the present invention is an enzyme capable of catalyzing glycosyltransfer reaction (disproportionating reaction) of maltooligosaccharide. CGTase is an enzyme which recognizes a chain of 6 to 8 glucoses at a non-reducing terminus of a donor molecule and effecting transfer reaction so as to cyclize this moiety, thereby forming cyclodextrin having a degree of polymerization of 6 to 8 and acyclic limit dextrin.

As a CGTase, a well-known CGTase derived from microorganisms or a commercially available CGTase can be used. Preferably, commercially available *Bacillus stearothrmophilus*-derived CGTase (Hayashibara Biochemical Labs., Inc., Okayama), *Bacillus macerans*-derived CGTase (trade name: Contizyme, Amano Pharmaceutical Co., Ltd., Nagoya), or A1 kalophilic *Bacillus* sp. A2-5a-derived CGTase can be used. More preferably, *Alkalophilic Bacillus* sp. A2-5a-derived CGTase can be used. *Alkalophilic Bacillus* sp. A2-5a is a CGTase-producing strain having high activity in the alkali range disclosed in Japanese Laid-open Publication No. 7-107972, and has been deposited under the deposition No. FERM P-13864 by the applicant with the Agency of Industrial Science and Technology, National Institute of Bioscience and Human-Technology, Japan. An organism producing CGTase is not limited to these. CGTase may be a commercially available product or may be prepared from these organisms by methods known in the art, or may be prepared using a gene of CGTase of these organisms in a genetic recombination method Any CGTase known in the art can be used. In the production method of the present invention, 4-α-glucanotransferase other than CGTase is preferably used. When 4-α-glucanotransferase other than CGTase is coexistent with BE, the yield of glycogen is significantly improved compared to the case where CGTase is coexistent with BE.

4-α-Glucanotransferase is preferably added with BE together. However, 4-α-glucanotransferase may be added before or after addition of BE as long as the molecular weight and yield of glycogen produced are not adversely influenced. When 4-α-glucanotransferase is coexistent with BE, the yield of glycogen is significantly improved compared to the case where BE is used alone.

(ii. α-Glucans Having an Mn Greater than 180 and Less than 1,500)

When the α-glucan having an Mn greater than 180 and less than 1,500 is a single substance, an example of the α-glucan includes a maltooligosaccharide having a degree of polymerization of 2 to 9. The α-glucan is preferably a maltooligosaccharide having a degree of polymerization of 3 to 8, more preferably a maltooligosaccharide having a degree of polymerization of 3 to 7, still more preferably a maltooligosaccharide having a degree of polymerization of 4 to 6, particularly preferably a maltooligosaccharide having a degree of polymerization of 4 to 5, most preferably a maltooligosaccharide having a degree of polymerization of 4.

When the α-glucan having an Mn greater than 180 and less than 1,500 is a mixture, an example of the mixture includes a mixture containing maltooligosaccharides having a degree of polymerization of 4 to 12. α-glucan having an Mn greater than 180 and less than 1,500 can contain low molecular weight saccharides such as glucose in addition to maltooligosaccharides having a degree of polymerization of 4 to 12. α-glucan having an Mn greater than 180 and less than 1,500 preferably contains maltooligosaccharides having a degree of polymerization of 4 to 7, and is more preferably maltooligosaccharides having a degree of polymerization of 4 to 7. The maltooligosaccharides having a degree of polymerization of 4 to 7 are also called maltotetraose, maltopentaose, maltohexaose and maltoheptaose, respectively.

(iii. Debranching Enzyme)

The production method of the present invention can also comprise a step of allowing a debranching enzyme to act on low-branched α-glucan having an Mn of 500 or more, thereby to produce the substrate. A debranching enzyme is an enzyme which can cleave an α-1,6-glucosidic bond. A debranching enzyme is classified into two of isoamylase (EC 3.2.1.68), which acts well on both of amylopectin and glycogen, and α-dextrin endo-1,6-α-glucosidase (also referred to as pullulanase) (EC3.2.1.41), which acts well on pullulan. Either of isoamylase and pullulanase can be used in the method of the present invention. A debranching enzyme can be used to produce an α-glucan linked mainly with α-1,4-glucosidic bonds having a degree of polymerization of 4 or more, from an inexpensive material such as starch. The debranching enzyme activity can be determined based on Yokobayashi et al. (*Biochim. Biophys. Acta*, vol. 212, pp. 458-469 (1970)). According to the properties of debranching enzyme, the reaction temperature, reaction pH, and the like for measurement can be adjusted.

A debranching enzyme is present in microorganisms, prokaryotes and plants. Examples of microorganisms producing a debranching enzyme include *Saccharomyces cerevisiae* and *Chlamydomonas* sp. Examples of a prokaryotes producing a debranching enzyme include *Bacillus brevis, Bacillus acidopullulyticus, Bacillus macerans, Bacillus stearothermophilus, Bacillus circulans, Thermus aquaticus, Klebsiella pneumoniae, Thermoactinomyces thalpophilus, Thermoanaerobacter ethanolicus, Pseudomonas amyloderamosa, Flavobacterium odoratum, Falvobacterium* sp., *Cytophaga* sp., *Escherichia coli, Sulfolobus acidocaldarius, Sulfolobus tokodaii, Sulfolobus solfataricus, Metallosphaera hakonensis*. Examples of plants producing a debranching enzyme include potato, sweet potato, corn, rice, wheat, barley, oat, and sugar beet. An organism producing the debranching enzyme is not limited to these. A debranching enzyme may be a commercially available one or may be prepared from these organisms by methods known in the art, or may be prepared using a debranching enzyme gene of these organisms in a genetic recombination method. Any debranching enzyme known in the art can be used.

An debranching enzyme is preferably added before BE is added to the reaction solution.

(iv. Low-Branched α-Glucan Having an Mn of 500 or More)

A low-branched α-glucan having an Mn of 500 or more can be a native α-glucan. In this specification, "low-branched" refers to a low frequency of branching. A low-branched α-glucan may not contain branching. In the low-branched α-glucan, the ratio of the number of α-1,4-glucosidic bonds relative to the number of α-1,6-glucosidic bonds, letting α-1, 6-glucosidic bonds to be 1, is preferably about 10 to about 10000, more preferably about 10 to about 5000, further preferably about 15 to about 1000, further preferably about 20 to about 600. Examples of low-branched α-glucan having an Mn of about 500 or more include starch, amylose, amylopectin and derivatives thereof or partially degraded products thereof. Examples of starches include underground starches such as potato starch, tapioca starch, sweet potato starch and kudzu starch; and above-ground starches such as cornstarch (waxy cornstarch, high-amylose cornstarch, and the like), wheat starch, rice starch (for example, waxy rice starch, non-waxy rice starch), sago starch and bean starch. Examples of an amylose include an amylose isolated from these starches. An amylopectin includes amylopectin isolated from these starches. Low-branched α-glucans having an Mn of 500 or more are known in the art and are readily available.

(4. Method of Producing Glycogen)

In the production method of the present invention, for example, a BE having the ability to synthesize glycogen, a substrate (that is, an α-glucan being linked mainly with α-1, 4-glucosidic bonds and having a degree of polymerization of 4 or more), a buffer, and a solvent dissolving them are used as the major materials. All these materials are added usually at initiation of the reaction, but out of these materials, any materials may be further added during the reaction. As described above, an α-glucan having an Mn greater than 180 and less than 1,500, and 4-α-glucanotransferase, can be used as necessary in the production method of the present invention. A low-branched α-glucan having an Mn of 500 or more and a debranching enzyme can also be used in the production method of the present invention.

Those skilled in the art easily understand that an α-glucan having a desired molecular weight can be obtained by appropriately selecting the amount of substrate, the amount of enzyme, the reaction time and the like used in the production method of the present invention.

The amount of BE contained in the solution when the reaction is initiated is typically about 100 U/g substrate or more, preferably about 500 U/g substrate or more, more preferably about 1,000 U/g substrate or more relative to α-glucan in the solution when the reaction is initiated. The amount of BE contained in the solution when the reaction is initiated is typically about 500,000 U/g substrate or less, preferably about 100,000 U/g substrate or less, more preferably about 80,000 U/g substrate or less relative to α-glucan in the solution when the reaction is initiated. If the amount of BE used is too large, the enzyme denatured during the reaction may be easily aggregated. If the amount of BE used is too small, the yield of α-glucan may be lowered.

The amount of BE used is related to the time which BE is allowed to act on the substrate (that is, α-glucan). This is because when, even if the amount of BE used is small, the reaction proceeds accordingly as the reaction time is increased, while if the amount of BE used is large, the reaction proceeds accordingly even when the reaction time is short. Accordingly, the product of enzyme amount and reaction time has a significant influence on the production of the reaction product. In the method of the present invention, the amount of BE used and the reaction time are adjusted preferably such that the product of the amount of BE used and the reaction time becomes about 150,000 U·hour/g substrate or more. In this specification, "U·hour/g substrate" refers to the product of the amount of the enzyme used per g of substrate (U/g substrate) and the reaction time (hour). The product of the amount of BE used and the reaction time is more preferably about 160,000 U·hour/g substrate or more, even more preferably about 170,000 U·hour/g substrate or more, even more preferably about 180,000 U·hour/g substrate or more, even more preferably about 200,000 U·hour/g substrate or more, even more preferably about 250,000 U·hour/g substrate or more, even more preferably about 300,000 U·hour/g substrate or more, and even more preferably about 350,000 U·hour/g substrate or more. Preferable results can also be obtained even if a BE is allowed to act on a substrate in such amount and time as about 400,000 U·hour/g substrate or more, about 500,000 U·hour/g substrate or more, about 600,000 U·hour/g substrate or more, about 700,000 U·hour/g substrate or more, or about 800,000 U·hour/g substrate or more. BE can be allowed to act on a substrate in a large amount, or for a long time, thereby producing a glycogen. There is no particular upper limit of the product of the amount of a BE allowed to act, and the time, but when too large an amount of BE is allowed to act for a long time, production costs may become too high. The product of the amount of BE allowed to act and the time can be for example about 10,000,000 U·hour/g substrate or less, about 8,000,000 U·hour/g substrate or less, about 50,000,000 U·hour/g substrate or less, about 10,000,000 U·hour/g substrate or less, about 8,000,000 U·hour/g substrate or less, about 5,000,000 U·hour/g substrate or less, about 1,000,000 U·hour/g substrate or less, or the like.

The preferable range of the product of the enzyme amount and the reaction time varies depending on the Mn of the saccharides in the solution prior to initiation of the reaction. Generally, when the Mn of the saccharides in the solution prior to initiation of the reaction is low, a high molecular weight product can be obtained even if the product of the enzyme amount and reaction time is in any range, and the solubility of the resulting product is high. The higher the Mn of the saccharides in the solution prior to initiation of the reaction, the higher the product of the enzyme amount and reaction time necessary for obtaining a highly soluble and high molecular weight product is increased.

When the Mn of the saccharides in the solution prior to initiation of the reaction is less than about 4,000, the product of the amount of BE used and the reaction time is not particularly limited in the method of the present invention. For example, when this product is about 25,000 U·hour/g substrate or more, a high molecular weight product can be obtained. This product is preferably about 35,000 U·hour/g substrate or more, more preferably about 100,000 U·hour/g substrate or more, and most preferably about 150,000 U·hour/g substrate or more.

When the Mn of the saccharides in the solution prior to initiation of the reaction is about 4,000 or more and less than about 8,000, the product of the amount of BE used and the reaction time is preferably about 25,000 U·hour/g substrate or more, more preferably about 50,000 U·hour/g substrate or more, and most preferably about 100,000 U·hour/g substrate or more.

When the Mn of the saccharides in the solution prior to initiation of the reaction is about 8,000 or more and less than about 100,000, the product of the amount of BE used and the reaction time is preferably about 40,000 U·hour/g substrate or more, more preferably about 100,000 U·hour/g substrate or more, and most preferably about 150,000 U·hour/g substrate or more.

When the Mn of the saccharides in the solution prior to initiation of the reaction is about 100,000 or more and less than about 150,000, the product of the amount of BE used and the reaction time is preferably about 150,000 U·hour/g substrate or more, more preferably about 200,000 U·hour/g substrate or more, and most preferably about 300,000 U·hour/g substrate or more.

A solvent used in the production method of the present invention can be any solvent, as long as it is a solvent which does not deteriorate the enzyme activity of BE.

As long as a reaction producing a glycogen can proceed, it is not necessary that the solvent completely dissolves materials used in the production method according to the present invention. For example, when an enzyme is carried on a solid carrier, it is not necessary that the enzyme is dissolved in a solvent. Further, it is not necessary that all of the reaction materials such as α-glucan are dissolved, and it is enough that a part of materials, to such an extent that a reaction can proceed, is dissolved.

A representative solvent is water. A solvent may be water in a cell lysate, accompanying BE upon the preparation of the a fore-mentioned BE.

Any other substance may be contained in a solution containing a BE having the ability to synthesize glycogen and a substrate (that is, an α-glucan being linked mainly with α-1, 4-glucosidic bonds and having an Mn of greater than 180 but not more than 150,000), as long as interaction between the BE and the α-glucan phosphorylase are not hampered. Examples of such substances include buffers, components of microorganisms producing BE (e.g. bacterium, fungus), salts, and medium components.

Amounts of these materials to be used are known, and can be appropriately selected by those skilled in the art.

In the production method according to the present invention, firstly, a reaction solution is prepared. A reaction solution can be prepared, for example, by adding a BE having the ability to synthesize glycogen and a substrate (that is, an α-glucan being linked mainly with α-1,4-glucosidic bonds and having an Mn of greater than 180 but not less than 150,000) to a suitable solvent. Alternatively, a reaction solution may be prepared by mixing solutions each containing a BE having the ability to synthesize glycogen or a substrate (that is, an α-glucan being linked mainly with α-1,4-glucosidic bonds and having an Mn of greater than 180 but not less than 150,000). Any buffer may be added to this reaction solution, if necessary, for the purpose of adjusting the pH as long as it does not inhibit the enzyme reaction. The pH of a reaction solution can be appropriately selected as long as the BE used can exhibit its activity at the pH. The pH of a reaction solution is preferably approximately the optimum pH of the BE used. The pH of a reaction solution is typically about 2 or more, preferably about 3 or more, still more preferably about 4 or more, particularly preferably about 5 or more, further more preferably about 6 or more, and most preferably about 7 or more. The pH of a reaction solution is typically about 13 or less, preferably about 12 or less, more preferably about 11 or less, still more preferably about 10 or less, particularly preferably about 9 or less, and most preferably about 8 or less. In one embodiment, the pH of the reaction solution is typically within 3±optimum pH of the BE used, preferably within 2±optimum pH, more preferably within 1±optimum pH, most preferably within 0.5±optimum pH.

To this reaction solution may be added 4-α-glucanotransferase and a debranching enzyme, if necessary.

The amount of 4-α-glucanotransferase contained in the solution at initiation of the reaction is typically about 0.1 U/g substrate or more, preferably about 0.5 U/g substrate or more, more preferably about 1 U/g substrate or more, based on α-glucan in the solution at initiation of the reaction. The amount of 4-α-glucanotransferase contained in the solution at initiation of the reaction is not particularly limited with respect to the upper limit, and is typically about 50,000 U/g substrate or less, preferably about 10,000 U/g substrate or less, and more preferably about 8,000 U/g substrate or less, based on α-glucan in the solution at initiation of the reaction. If the amount of 4-α-glucanotransferase used is too large, the enzyme denatured during the reaction may be easily aggregated. If the amount of 4-α-glucanotransferase used is too small, the yield of α-glucan may be lowered.

The amount of the debranching enzyme contained in the solution at initiation of the reaction is typically about 10 U/g substrate or more, preferably about 50 U/g substrate or more, and more preferably about 100 U/g substrate or more, based on α-glucan in the solution at initiation of the reaction. The amount of the debranching enzyme contained in the solution at initiation of the reaction is not particularly limited with respect to the upper limit, and is typically about 500,000 U/g substrate or less, preferably not higher than about 100,000 U/g substrate or less, and more preferably about 80,000 U/g substrate or less, based on the α-glucan in the solution at initiation of the reaction. If the amount of debranching enzyme used is too large, the enzyme denatured during the reaction may be easily aggregated. If the amount of debranching enzyme used is too small, the yield of α-glucan may be lowered.

The reaction solution is then heated, if necessary, by the methods known in the art, to start the reaction. The reaction temperature can be any temperature as long as the effect of the invention is obtained. When the BE activity in the reaction solution at reaction initiation is about 5% to about 100% of the activity determined at optimum reaction conditions, the reaction temperature can be typically about 20° C. or more and about 100° C. or less. It is preferable that the temperature of the solution in this reaction step is such a temperature that activity which is about 50% or more, more preferably about 80% or more of activity of BE contained in this solution before a reaction remain after a predetermined reaction time. This reaction temperature is preferably about 30° C. or more, more preferably about 40° C. or more, still more preferably about 50° C. or more, even more preferably about 55° C. or more, particularly preferably about 60° C. or more, and most preferably 65° C. or more. This reaction temperature is about 90° C. or less, preferably about 85° C. or less, more preferably about 80° C. or less, even more preferably about 75° C. or less, particularly preferably about 70° C. or less, and most preferably about 65° C. or less.

The reaction time can be selected taking the reaction temperature, the molecular weight of α-glucan produced by the reaction, and the remaining activity of the enzymes into consideration. The reaction time is typically about 1 hour or more, more preferably about 2 hours or more, still more preferably about 4 hours or more, and most preferably about 6 hours or more. The reaction time is not particularly limited with respect to the upper limit, and is preferably about 100 hours or less, more preferably about 72 hours or less, still more preferably about 36 hours or less, and most preferably about 24 hours or less.

In the production method of the present invention, it is preferable to use neither α-glucan phosphorylase nor glycogen synthase.

In this manner, a solution containing glycogen is produced. The Mw of glycogens produced by the method of the present invention is preferably about 1,000,000 (Da) or more, more preferably about 2,000,000 (Da) or more, still more preferably about 5,000,000 (Da) or more, and most preferably about 10,000,000 (Da) or more. The Mw of glycogen produced by the production method of the present invention is not particularly limited with respect to the upper limit, and for example, glycogen with an Mw of up to about 50,000,000 (Da), up to about 10,000,000 (Da) or up to about 1,000,000,000 (Da) can be synthesized to achieve excellent yields. The Mw of the resulting glycogen can be confirmed by methods known in the art. The Mw of the glycogen can be measured, for example, by the following method.

First, synthesized α-glucan is completely dissolved in 1 N sodium hydroxide and neutralized with a suitable amount of hydrochloric acid, and then the solution containing about 1 μg to about 300 μg α-glucan is subjected to gel filtration chromatography using a differential refractometer and a multi-angle laser-light scattering detector together to determine the average molecular weight.

Specifically, a column Shodex OH-Pack SB806 MHQ (inner diameter 8 mm, length 300 mm, manufactured by Showa Denko K.K.) and a guard column Shodex OH-Pack SB-G (inner diameter 6 mm, length 50 mm, manufactured by Showa Denko K.K.) are used, and a multi-angle laser-light scattering detector (DAWN-DSP, manufactured by Wyatt Technology) and a differential refractometer (Shodex RI-71, manufactured by Showa Denko K.K.) are connected in this order and used as a detector. The column is kept at 40° C., and 0.1 M sodium nitrate solution is used as an eluent at a flow rate of 1 mL/min. α-glucan having a molecular weight of about 10,000 or more is eluted in less than 11 minutes in the HPLC system wherein the piping is adjusted such that a peak of pullulan P-50 (contained in standard sample STANDARD P-82 for GFC (aqueous-based GPC)) manufactured by Shodex is eluted at 9.3 minutes. Specifically, peaks are selected all together from the initial position of elution up to 11 minutes so as to contain both the peak detected by the differential refractometer and the peak detected by the multi-angle laser-light scattering detector as data, and the data are collected using data analysis software (trade name: ASTRA, manufactured by Wyatt Technology) and analyzed by this software to determine the Mw. This method is referred to herein after as the MALLS method. In this analysis method, signals after the above signals are not collected, and thus glucans having a molecular weight of about 10,000 or less is excluded. In the present invention, the Mw determined according to the MALLS method is thus not the Mw of the all glucans in the reaction solution, but the Mw of high molecular weight glucans having a molecular weight of about 10,000 or more. Further, when the length, inner diameter, and the like of the piping between the HPLC column and the detector are changed, the elution time of glucans having a molecular weight of about 10,000 or more can be changed. In such case, those skilled in the art can suitably select the elution time suitable for determining the Mw by the MALLS method according to the method of the present invention using the above-mentioned pullulan P-50.

Glycogen produced by the method of the present invention, similar to native glycogen, has the property of being scarcely degraded with pullulanase and α-amylase. Accordingly, glycogen produced by the method of the present invention can be used in the same manner as native glycogen.

Glycogen produced by the method of the present invention has the property of high solubility. The solubility can be determined according to methods known in the art. For example, a predetermined amount of α-glucan is added to water, stirred for a predetermined time and filtered through a filter to give a filtrate, and the amount of α-glucan dissolved in the filtrate is determined to calculate the ratio of the amount of added α-glucan to the amount of α-glucan dissolved in the filtrate, whereby the solubility can be determined. That is, solubility (%)={(amount of α-glucan in filtrate)/(amount of α-glucans in solution before filtration)}×100. When the produced α-glucan is dried, added in distilled water at 20° C. to be 2 mg/mL, stirred at room temperature for 30 seconds, and filtered through a 0.45-μm filter, its solubility is preferably about 20% or more, more preferably about 30% or more, still more preferably about 40% or more, and further more preferably about 50% or more.

(Uses of Glycogen)

Glycogen produced by the method of the present invention, similar to conventional glycogen, can be utilized in applications such as an immunostimulant, a health-food material, a cosmetic material, a food material (flavoring material), and other industrial materials.

EXAMPLES

In the Examples below, various BEs produced in Production Examples 1, 2, 4, 5, 7 and 8 were used as the BE. *Pseudomonas amyloderamosa*-derived isoamylase (manufactured by Hayashibara Biochemical Labs., Inc.) was used as the debranching enzyme. The activity of the debranching enzyme was determined based on Yokobayashi et al. (*Biochim. Biophys. Acta*, Vol. 212, pp. 458-469 (1970)). *Thermus aquaticus*-derived MalQ (TaqMalQ) was used as the 4-α-glucanotransferase. The enzyme activity of 4-α-glucanotransferase was determined based on Terada et al. (*Applied and Environmental Microbiology*, vol. 65, pp. 910-915 (1999)).

Production Example 1

Recombinant Production of BE Derived from *Aquifex aeolicus* VF5

(A) Preparation of *Aquifex aeolicus* VF5 BE gene

A gene (SEQ ID NO: 1) encoding the amino acid sequence of SEQ ID NO: 2 was chemically synthesized. An SD sequence was added upstream from the translation initiation codon of the gene, and a BamHI site was provided upstream from the SD sequence. An EcoRI site was provided downstream from the translation termination codon. This synthetic gene was cleaved with BamHI and EcoRI to prepare a gene fragment which was then ligated using T4-DNA ligase into plasmid pUC19 (manufactured by Takara Shuzo Co., Ltd.) previously cleaved with BamHI and EcoRI, to give plasmid pAQBE1.

(B) Expression of *Aquifex aeolicus* BE gene in *Escherichia coli*

*Escherichia coli* TG-1 was transformed with this plasmid, and the transformant was diluted and plated on an ampicillin-containing LB agar medium (100 µg/ml ampicillin, 1% tryptone manufactured by Difco, 0.5% yeast extract manufactured by Difco, 0.5% NaCl, 1.5% agar, pH 7.3) so as to give independent colonies, and then cultured at 37° C. overnight. *Escherichia coli* that proliferated on this ampicillin-containing LB agar medium possesses the introduced plasmid. *Escherichia coli* expressing BE could be created in this manner.

The *Escherichia coli* TG-1 strain transformed with the recombinant plasmid pAQBE1 was cultured at 37° C. until the middle logarithmic growth phase (about 3 hours) in a 0.2 Liter of L medium (1% tryptone (Difco), 0.5% yeast extract (Difco), 1% NaCl, pH 7.5) containing ampicillin at a final concentration of 100 µg/ml, and then IPTG (isopropyl-β-D-thiogalactopyranoside) was added at a final concentration of 0.1 mM. Culturing was continued for an additional 21 hours at 37° C. and followed by centrifugation to collect the cells. The cells thus obtained were washed with 50 ml buffer A (10 mM sodium phosphate buffer (pH 7.5)) and then dispersed in 20 ml buffer A, and the cells were disrupted by sonication. The cell-free extract was heated at 70° C. for 30 minutes to denature the *Escherichia coli*-derived proteins and this was used as the BE enzyme solution. This BE enzyme solution, and the liquid obtained by treating pAQBE1-free *Escherichia coli* in the same manner as above, were subjected to SDS-polyacrylamide gel electrophoresis, and their patterns were compared. As a result, it was confirmed that the transformed *Escherichia coli* TG-1 strain expressed the BE gene, and the protein encoded by this gene was produced.

Production Example 2

Recombinant Production of BE Derived from *Bacillus stearothermophilus* TRBE 14

BE derived from *Bacillus stearothermophilus* TRBE 14 was recombinantly produced from *Escherichia coli* TG-1 strain carrying plasmid pUBE821 shown in Nonpatent Document 12 by a method shown in this document.

Production Example 3

Recombinant Production of *Thermus aquaticus*-Derived MalQ (Hereinafter Referred to as TaqMalQ)

TaqMalQ was recombinantly produced from *Escherichia coli* MC1061 strain carrying plasmid pFGQ8 shown in Terada et al. (*Applied and Environmental Microbiology*, vol. 65, pp. 910-915 (1999)) by a method shown in this document.

Production Example 4

Recombinant Production of *Escherichia coli*-Derived BE and Test for Ability to Produce Glycogen (Procedure)

The *Escherichia coli* BE gene was amplified using chromosomal DNA of the *Escherichia coli* W3110 strain as a template using the following primers. The primers were designed in reference to Hilden, I. et al. (2000) *Eur J Biochem* 267, 2150-2155) such that the full-length *Escherichia coli* BE structural gene was amplified. The designed primer sequences are shown in Table 1A below.

TABLE 1A

| Primer 1 (N-terminal side) | ECBEN-NCO | GAA<u>CCATGG</u>CCGATCGTATCGATAGAGACG NcoI site (SEQ ID NO: 21) |
|---|---|---|
| Primer 2 (C-terminal side) | ECBEC-HIN | CCC<u>AAGCTT</u>CATTCTGCCTCCCGAACC HindIII site (SEQ ID NO: 22) |

PCR was carried out using DNA polymerase PyroBest manufactured by Takara Bio Inc. according to recommended protocols. The amplified fragment was inserted into a TA cloning site of pGEM-T Easy (manufactured by Promega), and the resulting plasmid was designated pEBE1. pEBE1 was treated with restriction enzymes NcoI and HindIII to give a fragment. The resulting fragment was ligated into pTrc99A previously treated with the same enzymes (NcoI and HindIII), and in a solution containing this ligated product, *Escherichia coli* TG-1 was transformed. A plasmid was isolated from the transformed *Escherichia coli* TG-1, and the resulting plasmid was designated pEBE2-1.

*Escherichia coli* TG-1 carrying pEBE2-1 was cultured in medium containing 50 µg/mL ampicillin at 37° C. with shaking, and at the late logarithmic phase, IPTG was added to a final concentration of 0.1 mM, and the transformant was cultured at 37° C. overnight.

The cells were collected by centrifugation, and the resultant cell pellet was suspended in 10 mM potassium phosphate buffer (pH 7.5) and disrupted by sonication to result in a liquid. This liquid was centrifuged, resulting in a supernatant, and the supernatant was used as a crude enzyme liquid.

A column charged with Q-Sepharose Fast Flow (Amersham-Pharmacia) was prepared, and the resin was equilibrated with 20 mM Tris-HCl (pH 7). The crude enzyme liquid was applied onto this column thereby adsorbing the crude enzyme liquid onto the resin which was then washed with the same buffer containing 0.1 M NaCl, that is, 20 mM Tris-HCl (pH 7) containing 0.1 M NaCl. The BE activity was eluted with the same buffer containing 0.2 M NaCl (that is, 20 mM Tris-HCl (pH 7) containing 0.2 M NaCl).

patent Document 11 such that the full-length *Rhodothermus obamensis* BE structural gene was amplified. The designed primer sequences are shown in Table 1C below.

TABLE 1C

| Primer 1 (N-terminal side) | ROBEN-ECO | AATCCAACCTTC<u>GAATTC</u>AGCTGGCTCACGGAAGAAGACA<br>EcoRI site<br>(SEQ ID NO: 23) |
|---|---|---|
| Primer 2 (C-terminal side) | ROBEC-PST | AATCAATCAATCAA<u>CTGCAG</u>ACGGTTACCCGTGCTCCGGC<br>PstI site<br>(SEQ ID NO: 24) |

Ammonium sulfate was added to a final concentration of 0.3 M to the eluate having BE activity, followed by subjecting it to hydrophobic chromatography in the following manner to purify the BE enzyme. First, a column charged with Phenyl-Toyopearl 650M (Tosoh Corporation) was prepared and equilibrated with 20 mM Tris-HCl (pH 7) containing 0.3 M ammonium sulfate. The enzyme was adsorbed onto this resin which was then washed with 20 mM Tris-HCl (pH 7). The enzyme was recovered by passing distilled water through the column. Purified BE was obtained in this manner.

(Test for Ability to Synthesize Glycogen)

Amylose A (Mn 2900, manufactured by Nacalai Tesque) or Amylose AS10 (Mw 10,000 (Mn 9100), manufactured by Ajinoki Co., Ltd.) was dissolved in 1 N NaOH and then neutralized with HCl. Immediately thereafter, water, an enzyme solution and a buffer were added to the amylose solution such that the reaction solution had the following composition, and the resulting mixture was reacted at 30° C. for 24 hours. The composition of the reaction solution: *Escherichia coli*-derived BE, 40,000 U/g substrate; concentration of substrate, 0.5 wt %; concentration of potassium phosphate, 20 mM; pH 7.5. The average molecular weight of the glucan synthesized in the reaction solution and yield thereof were examined by the MALLS method. The results are shown in Table 1B below.

TABLE 1B

| | Product (Glucan) | | |
|---|---|---|---|
| Substrate | Mw (kDa) | Mn (kDa) | Yield (%) |
| Amylose A | 3601 | 2508 | 7.8 |
| Amylose AS10 | 3904 | 3450 | 50.4 |

As a result, it was found that *Escherichia coli*-derived BE had the ability to synthesize glycogen having an Mw of 1000 kDa or more.

Production Example 5

Recombinant Production of *Rhodothermus obamensis*-Derived BE

*Rhodothermus obamensis* JCM9785 was obtained from Bio Resource Center, RIKEN, an Independent Administration Institution, Japan. This strain was liquid-cultured in Marine Broth 2216 (manufactured by Difco) at 70° C., and chromosomal DNA was extracted from the grown cells.

The *Rhodothermus obamensis* BE gene was amplified using the above-mentioned chromosomal DNA as a template and the following primers. These primers were designed in reference to base sequence information published in Non- Using DNA polymerase KOD-Plus manufactured by Toyobo Co., Ltd., PCR was carried out in a reaction solution having the following composition under the following conditions:

| Chromosomal DNA (about 0.5 µg/µL) | 2 µL |
|---|---|
| Primer 1 (10 pmol/µL) | 3 µL |
| Primer 2 (10 pmol/µL) | 3 µL |
| ×10 KOD-Plus buffer | 10 µL |
| 2 mM dNTP | 10 µL |
| 25 mM MgSO$_4$ | 4 µL |
| KOD-Plus | 2 µL |
| Distilled water (DW) | 70 µL |

Conditions: Heating at 94° C. for 2 minutes followed by 30 cycles at 94° C. for fifteen seconds, at 55° C. for thirty seconds, and at 68° C. for 2.5 minutes.

The resulting DNA fragment was treated with restriction enzymes EcoRI and PstI and then ligated into pTrc99A previously treated with the same enzymes (EcoRI and PstI), and in a solution containing ligated product, *Escherichia coli* TG-1 strain was transformed. A plasmid was isolated from the transformed *Escherichia coli* TG-1 strain, and the resulting plasmid was designated pRBE1.

The *Escherichia coli* TG-1 strain carrying pRBE1 was cultured in medium containing 50 µg/mL ampicillin at 37° C. with shaking, and at the late logarithmic phase, IPTG was added to a final concentration of 0.1 mM, and the transformant was cultured at 37° C. overnight.

The cells were collected by centrifugation, and resultant cell pellet was suspended in 20 mM Tris-HCl buffer (pH 7) and disrupted by sonication to result in a liquid. The liquid was centrifuged to result in a supernatant, then the supernatant was heated at 70° C. for 30 minutes and centrifuged to recover a supernatant, and the resultant supernatant was used as the crude enzyme solution.

A column charged with Q-Sepharose Fast Flow (Amersham-Pharmacia) was prepared, and the resin was equilibrated with 20 mM Tris-HCl (pH 7). The crude enzyme solution was applied onto this column, thereby adsorbing the crude enzyme solution onto the resin which was then washed with the same buffer containing 0.1 M NaCl. BE activity was eluted with the same buffer containing 0.5 M NaCl. The eluate was dialyzed against 20 mM Tris-HCl (pH 7) to give purified BE. As shown in Example 8 below, the resulting purified BE has the ability to synthesize glycogen having an Mw of 1000 kDa or more.

Production Example 6

Recombinant Production of Kidney Bean-Derived BE and Test for Ability to Synthesize High Molecular Weight Glucan As the BE derived from kidney bean (*Phaseolus vulugaris* L.), KBE2 described in Nozaki, K. et al. (2001) *Biosci. Biotechnol. Biochem.* 65, 1141-1148 was used.

(Test for Ability to Synthesize Glycogen)

Amylose A (Mn 2900, manufactured by Nacalai Tesque) or Amylose AS10 (Mw 10,000 (Mn 9100), manufactured by Ajinoki Co., Ltd.) was dissolved in 1 N NaOH and then neutralized with HCl. Immediately thereafter, water, an enzyme solution and a buffer were added to the amylose solution such that the reaction solution had the following composition, and the resulting mixture was reacted at 30° C. for 24 hours. The composition of the reaction solution: amount of KBE2, 40,000 U/g substrate; concentration of substrate, 0.5 wt %; concentration of potassium phosphate, 20 mM; pH 7.5. The average molecular weight of the glucan synthesized in the reaction solution and yield thereof were examined by the MALLS method. The results are shown in Table 1D below.

TABLE 1D

| Substrate | Product (Glucan) | | |
|---|---|---|---|
| | Mw (kDa) | Mn (kDa) | Yield (%) |
| Amylose A | <10 | <10 | not detected |
| Amylose AS10 | 185.2 | 120.9 | 32 |

As a result, it was found that when KBE2 was used, glycogen of 1000 kDa or more cannot be synthesized.

Production Example 7

Recombinant Production of *Bacillus caldovelox*-Derived BE

*Bacillus caldovelox*-derived BE was recombinantly produced in the same manner as in Production Example 1 except that a gene (SEQ ID NO: 9) encoding *Bacillus caldovelox*-derived BE was used in place of the gene encoding *Aquifex aeolicus*-derived BE and the heating temperature was 60° C.

Production Example 8

Recombinant Production of *Bacillus caldolyticus*-Derived BE

*Bacillus caldolyticus*-derived BE was recombinantly produced in the same manner as in Production Example 1 except that a gene (SEQ ID NO: 13) encoding *Bacillus caldolyticus*-derived BE was used in place of the gene encoding *Aquifex aeolicus*-derived BE and the heating temperature was 60° C.

Measurement Example 1

Measurement of the Amylopectin Molecular-Weight-Decreasing Activity of *Aquifex aeolicus* VF5-Derived BE First, 100 μl of distilled water was added to 50 mg of waxy cornstarch (WCS, manufactured by Sanwa Cornstarch Co., Ltd.) and stirred sufficiently. Then, 900 μl of dimethyl sulfoxide (DMSO) was added thereto, stirred and heated for 20 minutes in a boiling water bath. 8.9 ml of distilled water was added thereto, stirred well and heated for an additional 10 minutes in a boiling water bath. 100 μl of 1 M phosphate buffer (pH 7.5) was added thereto, stirred and used as a substrate solution.

The substrate solution was dispensed in a volume of 800 μL/tube. That is, each tube contained 4 mg WCS. Then, 66.7, 83.3, 100, 116.7, 133.3 or 150 mL of solution containing *Aquifex aeolicus* VF5-derived BE (BE activity: 2.4 U/mL) produced by the same method as in Production Example 1, and 133.3, 116.7, 100, 83.3, 66.7 or 50 μL of diluent, respectively, were added to each tube to adjust the volume of the reaction solution to 1000 μL, and then reacted at 70° C. for 16 hours. The diluent was 10 mM potassium phosphate buffer (pH 7.5) containing 0.05% Triton X-100. When the reaction time reached at 16 hours, the pH of the reaction solution was lowered to from 3 to 4 by addition of 1 N HCl, and the reaction solution was heated at 100° C. for an additional 10 minutes, to terminate the reaction.

After the reaction was terminated, the reaction solution was filtered through a 0.45-μm filter, and the Mw of the product contained in the reaction solution was measured by the MALLS method. The MALLS method is described in detail in "Method of Measurement of Weight-Average Molecular Weight (Mw) of Glucan Produced" below.

Figure 12:
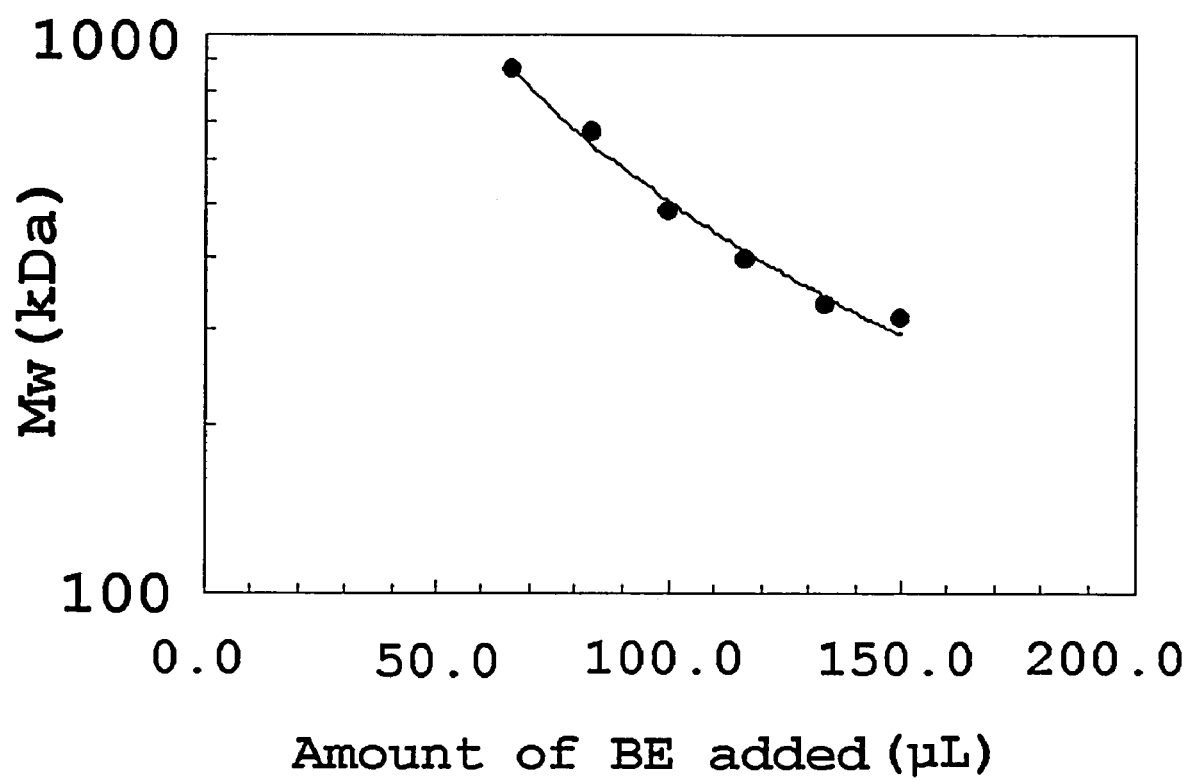
FIG. 12 is a graph showing correlation of the amount of the enzyme with the Mw of the products in the case where *Aquifex aeolicus* VF5-derived BE is allowed to act on waxy cornstarch. The longitudinal axis shows the Mw of the products, and the horizontal axis shows the amounts of BE added.

The logarithm of the calculated Mw (kDa) was plotted on the longitudinal axis (y-axis) while the used amount of the enzyme (μL) was plotted on the horizontal axis (x-axis), and soft MS-Excel manufactured by Microsoft Corporation was used to prepare a power approximation curve. This graph is shown in FIG. 12. An equation of the approximation curve was expressed as $y=24{,}090x^{-1.340}$ ($R^2=0.9896$). The amount V1 (μL) of enzyme necessary for decreasing the Mw of 4 mg WCS of substrate to 400 kDa was calculated from the above equation to be 119 μL. By converting the amount of enzyme per 1 g substrate, the amount V2 (mL) of enzyme necessary for 1 U molecular-weight-decreasing activity is calculated (=(119 μL/1000)×(1000 mg/4 mg)=29.75 (mL)). The molecular-weight-decreasing activity E1 of the enzyme solution is the reciprocal of unit molecular-weight-decreasing activity (E1=1/V2=1/29.75=0.0336) (U/mL). Accordingly, BE activity/molecular-weight-decreasing activity=(2.4 (U/mL)/0.0336 (U/mL))=71.

Measurement Example 2

Measurement of Amylopectin Molecular-Weight-Decreasing Activity of *Bacillus stearothermophilus*-Derived BE The BE activity/molecular-weight-decreasing activity was determined in the same manner as in Measurement Example 1 except that *Bacillus stearothermophilus*-derived BE produced in Production Example 2 was used in place of *Aquifex* aeolicus VF5-derived BE and the reaction temperature was 50° C. As a result, the BE activity/molecular-weight-decreasing activity was 270.

Measurement Example 3

Measurement of Amylopectin Molecular-Weight-Decreasing Activity of *Rhodothermus obamensis*-Derived BE The BE activity/molecular-weight-decreasing activity was determined in the same manner as in Measurement Example 1 except that *Rhodothermus obamensis*-derived BE produced in Production Example 5 was used in place of *Aquifex aeolicus* VF5-derived BE and the reaction temperature was 65° C. As a result, the BE activity/molecular-weight-decreasing activity was 35.

Measurement Example 4

Measurement of Amylopectin Molecular-Weight-Decreasing Activity of *Escherichia coli*-Derived BE The BE activity/molecular-weight-decreasing activity was determined in the same manner as in Measurement Example 1 except that *Escherichia coli*-derived BE produced in Production Example 4 was used in place of *Aquifex aeolicus* VF5-derived BE and the reaction temperature was 30° C. As a result, the BE activity/molecular-weight-decreasing activity was 273.

Measurement Example 5

Measurement of Amylopectin Molecular-Weight-Decreasing Activity of *Bacillus cereus*-Derived BE The BE activity/molecular-weight-decreasing activity was determined in the same manner as in Measurement Example 1 except that *Bacillus cereus*-derived BE produced according to the method described in Nonpatent Document 9 was used in place of *Aquifex aeolicus* VF5-derived BE and the reaction temperature was 30° C. As a result, the BE activity/molecular-weight-decreasing activity was 1086.

Measurement Example 6

Measurement of Amylopectin Molecular-Weight-Decreasing Activity of Kidney Bean-Derived BE The BE activity/molecular-weight-decreasing activity was determined in the same manner as in Measurement Example 1 except that kidney bean-derived BE produced in Production Example 6 was used in place of *Aquifex aeolicus* VF5-derived BE and the reaction temperature was 30° C. As a result, the BE activity/molecular-weight-decreasing activity was 130069.

Measurement Example 7

Measurement of Amylopectin Molecular-Weight-Decreasing Activity of *Bacillus caldovelox*-Derived BE The BE activity/molecular-weight-decreasing activity was determined in the same manner as in Measurement Example 1 except that *Bacillus caldovelox*-derived BE produced in Production Example 7 was used in place of *Aquifex aeolicus* VF5-derived BE and the reaction temperature was 50° C. As a result, the BE activity/molecular-weight-decreasing activity was 466.

Measurement Example 8

Measurement of Amylopectin Molecular-Weight-Decreasing Activity of *Bacillus caldolyticus*-Derived BE The BE activity/molecular-weight-decreasing activity was determined in the same manner as in Measurement Example 1 except that *Bacillus caldolyticus*-derived BE produced in Production Example 8 was used in place of *Aquifex aeolicus* VF5-derived BE and the reaction temperature was 50° C. As a result, the BE activity/molecular-weight-decreasing activity was 402.

The BE activity/molecular-weight-decreasing activity measured by these examples and the ability to synthesize glycogen are summarized in Table 1E below.

TABLE 1E

| Origin | BE activity/ molecular- weight- decreasing activity | Ability to synthesize glycogen | Property |
|---|---|---|---|
| Kidney bean | 130069 | absent | mesophilic |
| Bacillus cereus | 1086 | absent | mesophilic |
| Bacillus caldovelox | 466 | present | thermostable |
| Bacillus caldolyticus | 402 | present | thermostable |
| Escherichia coli | 273 | present | mesophilic |
| Bacillus stearothermophilus | 270 | present | thermostable |
| Aquifex aeolicus | 71 | present | thermostable |
| Rhodothermus obamensis | 35 | present | thermostable |

(Method of Measurement of Weight-Average Molecular Weight (Mw) and Yield of Glucan Produced)

The Mw of glucan produced was measured by the MALLS method in the following manner. A column Shodex OH-Pack SB806 MHQ (inner diameter 8 mm, length 300 mm, manufactured by Showa Denko K.K.) and a guard column Shodex OH-Pack SB-G (inner diameter 6 mm, length 50 mm, manufactured by Showa Denko K.K.) were used, and an multi-angle laser-light scattering detector (DAWN-DSP, manufactured by Wyatt Technology) and a differential refractometer (Shodex RI-71, manufactured by Showa Denko K.K.) were connected in this order and used as the detector. The column was kept at 40° C., and 0.1 M sodium nitrate solution was used as the eluent at a flow rate of 1 mL/min. α-glucan having a molecular weight of about 10,000 or more was eluted in the first 11 minutes in the HPLC system wherein the piping was adjusted such that a peak of pullulan P-50 (contained in standard sample STANDARD P-82 for GFC (aqueous-based GPC)) manufactured by Shodex is eluted at 9.3 minutes. Specifically, peaks were selected all together from the initial position of elution up to 11 minutes so as to contain both the peak detected by the differential refractometer and the peak detected by the multi-angle laser-light scattering detector as data, and the data were collected using data analysis software (trade name: ASTRA, manufactured by Wyatt Technology) and analyzed by this software to determine the Mw. Under these conditions, glucans having a molecular weight of about 10,000 or less are excluded. As the dn/dc (intrinsic refractive index increment) of glucan, 0.145 mL/g was used.

The peak area of the differential refractometer is measured, and this peak area is divided by the dn/dc value, whereby the amount of high molecular weight glucan eluted (g) is calculated. The amount of eluted high molecular weight glucan is divided by the amount of the substrate used in synthesis (which, in the calculating formula, is the product of the concentration of substrate and the volume loaded into HPLC) and multiplied by 100 to determine the yield (%). That is, the yield is calculated according to the following equation:

Yield (%)={(amount of high molecular weight glucan eluted (g))÷[(concentration of substrate (g/mL))× (volume loaded into HPLC (mL))]}×100

Using the amount of high molecular weight glucan having a molecular weight of 1,000,000 or more, the yield of glycogen can be determined.

Example 1

Production of Glycogen from Low Molecular Weight Amylose (1-1: Production from Amylose A)

Amylose A (Mn 2900, manufactured by Nacalai Tesque) was dissolved in 1 N NaOH and then neutralized with HCl. Immediately thereafter, water, an enzyme solution and a buffer were added to the amylose solution such that the reaction solution had the following composition, and the resulting mixture was reacted at 70° C. for 17 hours. The composition of the reaction solution: amount of *Aquifex aeolicus*-derived BE, 10,000, 20,000 or 40,000 U/g substrate; concentration of substrate, 2 wt %; concentration of potassium phosphate, 20 mM; pH 7.5.

Figure 2:
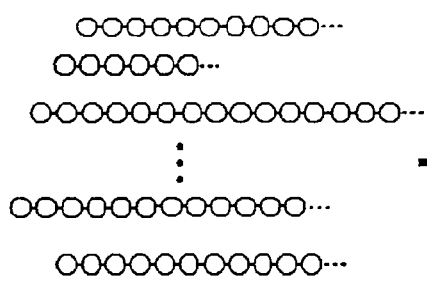
FIG. 2 is a schematic drawing showing production of glycogen from α-glucan.
Figure 2:
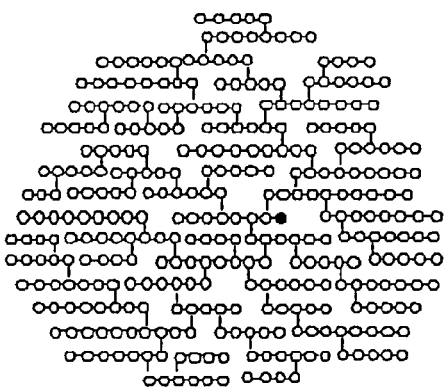
Figure 3:
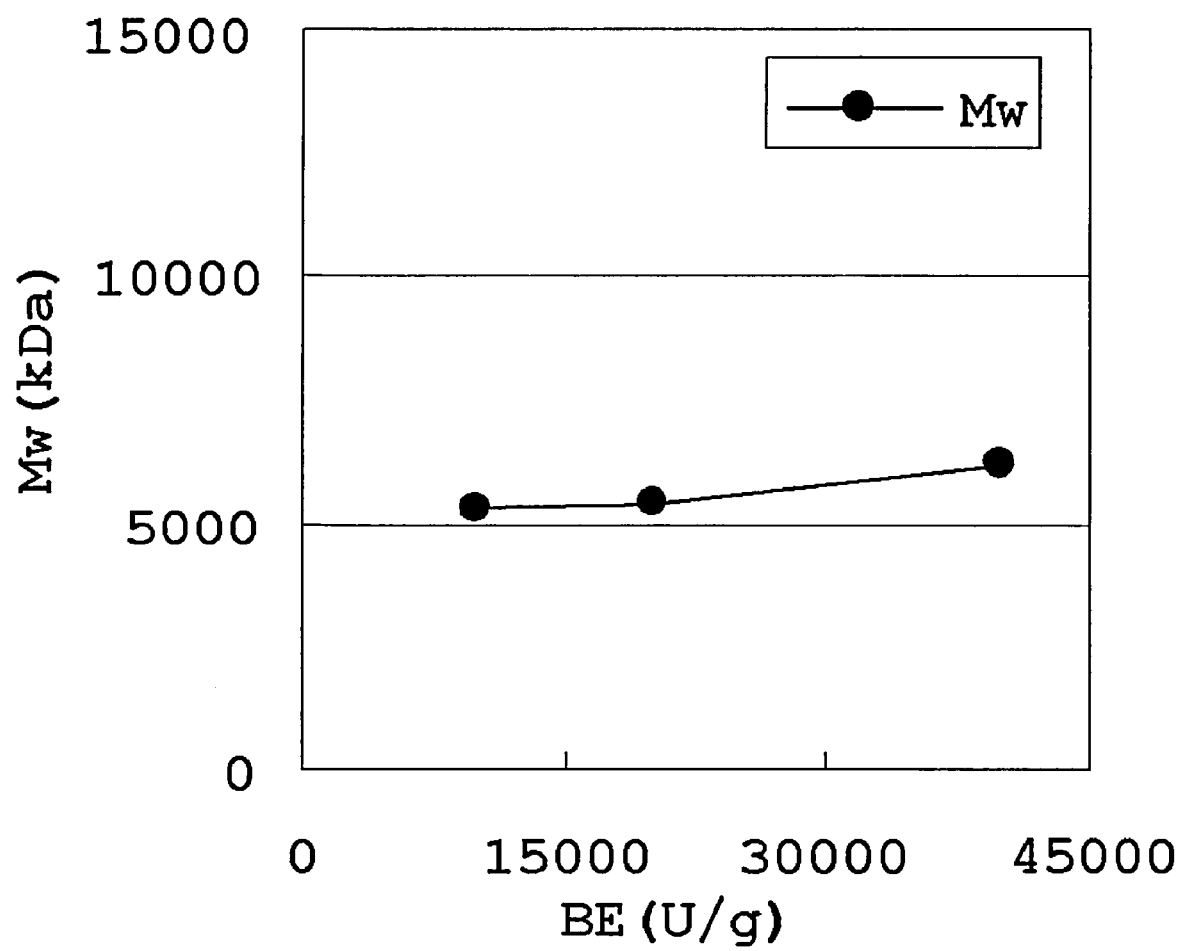
FIG. 3 is a graph showing the Mw of products obtained using various amounts of BE. The amount of BE is expressed in U per g of substrate.

A schematic drawing of glycogen production from low molecular weight α-glucan is shown in FIG. 2. After reaction, the molecular weight of the α-glucan produced was measured. The results are shown in Table 1 and FIG. 3. In Table 1, the yield of glucan shows the total yield of glucans having a molecular weight of 10,000 or more, and the yield of glycogen (%) shows the yield of glucans having a molecular weight of 1,000,000 or more (that is, glycogen). As a result, it was confirmed that when BE is used in an amount of 10,000 to 40,000 U/g substrate, glycogen having an Mw of 1,000,000 or more is produced from Amylose A having an Mn of 2900, and also that almost all glucans produced from Amylose A are glycogen.

(1-2: Production of Glycogen from Substrates of Various Molecular Weights

Amylose AS-5, AS-10, AS-30, AS-70 or AS-110 (having Mw 5000, 10000, 30000, 70000 and 110000 respectively, manufactured by Ajinoki Co., Ltd.) were used as substrates. Since their Mw/Mn is almost 1.1, they have Mn 4,500, 9,100, 27,000, 64,000 and 100,000 respectively.

Each amylose was dissolved in 1 N NaOH and then neutralized with HCl. Immediately thereafter, water, an enzyme solution and a buffer were added to the amylose solution such that the reaction solution had the following composition, and the resulting mixture was reacted at 70° C. for 16 hours. The composition of the reaction solution: amount of *Aquifex aeolicus*-derived BE, 10,000 U/g substrate; concentration of substrate, 2 wt %; concentration of potassium phosphate, 40 mM; pH 7.5.

Figure 4:
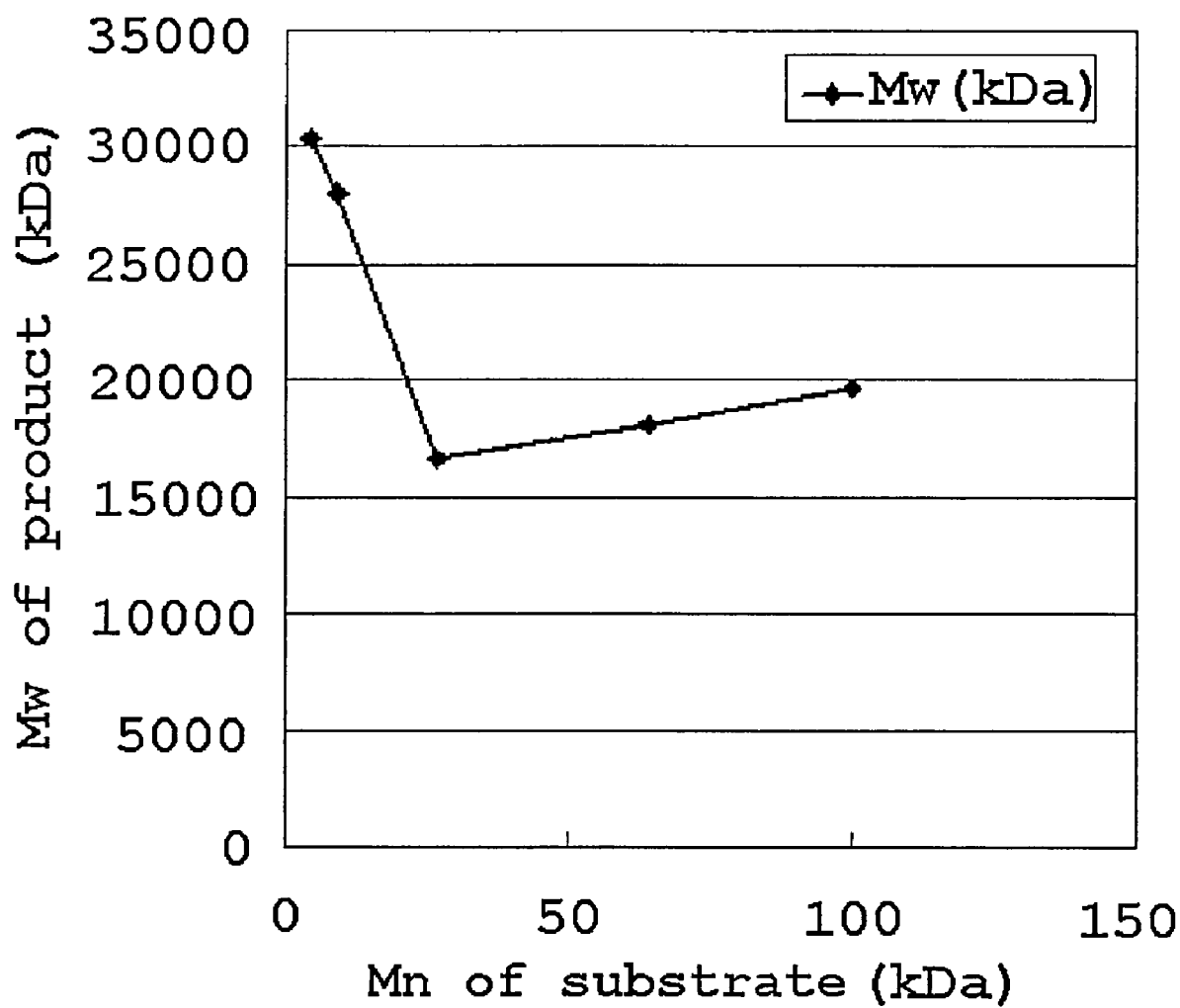
FIG. 4 is a graph showing the Mw of products obtained using a substrate of various molecular weights.

After the reaction, the molecular weight of the α-glucan produced was measured. The results are shown in the following Table 1 and FIG. 4. In Table 1, *Aquifex aeolicus*-derived BE is expressed as Aq.

As a result, it was found that glycogen is produced even from amylose having an Mn of 100,000. When the Mn of the saccharides in the solution before initiation of the reaction was greater than 9100, the molecular weight of the product was split into 2 peaks. When there were split peaks, only the peak of higher molecular weight was measured. There is a trend that the larger the Mn of the saccharides in the solution before initiation of the reaction, the smaller the Mw of the product and the larger the yield.

(1-3: Production of Glycogen from Various Concentrations of Substrate

As a substrate, Amylose A (Mn 2900, manufactured by Nacalai Tesque) was dissolved in 1 N NaOH and then neutralized with HCl. Immediately thereafter, water, an enzyme solution and a buffer were added to the amylose solution such that the reaction solution had the following composition, and the resulting mixture was reacted at 70° C. for 17 hours. The composition of the reaction solution: amount of *Aquifex aeolicus*-derived BE, 10,000 or 40,000 U/g substrate; concentration of substrate, 2, 4, 8 or 12 wt %; concentration of potassium phosphate, 40 mM; pH 7.5.

After the reaction, the molecular weight of the α-glucan produced was measured. The results are shown in Table 1-2. In Table 1-2, the yield of glycogen (%) shows the yield of glucan having a molecular weight of 1,000,000 or more (that is, glycogen).

As a result, it was found that glycogen is produced, at the least, the concentration of substrate is up to about 12%. There was a trend that the higher the concentration of the substrate, the lower the Mw of the product.

TABLE 1

| | | | Reaction conditions | | | Product | | | | | | |
| | | | | | Average molecular weight | | | | | Weight fraction of each component (%) | | |
| | | | Amount of BE | Reaction | | | | Yield of | Yield of | | | |
| Example | Enzyme | Substrate | (U/g substrate) | temperature (° C.) | Mw (kDa) | Mn (kDa) | Mw/Mn | glucan (%) | glycogen (%) | 10-500 (kDa) | 500-1,000 (kDa) | 1,000-2,500 (kDa) |
| 1-1 | Aq | Amylose A (Mn 2900) | 10000 | 75 | 5293 | 4669 | 1.13 | 14.6 | 14.6 | | 0.01 | 0.03 |
| 1-1 | Aq | Amylose A (Mn 2900) | 20000 | 75 | 5448 | 4617 | 1.18 | 18.8 | 18.8 | | 0.06 | 0.42 |
| 1-1 | Aq | Amylose A (Mn 2900) | 40000 | 75 | 6175 | 5214 | 1.18 | 21.1 | 21.0 | 0.34 | 0.33 | 0.19 |
| 1-2 | Aq | Amylose (Mn 4500) | 10000 | 75 | 30380 | 29700 | 1.02 | 13.5 | 13.5 | | | |

TABLE 1-continued

| | | | | | | | | | | | |
|---|---|---|---|---|---|---|---|---|---|---|---|
| 1-2 | Aq | Amylose (Mn 9100) | 10000 | 75 | 28030 | 25890 | 1.08 | 21.3 | 21.3 | | |
| 1-2 | Aq | Amylose (Mn 27000) | 10000 | 75 | 16670 | 15580 | 1.07 | 49.5 | 49.5 | | |
| 1-2 | Aq | Amylose (Mn 64000) | 10000 | 75 | 18100 | 15890 | 1.14 | 64.3 | 64.3 | 0.04 | 0.01 | 0.04 |
| 1-2 | Aq | Amylose (Mn 100000) | 10000 | 75 | 19690 | 14800 | 1.33 | 78.0 | 78.0 | | |

| | Reaction conditions | | | Product | | | |
|---|---|---|---|---|---|---|---|
| | | | | | Weight fraction of each component (%) | | |
| Example | Enzyme | Substrate | Amount of BE (U/g substrate) | Reaction temperature (° C.) | 2,500-5,000 (kDa) | 5,000-10,000 (kDa) | 10,000-50,000 (kDa) | 50,000 or more (kDa) |
| 1-1 | Aq | Amylose A (Mn 2900) | 10000 | 75 | 65.15 | 30.02 | 4.78 | 0.01 |
| 1-1 | Aq | Amylose A (Mn 2900) | 20000 | 75 | 58.41 | 35.00 | 6.06 | 0.05 |
| 1-1 | Aq | Amylose A (Mn 2900) | 40000 | 75 | 41.71 | 49.76 | 7.61 | 0.06 |
| 1-2 | Aq | Amylose (Mn 4500) | 10000 | 75 | | 0.06 | 99.94 | 0.00 |
| 1-2 | Aq | Amylose (Mn 9100) | 10000 | 75 | | 0.12 | 99.39 | 0.49 |
| 1-2 | Aq | Amylose (Mn 27000) | 10000 | 75 | 0.21 | 7.28 | 92.42 | 0.08 |
| 1-2 | Aq | Amylose (Mn 64000) | 10000 | 75 | 0.01 | 12.41 | 87.39 | 0.10 |
| 1-2 | Aq | Amylose (Mn 100000) | 10000 | 75 | 0.14 | 19.41 | 79.86 | 0.59 |

TABLE 1-2

| | Reaction conditions | | | | Product | | | |
|---|---|---|---|---|---|---|---|---|
| | | | | | Average molecular weight | | | |
| Example | Enzyme | Amount of BE (U/g substrate) | Substrate | Concentration of Substrate (wt %) | Reaction temperature (° C.) | Mw (kDa) | Mn (kDa) | Mw/Mn | Yield of glycogen (%) |
| 1-3 | Aq | 10000 | Amylose A | 2 | 75 | 6799 | 2843 | 2.39 | 11.4 |
| 1-3 | Aq | 10000 | Amylose A | 4 | 75 | 4097 | 2467 | 1.66 | 16.0 |
| 1-3 | Aq | 10000 | Amylose A | 8 | 75 | 2257 | 1350 | 1.67 | 21.0 |
| 1-3 | Aq | 10000 | Amylose A | 12 | 75 | 1998 | 392.6 | 5.09 | 13.5 |
| 1-3 | Aq | 40000 | Amylose A | 2 | 75 | 6725 | 2227 | 3.02 | 14.4 |
| 1-3 | Aq | 40000 | Amylose A | 4 | 75 | 5305 | 3239 | 1.64 | 21.5 |
| 1-3 | Aq | 40000 | Amylose A | 8 | 75 | 2697 | 1339 | 2.01 | 28.8 |

Aq: *Aquifex aeolicus*-derived branching enzyme
Mw: weight-average molecular weight
Mn: number-average molecular weight Example 2

Production of Glycogen from Starch (2-1: Production of Glycogen from Cornstarch)

Cornstarch (manufactured by Wako Pure Chemical Industries, Ltd.) (2 wt %) was suspended in water and heated at 100° C. for 30 minutes, whereby the cornstarch was gelatinized. This mixture was cooled to 40° C., and isoamylase (abbreviated as IAM, 5000 or 50000 U/g substrate, manufactured by Hayashibara Biochemical Labs., Inc.) was added thereto and reacted at 40° C. for 4 hours, 6 hours, 8 hours or 20 hours, where by amylose was produced. Thereafter, this solution was adjusted to pH 7.5 with 5 mM potassium phosphate buffer, and *Aquifex aeolicus*-derived BE was added thereto give a mixture in which the concentration of the substrate is 2 wt % and the amount of BE is 10000, 20000, 40000 or 60000 U/g substrate, and then reacted for 20 hours at 55° C., 65° C., 70° C. or 75° C.

Figure 5:
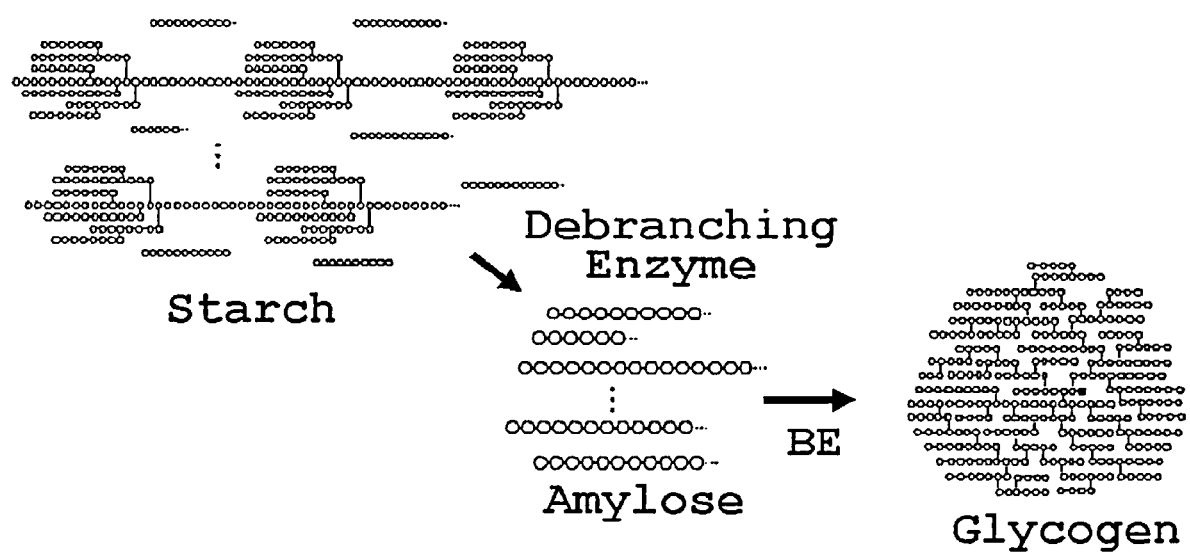
FIG. 5 is a schematic drawing of are action wherein starch is degraded with a debranching enzyme to give amylose, and BE is allowed to react with the amylose to produce glycogen.
Figure 6:
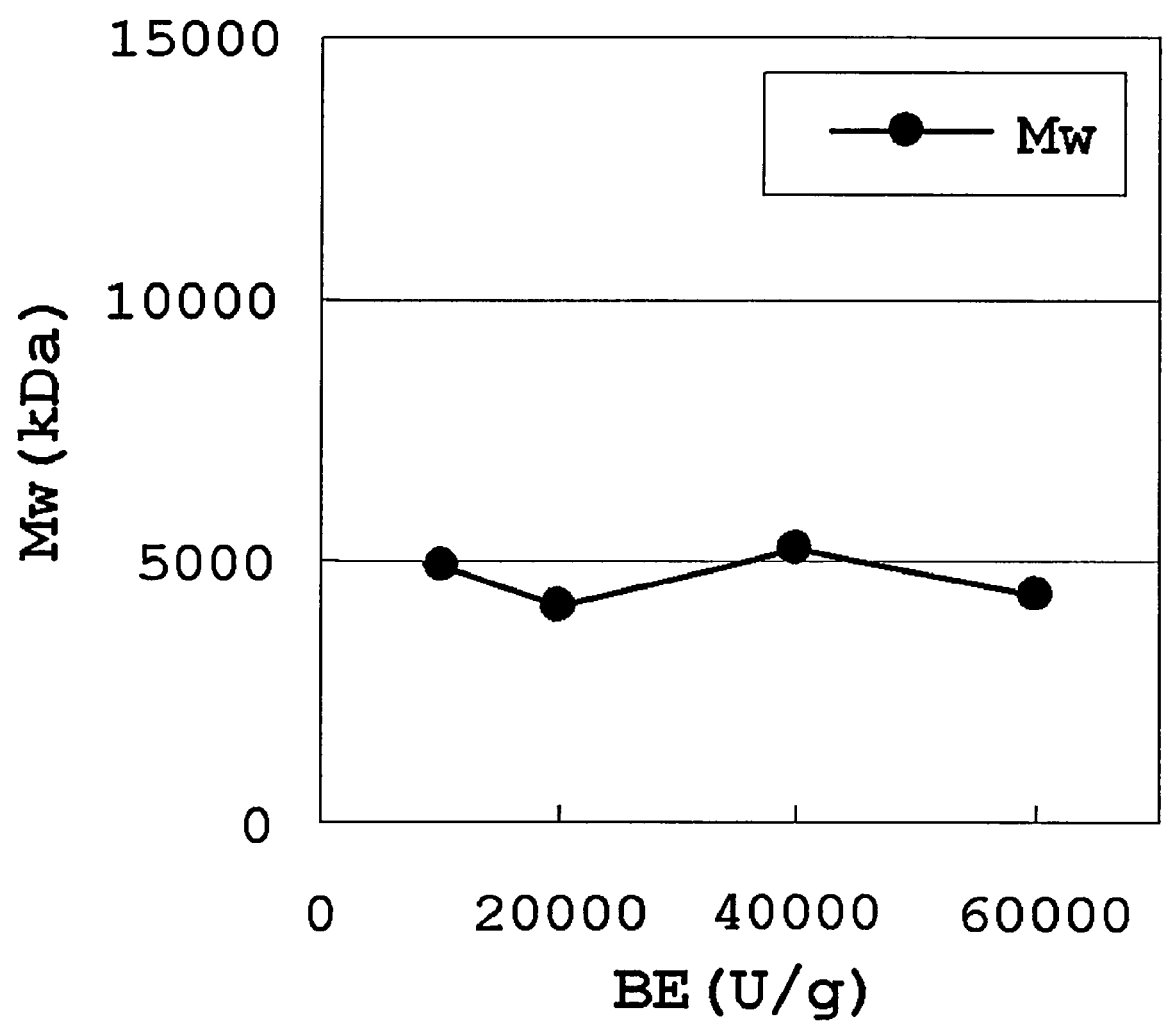
FIG. 6 is a graph showing the Mw of products obtained when isoamylase and various amounts of BE are used to produce α-glucan from starch. The amount of BE is expressed in U per g of substrate.

A schematic drawing of the reaction wherein starch is degraded with a debranching enzyme to give amylose and then the amylose is reacted with BE to produce glycogen is shown in FIG. 5. After the reaction, the molecular weight of the α-glucan produced was measured. The results are shown in following Table 2 and FIG. 6. FIG. 6 is a graph plotting the results where the amount of IAM was 5000 U/g substrate, and the amount of BE was 10000, 20000, 40000 or 60000 U/g substrate. In Table 2, the yield of glycogen (%) shows the yield of glucan having a molecular weight of 1,000,000 or more (that is, glycogen).

TABLE 2

| Amount of IAM (U/g substrate) | Reaction temperature of IAM (°C.) | Reaction time of IAM (hours) | Amount of BE (U/g substrate) | Reaction temperature of BE (°C.) | Reaction time of BE (hours) | Mw of product (kDa) | Mn of product (kDa) | Mw/Mn | Yield of glycogen (%) |
|---|---|---|---|---|---|---|---|---|---|
| 5000 | 40 | 20 | 10000 | 70 | 20 | 4866 | 3637 | 1.34 | 35.4 |
| 50000 | 40 | 20 | 10000 | 70 | 20 | 5076 | 3047 | 1.67 | 33.4 |
| 5000 | 40 | 20 | 20000 | 70 | 20 | 4078 | 3298 | 1.24 | 40.6 |
| 50000 | 40 | 20 | 20000 | 70 | 20 | 5431 | 3015 | 1.80 | 33.6 |
| 5000 | 40 | 20 | 40000 | 70 | 20 | 5215 | 3779 | 1.38 | 38.4 |
| 50000 | 40 | 20 | 40000 | 70 | 20 | 5481 | 3407 | 1.61 | 33.6 |
| 5000 | 40 | 20 | 60000 | 70 | 20 | 4367 | 2970 | 1.47 | 31.9 |
| 50000 | 40 | 20 | 60000 | 70 | 20 | 4782 | 2930 | 1.63 | 30.4 |
| 5000 | 40 | 4 | 20000 | 55 | 20 | 6579 | 5787 | 1.14 | 42.7 |
| 5000 | 40 | 4 | 20000 | 65 | 20 | 4998 | 4255 | 1.17 | 42.5 |
| 5000 | 40 | 4 | 20000 | 75 | 20 | 4632 | 3534 | 1.31 | 40.7 |
| 5000 | 40 | 6 | 20000 | 55 | 20 | 5710 | 4947 | 1.15 | 46.4 |
| 5000 | 40 | 6 | 20000 | 65 | 20 | 7302 | 5437 | 1.34 | 39.5 |
| 5000 | 40 | 6 | 20000 | 75 | 20 | 4873 | 3781 | 1.29 | 40.1 |
| 5000 | 40 | 8 | 20000 | 55 | 20 | 6583 | 5587 | 1.18 | 42.1 |
| 5000 | 40 | 8 | 20000 | 65 | 20 | 6676 | 5057 | 1.32 | 40.7 |
| 5000 | 40 | 8 | 20000 | 75 | 20 | 5950 | 3550 | 1.68 | 38.8 |
| 5000 | 40 | 20 | 20000 | 55 | 20 | 7044 | 5979 | 1.18 | 36.8 |
| 5000 | 40 | 20 | 20000 | 65 | 20 | 6028 | 4905 | 1.23 | 37.2 |
| 5000 | 40 | 20 | 20000 | 75 | 20 | 5284 | 4053 | 1.30 | 36.8 |

BE: *Aquifex aeolicus*-derived branching enzyme
IAM: *Pseudomonas amyloderamosa*-derived isoamylase
Mw: Weight-average molecular weight
Mn: Number-average molecular weight As a result, it was found that glycogen is produced from an isoamylase degraded product of cornstarch. Almost irrespective of the amount of isoamylase and the amount of BE, glycogen with an Mw of about 5,000,000 was obtained in a yield of about 30% or more. When the reaction time of isoamylase was 4 hours or more, glycogen was produced. Glycogen was produced at any BE reaction temperatures of 55° C., 65° C., 70° C. or 75° C.

(2-2: Production of Glycogen from Various Kinds of Starches

Cornstarch (manufactured by Wako Pure Chemical Industries, Ltd.), waxy cornstarch (manufactured by Roquette), wheat starch (manufactured by Wako Pure Chemical Industries, Ltd.), potato starch (manufactured by Wako Pure Chemical Industries, Ltd.) or tapioca starch (manufactured by VEDAN ENTERPRISE Co., Ltd.) (2 wt %) was suspended in water and heated at 100° C. for 30 minutes, whereby the starch was gelatinized. This mixture was cooled to 40° C., and isoamylase (5000 U/g substrate, manufactured by Hayashibara Biochemical Labs., Inc.) was added thereto and reacted at 40° C. for 20 hours, whereby amylose was produced. Thereafter, this solution was adjusted to pH 7.5 with 5 mM potassium phosphate buffer, and *Aquifex aeolicus*-derived BE was added thereto to give a mixture in which the concentration of the substrate is 2 wt % and the amount of BE is 20000 U/g substrate, and then reacted for 20 hours at 55° C., 65° C. or 75° C.

After the reaction, the molecular weight of the α-glucan produced was measured. The results are shown in Table 3 below.

As a result, it was found that various kinds of starches can be used as isoamylase substrates to produce glycogen.

(2-3: Production of Glycogen from Starch Using *Bacillus stearothermophilus*-Derived BE Cornstarch (manufactured by Wako Pure Chemical Industries, Ltd.) (2 wt %) was suspended in water and heated at 100° C. for 30 minutes, whereby the starch was gelatinized. This mixture was cooled to 40° C., and isoamylase (5000 U/g substrate, manufactured by Hayashibara Biochemical Labs., Inc.) was added thereto and reacted at 40° C. for 20 hours, whereby amylose was produced. Thereafter, this solution was adjusted to pH 7.5 with 40 mM potassium phosphate buffer, and *Bacillus stearothermophilus*-derived BE was added thereto to give a mixture in which the concentration of the substrate is 2 wt % and the amount of the BE is 20000 U/g substrate, and then reacted at 55° C. for 20 hours.

After the reaction, the molecular weight of the α-glucan produced was measured. The results are shown in Table 3 below. In Table 3, the yield of glucan shows the total yield of glucans having a molecular weight of 10,000 or more, and the yield of glycogen (%) shows the yield of glucans having a molecular weight of 1,000,000 or more (that is, glycogen).

As a result, it was found that glycogen can be produced even using the *Bacillus stearothermophilus*-derived BE.

TABLE 3

| | | Reaction conditions | | | Product | | | | | | | | | |
|---|---|---|---|---|---|---|---|---|---|---|---|---|---|---|
| | | Substrate | Amount of BE enzyme | Reaction | Average molecular weight | | | Yield of | Yield of | Weight fraction of each component (%) | | | | |
| Example | Enzyme | (all are debranched) | (U/g substrate) | temperature (°C.) | Mw (kDa) | Mn (kDa) | Mw/Mn | Glucan (%) | Glycogen (%) | 10-500 (kDa) | 500-1,000 (kDa) | 1,000-2,500 (kDa) | 2,500-5,000 (kDa) | 5,000-10,000 (kDa) | 10,000-50,000 (kDa) | 50,000 or more (kDa) |
| 2-2 | Aq | Cornstarch | 20000 | 55 | 6378 | 4769 | 1.34 | 35.1 | 34.5 | — | — | — | — | — | — | — |
| 2-2 | Aq | Cornstarch | 20000 | 65 | 6220 | 4582 | 1.36 | 38.5 | 37.8 | — | — | — | — | — | — | — |
| 2-2 | Aq | Cornstarch | 20000 | 75 | 5391 | 3503 | 1.54 | 37.6 | 37.0 | 0.50 | 1.19 | 1.66 | 64.78 | 26.69 | 4.74 | 0.45 |
| 2-2 | Aq | Waxy cornstarch | 20000 | 55 | 13470 | 11910 | 1.13 | 30.2 | 30.1 | — | — | — | — | — | — | — |
| 2-2 | Aq | Waxy cornstarch | 20000 | 65 | 14910 | 12840 | 1.16 | 25.8 | 25.8 | — | — | — | — | — | — | — |
| 2-2 | Aq | Waxy cornstarch | 20000 | 75 | 14460 | 11370 | 1.27 | 25.1 | 25.1 | 0.09 | 0.09 | 0.14 | 0.29 | 27.44 | 71.32 | 0.63 |
| 2-2 | Aq | Wheat starch | 20000 | 55 | 9999 | 9050 | 1.10 | 35.1 | 35.0 | — | — | — | — | — | — | — |
| 2-2 | Aq | Wheat starch | 20000 | 65 | 10270 | 6984 | 1.47 | 35.9 | 35.8 | — | — | — | — | — | — | — |
| 2-2 | Aq | Wheat starch | 20000 | 75 | 7532 | 4815 | 1.56 | 37.3 | 37.1 | 0.27 | 0.15 | 0.22 | 42.47 | 44.61 | 11.51 | 0.76 |
| 2-2 | Aq | Potato starch | 20000 | 55 | 13450 | 8419 | 1.60 | 32.5 | 32.3 | — | — | — | — | — | — | — |
| 2-2 | Aq | Potato starch | 20000 | 65 | 11760 | 7843 | 1.50 | 29.6 | 29.5 | — | — | — | — | — | — | — |
| 2-2 | Aq | Potato starch | 20000 | 75 | 11900 | 6656 | 1.79 | 30.3 | 30.2 | 0.14 | 0.10 | 1.82 | 18.23 | 54.92 | 22.23 | 2.57 |
| 2-2 | Aq | Tapioca starch | 20000 | 55 | 10520 | 6977 | 1.51 | 41.8 | 41.5 | — | — | — | — | — | — | — |
| 2-2 | Aq | Tapioca starch | 20000 | 65 | 8100 | 6134 | 1.32 | 42.2 | 41.8 | — | — | — | — | — | — | — |
| 2-2 | Aq | Tapioca starch | 20000 | 75 | 7835 | 5262 | 1.49 | 35.0 | 34.8 | 0.02 | 0.42 | 1.02 | 38.65 | 48.15 | 10.77 | 0.97 |
| 2-3 | Bst | Cornstarch | 20000 | 55 | 1126 | 398.7 | 2.82 | 15.2 | 5.3 | 7.91 | 57.08 | 30.62 | 3.44 | 0.60 | 0.35 | 0.01 |

Aq: *Aquifex aeolicus*-derived branching enzyme
Bst: *Bacillus stearothermophilus*-derived branching enzyme
Mw: weight-average molecular weight
Mn: number-average molecular weight (2-3: Production of Glycogen Using Isoamylase and BE Together Cornstarch (manufactured by Wako Pure Chemical Industries, Ltd.) (1 wt %) was suspended in water and heated at 100° C. for 30 minutes, whereby the starch was gelatinized. This mixture was cooled to 65° C., and isoamylase (500000 U/g substrate, manufactured by Hayashibara Biochemical Labs., Inc.) and *Aquifex aeolicus*-derived BE (60000 U/g substrate) were added thereto, and this solution was adjusted to pH 7.5 with 40 mM potassium phosphate buffer and reacted at 65° C. for 16 hours.

After the reaction, the molecular weight of the α-glucan produced was measured. As a result, it was found that glycogen can be produced even by allowing isoamylase and BE to act together on starch.

Example 3A

Production of Glycogen by Allowing 4-α-Glucanotransferase and BE to Act on Short Saccharide Chain Amylose Together (3-1: Production of Glycogen Using *Aquifex aeolicus*-Derived BE and TaqMalQ A substrate (maltopentaose (G5), maltohexaose (G6) or maltoheptaose (G7)) was dissolved in water, and water, an enzyme solution and a buffer were added to the substrate solution such that the reaction solution had the following composition, and the resulting mixture was reacted at 65° C. for 17 hours. The composition of the reaction solution: amount of *Aquifex aeolicus*-derived BE, 40000, 80000 or 160000 U/g substrate; TaqMalQ, 10 U/g substrate; concentration of substrate, 1%; concentration of potassium phosphate, 10 mM; pH 7.5.

Figure 7:
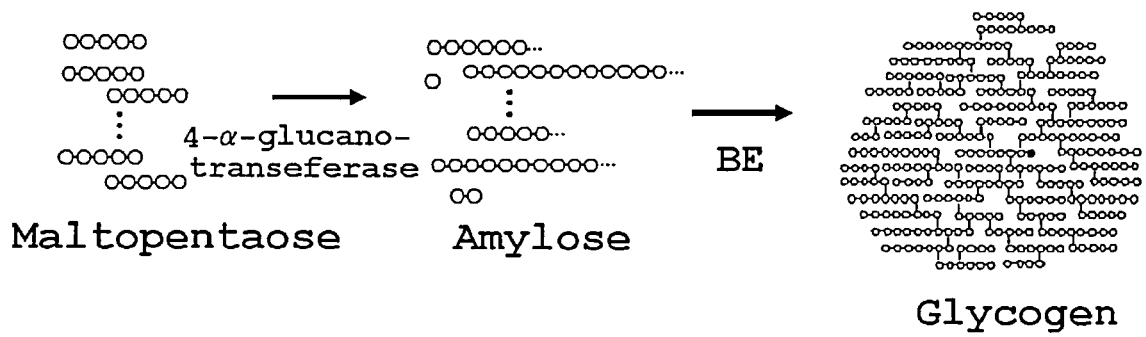
FIG. 7 is a schematic drawing showing that amylose is produced from maltopentaose by 4-α-glucanotransferase, and glycogen is produced from amylose by BE.
Figure 8:
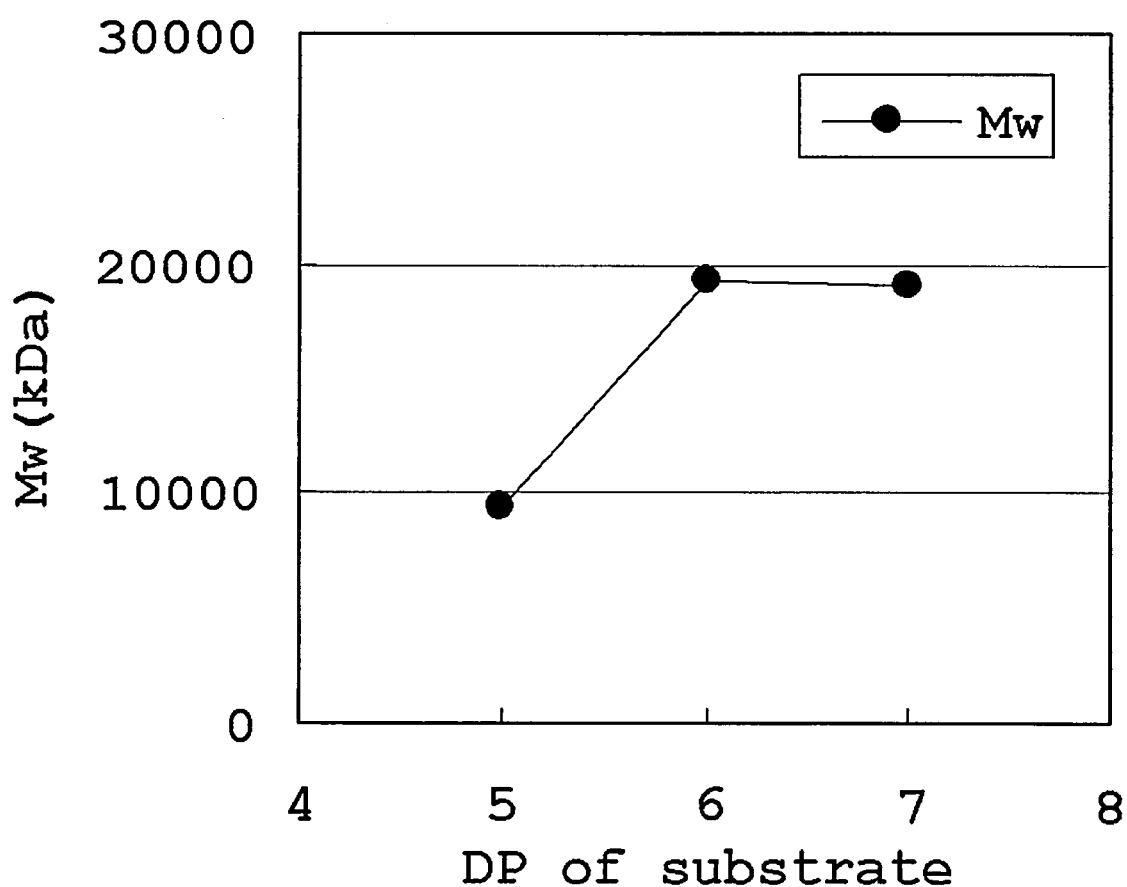
FIG. 8 is a graph showing the Mw of products obtained using a substrate (G5, G6 or G7) of various DP (degrees of polymerization).

A schematic drawing showing that amylose is produced from maltopentaose by 4-α-glucanotransferase, and glycogen is produced from amylose by BE is shown in FIG. 7. After the reaction, the molecular weight of the α-glucan produced was measured. The results are shown in the following Table 4 and FIG. 8. FIG. 8 shows Mw wherein BE was used in an amount of 80000 U/g substrate. When there were split peaks, only the peak of higher molecular weight was measured.

As a result, it was found that glycogen can be produced in a highly efficient manner from G5, G6 and G7 using 4-α-glucanotransferase together.

(3-2: Production of Glycogen Using *Bacillus stearothermophilus*-Derived BE and TaqMalQ A substrate (maltoheptaose (G7)) was dissolved in water, and water, an enzyme solution and a buffer were added to the substrate solution such that the reaction solution had the following composition, and the resulting mixture was reacted at 50° C. for 17 hours. The composition of the reaction solution: amount of *Bacillus stearothermophilus*-derived BE, 160000 U/g substrate; amount of TaqMalQ, 2.3 U/g substrate; concentration of substrate, 0.5%; concentration of potassium phosphate, 5 mM; pH 7.5.

After the reaction, the molecular weight of the α-glucan produced was measured. The results are shown in Table 4 below. In Table 4, the yield of glucan shows the total yield of glucans having a molecular weight of 10,000 or more, and the yield of glycogen shows the yield of glucans having a molecular weight of 1,000,000 or more (that is, glycogen).

As a result, it was found that even when *Bacillus stearothermophilus*-derived BE is used, glycogen can be produced in a highly efficient manner from G7 using 4-α-glucanotransferase together.

TABLE 4

| | Reaction conditions | | | | Product | | | | | | |
|---|---|---|---|---|---|---|---|---|---|---|---|
| | | | Amount of | Reaction | Average molecular weight | | | Yield of | Yield of | Weight fraction of each component (%) | | |
| Example | Enzyme | Substrate | BE (U/g substrate) | temperature (° C.) | Mw (kDa) | Mn (kDa) | Mw/Mn | glucan (%) | glycogen (%) | 10-500 (kDa) | 500-1,000 (kDa) | 1,000-2,500 (kDa) |
| 3-1 | Aq + MalQ | G5 | 40000 | 65 | 14330 | 4563 | 3.14 | 4.4 | 3.6 | — | — | — |
| 3-1 | Aq + MalQ | G5 | 80000 | 65 | 9364 | 1981 | 4.73 | 6.8 | 5.4 | — | — | — |
| 3-1 | Aq + MalQ | G5 | 160000 | 65 | 7108 | 2049 | 3.47 | 13.6 | 10.7 | 5.03 | 16.21 | 6.43 |
| 3-1 | Aq + MalQ | G6 | 40000 | 65 | 20250 | 15920 | 1.27 | 12.1 | 12.0 | — | — | — |
| 3-1 | Aq + MalQ | G6 | 80000 | 65 | 19180 | 11890 | 1.61 | 13.3 | 13.1 | — | — | — |
| 3-1 | Aq + MalQ | G6 | 160000 | 65 | 12890 | 6000 | 2.15 | 20.0 | 19.6 | — | 1.87 | 12.35 |
| 3-1 | Aq + MalQ | G7 | 40000 | 65 | 24370 | 21820 | 1.12 | 13.2 | 13.1 | — | — | — |
| 3-1 | Aq + MalQ | G7 | 80000 | 65 | 18950 | 9783 | 1.94 | 15.2 | 15.0 | — | — | — |
| 3-1 | Aq + MalQ | G7 | 160000 | 65 | 16410 | 7077 | 2.32 | 17.9 | 17.7 | 0.32 | 0.90 | 12.00 |
| 3-2 | Bst + MalQ | G7 | 160000 | 50 | 13150 | 7434 | 1.77 | 22.0 | 22.0 | 0.05 | 0.01 | 0.15 |

| | Reaction conditions | | | | Product Weight fraction of each component (%) | | | |
|---|---|---|---|---|---|---|---|---|
| Example | Enzyme | Substrate | Amount of BE (U/g substrate) | Reaction temperature (° C.) | 2,500-5,000 (kDa) | 5,000-10,000 (kDa) | 10,000-50,000 (kDa) | 50,000 or more (kDa) |
| 3-1 | Aq + MalQ | G5 | 40000 | 65 | — | — | — | — |
| 3-1 | Aq + MalQ | G5 | 80000 | 65 | — | — | — | — |
| 3-1 | Aq + MalQ | G5 | 160000 | 65 | 1.16 | 61.81 | 9.21 | 0.15 |
| 3-1 | Aq + MalQ | G6 | 40000 | 65 | — | — | — | — |
| 3-1 | Aq + MalQ | G6 | 80000 | 65 | — | — | — | — |
| 3-1 | Aq + MalQ | G6 | 160000 | 65 | 1.63 | 0.74 | 83.19 | 0.23 |
| 3-1 | Aq + MalQ | G7 | 40000 | 65 | — | — | — | — |

TABLE 4-continued

| | | | | | | | | |
|---|---|---|---|---|---|---|---|---|
| 3-1 | Aq + MalQ | G7 | 80000 | 65 | — | — | — | — |
| 3-1 | Aq + MalQ | G7 | 160000 | 65 | 4.56 | 1.01 | 80.75 | 0.46 |
| 3-2 | Bst + MalQ | G7 | 160000 | 50 | 25.03 | 32.63 | 40.28 | 1.85 |

Aq: *Aquifex aeolicus*-derived branching enzyme
Bst: *Bacillus stearothermophilus*-derived branching enzyme
MalQ: *Thermus aquaticus*-derived Taq MalQ
Mw: weight-average molecular weight
Mn: number-average molecular weight Example 4

Production of Glycogen Under Relatively Low Temperature Conditions

Amylose A (Mn 2900, manufactured by Nacalai Tesque) was dissolved in 1 N NaOH and then neutralized with HCl. Immediately thereafter, water, an enzyme solution and a buffer were added to the amylose solution such that the reaction solution had the following composition, and the resulting mixture was reacted at 30° C. for 16 hours. The composition of the reaction solution: amount of *Aquifex aeolicus*- or *Bacillus stearothermophilus*-derived BE, 80,000 U/g substrate; concentration of substrate, 2 wt %; concentration of potassium phosphate, 20 mM; pH 7.5.

After the reaction, the molecular weight of the α-glucan produced was measured. The results are shown in Table 5. In Table 5, the yield of glucan shows the total yield of glucans having a molecular weight of 10,000 or more, and the yield of glycogen shows the yield of glucans having a molecular weight of 1,000,000 or more (that is, glycogen).

As a result, it was confirmed that even when either thermostable BE is used or when the reaction temperature is 30° C., glycogen having an Mw of 1,000,000 or more can be produced from Amylose A. From this result, production of glycogen is considered not to be due to the high-temperature conditions of the reaction but due to the properties of the thermostable BE.

Comparative Example 1

Production of α-glucan using *Bacillus cereus*-Derived BE

Amylose A, or enzymatically synthesized amylose (AS-10 (Mn 10000; Mn 9100) or AS-320 (Mw 320000; Mn 290000)) was dissolved in 1 N NaOH and then neutralized with HCl. Immediately thereafter, water, an enzyme solution and a buffer were added to the amylose solution such that the reaction solution had the following composition, and the resulting mixture was reacted at 30° C. for 24 hours. The composition of the reaction solution: amount of *B. cereus*-derived BE, 40,000 U/g substrate; concentration of substrate, 0.5 wt %; concentration of potassium phosphate, 20 mM; pH 7.5. *B. cereus*-derived BE was prepared according to a method described in Nonpatent Document 9.

After the reaction, the reaction was terminated by heating in a boiling water bath for 10 minutes, and the resulting α-glucan was analyzed by the MALLS method. The results are shown in Table 6. In Table 6, the yield of glucan shows the total yield of glucans having a molecular weight of 10,000 or more, and the yield of glycogen shows the yield of glucans having a molecular weight of 1,000,000 or more (that is, glycogen).

When Amylose A was used as the substrate, no high molecular weight α-glucan could be detected. Which ever enzymatically synthesized amylose was used, glucans having a molecular weight of 10,000 to 500,000 accounted for almost 100% of the product, and no glucans having a molecular weight of 1,000,000 or more could be detected. The Mw of the product was 86900 when a substrate having an Mn of 9100 was used, and the Mw of the product was 61900 when a substrate having an Mn of 290000 was used. When the high molecular weight substrate was used, conversion of the substrate into a low-molecular compound occurred.

Further, after *B. cereus* BE was allowed to act similarly on amylose of various sizes in the range of Mn 4500 to 290000, the product was analyzed by gel filtration, revealing that the molecular weight of the major component was almost the same as in the experiment described above. That is, no high molecular weight α-glucan having a molecular weight greater than 1,000,000 could be obtained in any case.

Example 3B

Production of α-glucan by Allowing BE Alone to Act on Short Saccharide Chain Amylose A substrate (maltotetraose (G4), maltopentaose (G5), maltohexaose (G6) or maltoheptaose (G7)) was dissolved in water, and *Aquifex aeolicus*-derived BE was added, and the reaction solution was adjusted to have the concentration of substrate and the amount of BE shown in Table 7 below, adjusted to pH 7.5 with 10 mM potassium phosphate buffer, and reacted for 17 hours at the temperature shown in Table 7 below.

After the reaction, the molecular weight of the α-glucan produced was measured. The results are shown in Table 7 below. In Table 7, the yield of glycogen (%) shows the yield of glucans having a molecular weight of 1,000,000 or more (that is, glycogen).

As a result, it was found that when low molecular weight substrates G4 to G7 are used, glycogen can be synthesized.

Example 5

Production of Glycogen by Allowing BE and Pullulanase to Act on Starch

Cornstarch (manufactured by Wako Pure Chemical Industries, Ltd.) (2 wt %) was suspended in water and heated at 100° C. for 30 minutes, whereby the cornstarch was gelatinized. This mixture was cooled to 60° C., and pullulanase (5 U/g substrate; Kleistase, manufactured by Daiwa Kasei K.K.) was added thereto and reacted at 60° C. for 20 hours, thereby producing amylose, and then heated at 100° C. for 10 minutes thereby terminating the reaction. Thereafter, this solution was adjusted to pH 7.5 with 10 mM potassium phosphate buffer, and *Aquifex aeolicus*-derived BE was added in an amount of 20000 U/g substrate, and then reacted with BE at 65° C. for 20 hours.

After the reaction, the molecular weight of the α-glucan produced was measured. The results are shown in Table 8 below. In Table 8, the yield of glycogen (%) shows the yield of glucans having a molecular weight of 1,000,000 or more (that is, glycogen). As a result, cornstarch debranched with pullulanase, similar to cornstarch debranched with isoamylase, could produce glycogen.

TABLE 5

| | | | Reaction conditions | | | Product | | | | | | |
|---|---|---|---|---|---|---|---|---|---|---|---|---|
| | | | Amount of BE enzyme | Reaction | Average molecular weight | | | Yield of | Yield of | Weight fraction of each component (%) | | |
| Example | Enzyme | Substrate | (U/g substrate) | temperature (° C.) | Mw (kDa) | Mn (kDa) | Mw/Mn | glucan (%) | glycogen (%) | 10-500 (kDa) | 500-1,000 (kDa) | 1,000-2,500 (kDa) |
| 4 | Aq | Amylose A (Mn 2900) | 80000 | 30 | 12160 | 3559 | 3.42 | 11.0 | 10.0 | 5.17 | 4.14 | 3.51 |
| 4 | st | Amylose A (Mn 2900) | 80000 | 30 | 9076 | 5171 | 1.76 | 46.0 | 46.0 | 0.02 | 0.05 | 11.13 |

| | | | Reaction conditions | | Product Weight fraction of each component (%) | | | |
|---|---|---|---|---|---|---|---|---|
| Example | Enzyme | Substrate | Amount of BE enzyme (U/g substrate) | Reaction temperature (° C.) | 2,500-5,000 (kDa) | 5,000-10,000 (kDa) | 10,000-50,000 (kDa) | 50,000 or more (kDa) |
| 4 | Aq | Amylose A (Mn 2900) | 80000 | 30 | 3.57 | 2.15 | 80.85 | 0.62 |
| 4 | st | Amylose A (Mn 2900) | 80000 | 30 | 28.76 | 28.54 | 30.98 | 0.52 |

Aq: *Aquifex aeolicus*-derived branching enzyme
Bst: *Bacillus stearothermophilus*-derived branching enzyme
Mw: weight-average molecular weight
Mn: number-average molecular weight

TABLE 6

| | | Reaction conditions | | | Product | | | | |
|---|---|---|---|---|---|---|---|---|---|
| | | Concentration of substrate | Amount of BE (U/g | Reaction temperature | Average molecular weight | | | Yield of | Yield of |
| Comparative Example | Enzyme | (wt %) | substrate) | (° C.) | Mw (kDa) | Mn (kDa) | Mw/Mn | Glucan (%) | Glycogen (%) |
| 1 | Amylose A | 0.5 | 40000 | 30 | not detectable | | | 0 | 0 |
| 1 | AS-10 | 0.5 | 40000 | 30 | 86.9 | 78.1 | 1.11 | 51.0 | 0 |
| 1 | AS-320 | 0.5 | 40000 | 30 | 61.9 | 56.3 | 1.10 | 85.0 | 0 |

TABLE 7

| | | Reaction conditions | | | | Product | | | |
|---|---|---|---|---|---|---|---|---|---|
| | | Amount of BE (U/g | | Concentration of Substrate | Reaction temperature | Average molecular weight | | | Yield of |
| Example | Enzyme | substrate) | Substrate | (wt %) | (° C.) | Mw (kDa) | Mn (kDa) | Mw/Mn | Glycogen (%) |
| 3B | Aq | 40000 | G4 | 1 | 65 | 2010 | 160.6 | 12.52 | 5.7 |
| 3B | Aq | 40000 | G5 | 1 | 75 | 2216 | 375.2 | 5.91 | 5.2 |
| 3B | Aq | 40000 | G6 | 1 | 75 | 1859 | 338.1 | 5.50 | 4.2 |
| 3B | Aq | 20000 | G7 | 0.5 | 75 | 2125 | 160.4 | 13.25 | 2.1 |

Aq: *Aquifex aeolicus*-derived branching enzyme
Mw: weight-average molecular weight
Mn: number-average molecular weight

TABLE 8

| | Reaction conditions | | | Product | | | |
|---|---|---|---|---|---|---|---|
| | | | | Average molecular weight | | | |
| | | Amount of PUL (U/g | Amount of BE (U/g | Concentration of Substrate | Mw | Mn | | Yield of |
| Example | Enzyme | substrate) | substrate) | (wt %) | (kDa) | (kDa) | Mw/Mn | Glycogen (%) |
| 3 | Aq + PUL | 5 | 20000 | 2 | 3121 | 2726 | 1.14 | 34.9 |

Evaluation Example 1

Resistance to Degradation with Pullulanase

It is reported that α-glucan obtained using methods of the prior art by allowing BE to act on amylose is different from native glycogen in the point that it is easily degraded with pullulanase (Nonpatent Document 10).

Whether the glycogen produced by the method of the present invention, similar to native glycogen, was resistant to degradation with pullulanase was examined.

Cornstarch (manufactured by Wako Pure Chemical Industries, Ltd.) (1 wt %) was suspended in water and gelatinized in a jet cooker. The product was cooled to 40° C., and isoamylase (40000 U/g substrate, manufactured by Hayashibara Biochemical Labs., Inc.) was added and reacted at 40° C. for 6 hours to formamylose. Thereafter, this solution was adjusted to pH 7.5 with 3 mM phosphate buffer (pH 7.0) and 5 N NaOH, and *Aquifex aeolicus*-derived BE was added to be a concentration of 20000 U/g substrate and reacted at 65° C. for 19 hours to produce glycogen having a weight-average molecular weight of 9719 kDa. This glycogen, oyster-derived reagent glycogen (manufactured by Wako Pure Chemical Industries, Ltd.), waxy cornstarch (manufactured by Roquette) or cornstarch (manufactured by Wako Pure Chemical Industries, Ltd.) was dissolved in 1 N NaOH and neutralized with HCl. Immediately thereafter, *Bacillus brevis*-derived pullulanase (manufactured by Daiwa Kasei K.K.) was added, and the reaction solution was adjusted to have a concentration of substrate of 0.5 wt % and pullulanase (0, 2, 4, 16, 64, 256 U/g substrate) and adjusted to pH 5.0 with 10 mM sodium acetate buffer (pH5.0) and then reacted at 60° C. for 30 minutes.

Figure 9:
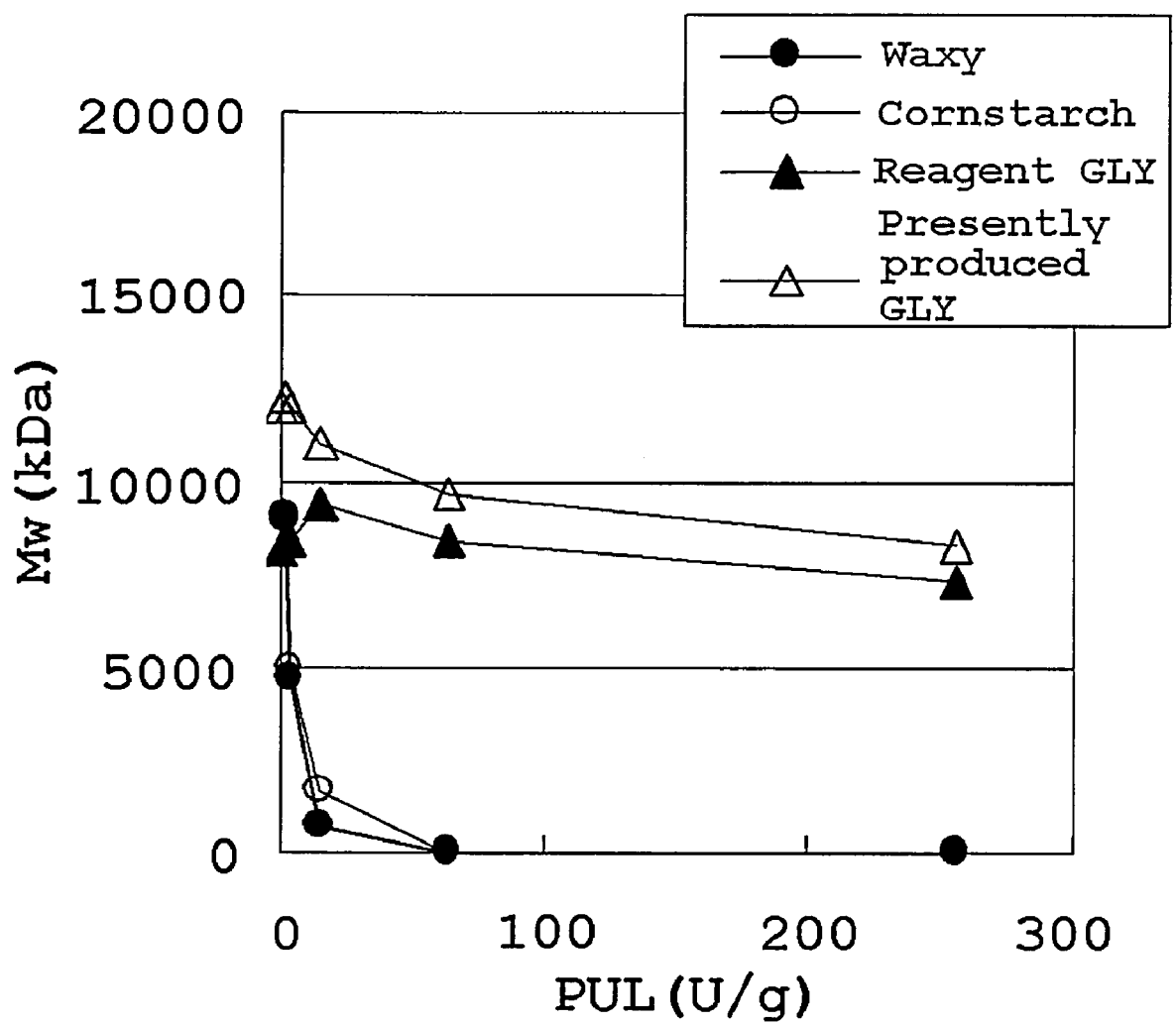
FIG. 9 is a graph showing the Mw of products after various amounts of pullulanase are allowed to act on glycogen produced by the present invention (open triangle, "presently produced GLY"), reagent glycogen (closed triangle, "reagent GLY"), waxy cornstarch (closed circle, "waxy") or cornstarch (open circle, "cornstarch").

After the reaction, the molecular weight of the product was measured. The result is shown in FIG. 9.

As a result, it was found that the starch was rapidly degraded, but the oyster-derived reagent glycogen (manufactured by Wako Pure Chemical Industries, Ltd.) and the glycogen according to the present production method were hardly degraded with pullulanase. Accordingly, it was confirmed that the glycogen produced by the method of the present invention has the same properties as those of native glycogen and can be said to be actual glycogen.

Evaluation Example 2

Resistance to Degradation with α-amylase

Glycogen is known to be scarcely degraded with pullulanase and was found to be extremely resistant to degradation with α-amylase according to the inventor's experiment. For example, waxy cornstarch and normal cornstarch were degraded to a molecular weight of 10,000 or less by treatment with 300 U/g human salivary α-amylase for 30 minutes, but the reagent oyster-derived glycogen was barely degraded under the same conditions.

Whether the glycogen produced by the method of the present invention was resistant to degradation with α-amylase, similar to native glycogen, was examined.

The glycogen prepared in Evaluation Example 1, oyster-derived reagent glycogen (manufactured by Wako Pure Chemical Industries, Ltd.), waxy cornstarch (manufactured by Roquette) or cornstarch (manufactured by Wako Pure Chemical Industries, Ltd.) was dissolved in 1 N NaOH and neutralized with HCl. Immediately thereafter, human salivary derived α-amylase (Type XIII-A manufactured by Sigma) was added, and the reaction solution was adjusted to have a concentration of substrate of 0.5 wt % and α-amylase (0, 5, 37.5, 75, 150, 300 U/g substrate) and adjusted to pH 7.0 with 20 mM potassium phosphate buffer (pH 7.0) and then reacted at 37° C. for 30 minutes.

Figure 10:
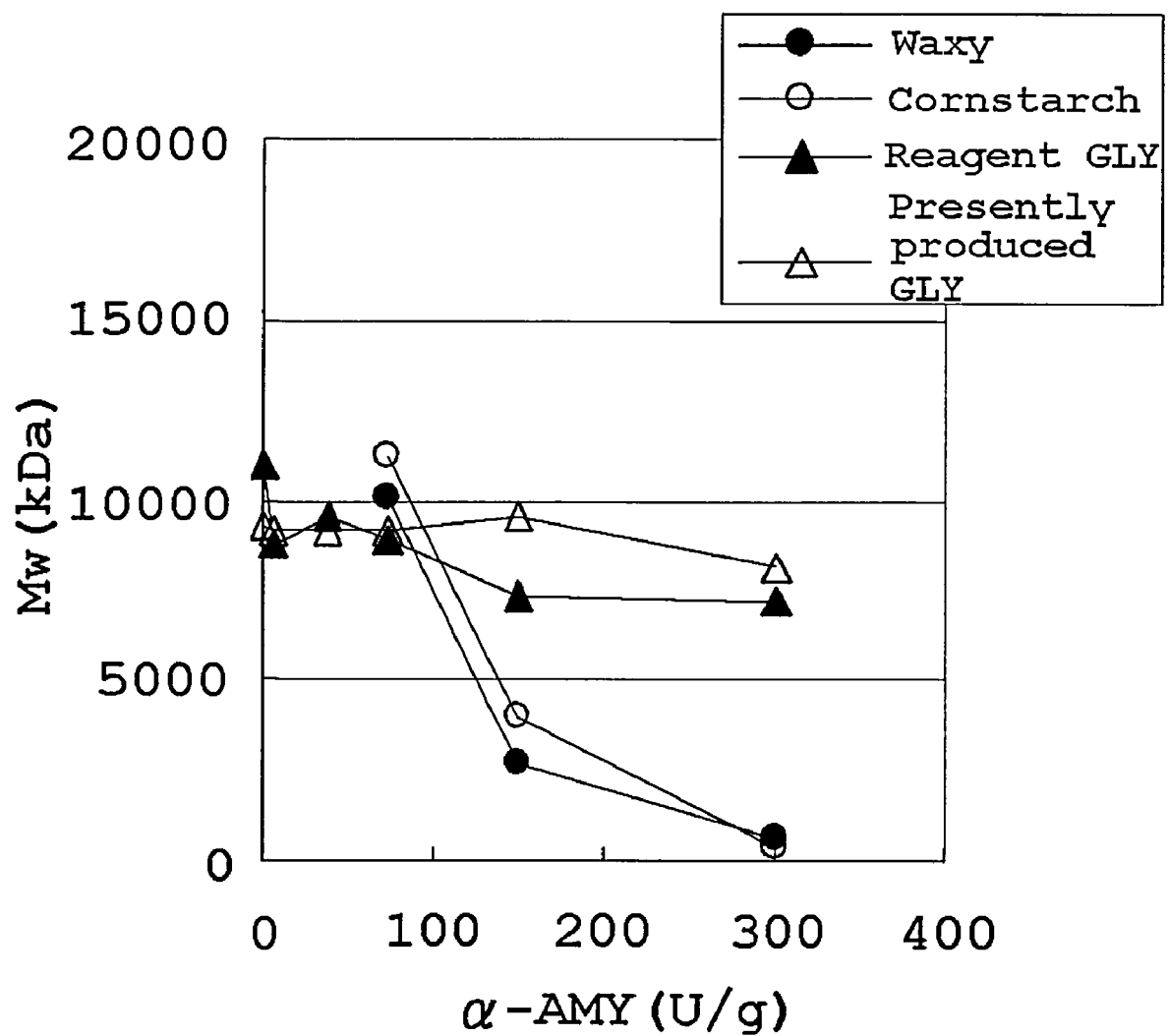
FIG. 10 is a graph showing the Mw of products after various amounts of α-amylase are allowed to act on glycogen produced by the present invention (open triangle, "presently produced GLY"), reagent glycogen (closed triangle, "reagent GLY"), waxy cornstarch (closed circle, "waxy") or cornstarch (open circle, "cornstarch").

After the reaction, the molecular weight of the product was measured. The result is shown in FIG. 10. When the amount of α-amylase was 0, 5, or 37.5 U/g substrate, the molecular weight of the starch could not be measured because the product could not be filtered.

As a result, it was found that the starch was rapidly degraded, but the oyster-derived reagent glycogen (manufactured by Wako Pure Chemical Industries, Ltd.) and the glycogen according to the present production method were barely degraded with α-amylase. Accordingly, it was confirmed that the glycogen produced by the method of the present invention has the same properties as those of native glycogen and can be said to be actual glycogen.

Example 6

Confirmation of Solubility of Glycogen

Amylose A (Mn 2900, manufactured by Nacalai Tesque) or Amylose AS10 (Mw 10,000 (Mn 9100), manufactured by Ajinoki Co., Ltd.) was dissolved in 1 N NaOH and then neutralized with HCl. Immediately thereafter, water, an enzyme solution and a buffer were added to the amylose solution such that the reaction solution had the following composition, and the resulting mixture was reacted at 70° C. for 24 hours. The composition of the reaction solution: *Aquifex aeolicus*-derived BE, 34,000 U/g substrate; concentration of substrate, 0.5 wt %; concentration of potassium phosphate, 20 mM; pH 7.5. The yield (%) of the glycogen obtained by this reaction was 10.1% (when Amylose A was used as the substrate) or 59.0% (when Amylose AS10 was used as the substrate).

The solubility was determined by the following method. The resulting glycogen was recovered by precipitation with ethanol, dried, and distilled water at room temperature (about 20° C.) was added to obtain a 2 mg/mL mixture. The mixture was stirred at room temperature for 30 seconds with a vortex mixer, and filtered through a 0.45 μm filter. The filtrate was measured for the amount of dissolved glycogen by the MALLS method.

Further, the pullulanase resistance and α-amylase resistance were determined by the following method. First, the glycogen recovered by precipitation with ethanol was suspended in water and completely dissolved by heating at 100° C. Treatment with pullulanase was carried out at 60° C. for 30 minutes using Kleistase (manufactured by Daiwa Kasei K.K.) in an amount of 256 U/g substrate. Treatment with α-amylase was carried out at 37° C. for 30 minutes using Type XIII-A (manufactured by Sigma) in an amount of 300 U/g substrate. After the reaction was terminated, the Mw of the glucans was calculated by the MALLS method. Resistance to pullulanase or α-amylase was evaluated by determining the ratio according to the following equation. That is, pullulanase resistance (%)=
  $\{(Mw_{after\ pullulanase\ treatment})/(Mw_{before\ treatment})\} \times 100$, and α-amylase resistance (%)=
  $\{(Mw_{after\ \alpha\text{-}amylase\ treatment})/(Mw_{before\ treatment})\} \times 100$.

The results are shown in Table 9 below.

TABLE 9

| | | Product | | | |
|---|---|---|---|---|---|
| Substrate | Mw (kDa) | Yield of Glycogen (%) | Solubility (%) | Resistance to Pullulanase (%) | Resistance to α-Amylase (%) |
| Amylose A | 9370 | 10.1 | 86.3 | 78.6 | 77.7 |
| Amylose AS10 | 20400 | 59.0 | 95.2 | 72.6 | 101 |

As a result, it was found that glycogen having high solubility, high resistance to pullulanase and high resistance to α-amylase, can be obtained by the method of the present invention.

Example 7

Improvement of Yield of Glycogen by Combined use of *Aquifex aeolicus* VF5-Derived BE and *Thermus aquaticus*-Derived 4-α-Glucanotransferase (TaqMalQ)

Example 7-1

Production of Glycogen by Allowing TaqMalQ and *Aquifex aeolicus*-Derived BE to Act on Amylose A Amylose A (Mn 2900, manufactured by Nacalai Tesque) was dissolved in 1 N NaOH and then neutralized with HCl. Immediately thereafter, water, an enzyme solution and a buffer were added to the amylose solution such that the reaction solution had the following composition, and the resulting mixture was reacted at 65° C. for 20 hours. The composition of the reaction solution: amount of *Aquifex aeolicus*-derived BE, 5000 or 20000 U/g substrate; amount of TaqMalQ, 5, 10, or 20 U/g substrate; concentration of substrate, 2 wt %; concentration of potassium phosphate, 20 mM; pH 7.5. The reaction conditions and analysis results of the product are shown in Table 10 below.

TABLE 10

| | Reaction conditions | | | | Product | | | |
|---|---|---|---|---|---|---|---|---|
| | | | | | | Average molecular weight | | |
| Example | Concentration of substrate (wt %) | Amount of BE (U/g substrate) | Amount of MalQ (U/g substrate) | Reaction temperature (° C.) | Mw (kDa) | Mn (kDa) | Mw/Mn | Yield of Glycogen (%) |
| 7-1 | 2 | 5000 | 0 | 65 | 10470 | 1262 | 8.30 | 5.1 |
| 7-1 | 2 | 5000 | 5 | 65 | 24520 | 23690 | 1.04 | 54.6 |
| 7-1 | 2 | 5000 | 10 | 65 | 27310 | 26480 | 1.03 | 51.2 |
| 7-1 | 2 | 5000 | 20 | 65 | 28630 | 27970 | 1.02 | 55.3 |
| 7-1 | 2 | 20000 | 0 | 65 | 21470 | 17560 | 1.22 | 7.5 |
| 7-1 | 2 | 20000 | 5 | 65 | 21090 | 20400 | 1.03 | 61.6 |
| 7-1 | 2 | 20000 | 10 | 65 | 23960 | 23150 | 1.03 | 59.3 |
| 7-1 | 2 | 20000 | 20 | 65 | 25480 | 24760 | 1.03 | 65.2 |

Substrate: Amylose A
BE: *Aquifex aeolicus*-derived BE
MalQ: *Thermus aquaticus*-derived 4-α-glucanotransferase It was thus found that glycogen having an Mw of 1000 kDa or more can be produced using *Aquifex aeolicus*-derived BE and TaqMalQ. It was revealed that by adding TaqMalQ, the yield of glycogen can be significantly improved.

Example 7-2

Production of Glycogen by Allowing TaqMalQ and *Aquifex aeolicus*-Derived BE to Act on Cornstarch Cornstarch (manufactured by Wako Pure Chemical Industries, Ltd.) (2 wt %) was suspended in water and heated at 100° C. for 30 minutes, whereby the cornstarch was gelatinized. This mixture was cooled to 40° C., and isoamylase (manufactured by Hayashibara Biochemical Labs., Inc.) in an amount of 5000 U/g substrate was added thereto and reacted at 40° C. for 20 hours, whereby amylose was produced. Thereafter, this solution was adjusted to pH 7.5 with 5 mM potassium phosphate buffer, and *Aquifex aeolicus*-derived BE (20000 U/g substrate) and TaqMalQ (0.1, 0.5, 1, 2, 3, 4, 5, 10 or 20 U/g substrate) were added and reacted at 65° C. for 20 hours. The reaction conditions and analysis results of the product are shown in Table 11 below.

TABLE 11

| | Reaction conditions | | | | | | | | Product | | | |
|---|---|---|---|---|---|---|---|---|---|---|---|---|
| | Concentration of | | Reaction | | Amount | Amount | | | Average molecular weight | | | Yield of Glycogen |
| | Substrate | Amount of IAM (U/g | tempera-ture | Reaction time | of BE (U/g | of MalQ (U/g | Reaction temperature | Reaction time | Mw | Mn | | (% theoretical |
| Example | (wt %) | substrate) | (° C.) | (hrs) | substrate) | substrate) | (° C.) | (hrs) | (kDa) | (kDa) | Mw/Mn | value) |
| 7-2 | 2 | 5000 | 40 | 20 | 20000 | 0 | 65 | 20 | 5601 | 4031 | 1.39 | 37.3 |
| 7-2 | 2 | 5000 | 40 | 20 | 20000 | 0.1 | 65 | 20 | 9191 | 7258 | 1.27 | 62.3 |
| 7-2 | 2 | 5000 | 40 | 20 | 20000 | 0.5 | 65 | 20 | 10100 | 8223 | 1.23 | 64.8 |
| 7-2 | 2 | 5000 | 40 | 20 | 20000 | 1 | 65 | 20 | 11010 | 9053 | 1.22 | 69.6 |
| 7-2 | 2 | 5000 | 40 | 20 | 20000 | 2 | 65 | 20 | 11550 | 9645 | 1.20 | 69.9 |
| 7-2 | 2 | 5000 | 40 | 20 | 20000 | 3 | 65 | 20 | 10380 | 8677 | 1.20 | 72.4 |
| 7-2 | 2 | 5000 | 40 | 20 | 20000 | 4 | 65 | 20 | 11860 | 10030 | 1.18 | 64.4 |
| 7-2 | 2 | 5000 | 40 | 20 | 20000 | 5 | 65 | 20 | 12080 | 10360 | 1.17 | 69.7 |
| 7-2 | 2 | 5000 | 40 | 20 | 20000 | 10 | 65 | 20 | 14230 | 12530 | 1.14 | 80.3 |
| 7-2 | 2 | 5000 | 40 | 20 | 20000 | 20 | 65 | 20 | 16940 | 14930 | 1.13 | 80.2 |

Substrate: cornstarch
IAM: *Pseudomonas amyloderamosa*-derived isoamylase
BE: *Aquifex aeolicus*-derived BE
MalQ: *Thermus aquaticus*-derived 4-α-glucanotransferase It was thus found that after isoamylase is allowed to act on cornstarch, glycogen having an Mw of 1000 kDa or more can be produced in a highly efficient manner using *Aquifex aeolicus*-derived BE and TaqMalQ.

Example 7-3

Production of Glycogen by Allowing TaqMalQ and *Aquifex aeolicus*-Derived BE to Act on Liquefied Debranched Cornstarch as the Substrate Cornstarch (manufactured by Wako Pure Chemical Industries, Ltd.) was suspended at a concentration of 6 wt % in water and liquefied to DE12 at 100° C. with α-amylase (manufactured by Daiwa Kasei K.K.). After the reaction was terminated, isoamylase (5000 U/g substrate, manufactured by Hayashibara Biochemical Labs., Inc.) was added thereto and reacted at 40° C. for 20 hours thereby effecting debranching. The Mn of the debranched product was about 600. This solution was adjusted to pH 7.5 with 5 mM potassium phosphate buffer, and *Aquifex aeolicus*-derived BE (5000 U/g substrate) and TaqMalQ (1 U/g substrate) were added and reacted at 65° C. for 20 hours, whereby glycogen having an Mw of 11360 kDa was obtained.

Example 8

Production of Glycogen using *Rhodothermus obamensis*-Derived BE

*Rhodothermus obamensis*-derived BE was allowed to act on Amylose A and AS-10 to produce glycogen. Specifically, Amylose A (Mn 2900, manufactured by Nacalai Tesque) or AS-10 (Mn 9100, manufactured by Ajinoki Co., Ltd.) was dissolved in 1 N NaOH and then neutralized with HCl. Immediately thereafter, water, an enzyme solution and a buffer were added to the amylose solution such that the reaction solution had the following composition, and the resulting mixture was reacted at 65° C. for 17 hours. The composition of the reaction solution: *Rhodothermus obamensis*-derived BE, 40,000 U/g substrate; concentration of substrate, 2 wt %; sodium acetate concentration, 40 mM; pH 6.0. The reaction conditions and analysis results of the product are shown in Table 12 below.

TABLE 12

| | | Reaction conditions | | | Product | | | |
|---|---|---|---|---|---|---|---|---|
| | | Concentration of | Amount of | Reaction | Average molecular weight | | | Yield of |
| Example | Substrate | substrate (wt %) | BE (U/g substrate) | temperature (° C.) | Mw (kDa) | Mn (kDa) | Mw/Mn | Glycogen (%) |
| 8 | Amylose A | 2 | 40000 | 65 | 10270 | 9399 | 1.09 | 48.6 |
| 8 | AS-10 | 2 | 40000 | 65 | 38100 | 35540 | 1.07 | 97.2 |

BE: *Rhodothermus obamensis*-derived BE

It was thus found that glycogen having an Mw of 1000 kDa or more can be produced in a highly efficient manner using *Rhodothermus obamensis*-derived BE.

Example 9

Production of Glycogen using *Bacillus caldovelox*-Derived BE

*Bacillus* caldovelox-derived BE was allowed to act on Amylose A and AS-10 to produce glycogen. Specifically, Amylose A (Mn 2900, manufactured by Nacalai Tesque) or AS-10 (Mn 9100, manufactured by Ajinoki Co., Ltd.) was dissolved in 1 N NaOH and then neutralized with HCl. Immediately thereafter, water, an enzyme solution and a buffer were added to the amylose solution such that the reaction solution had the following composition, and the resulting mixture was reacted at 55° C. for 16 hours. The composition of the reaction solution: amount of *Bacillus caldovelox*-derived BE, 20,000 U/g substrate; concentration of substrate, 2 wt %; concentration of Tris, 20 mM; pH7.0. The reaction conditions and analysis results of the product are shown in Table 13 below.

TABLE 13

| | | Reaction conditions | | | Product | | | |
| | | | | | Average molecular weight | | | |
| Example | Substrate | Concentration of substrate (wt %) | Amount of BE (U/g substrate) | Reaction temperature (° C.) | Mw (kDa) | Mn (kDa) | Mw/Mn | Yield of Glycogen (%) |
|---|---|---|---|---|---|---|---|---|
| 9 | Amylose A | 2 | 20000 | 55 | 7188 | 4948 | 1.45 | 4.9 |
| 9 | AS-10 | 2 | 20000 | 55 | 3733 | 2337 | 1.60 | 52.2 |

BE: *Bacillus caldovelox*-derived BE

It was thus found that glycogen having an Mw of 1000 kDa or more can be produced using *Bacillus caldovelox*-derived BE.

Example 10

Production of Glycogen using *Bacillus caldolyticus*-Derived BE

*Bacillus caldolyticus*-derived BE was allowed to act on Amylose A and AS-10 to produce glycogen. Specifically, Amylose A (Mn2900, manufactured by Nacalai Tesque) or AS-10 (Mn 9100, manufactured by Ajinoki Co., Ltd.) was dissolved in 1 N NaOH and then neutralized with HCl. Immediately thereafter, water, an enzyme solution and a buffer were added to the amylose solution such that the reaction solution had the following composition, and the resulting mixture was reacted at 45° C. for 16 hours. The composition of the reaction solution: amount of *Bacillus caldolyticus*-derived BE, 20,000 U/g substrate; concentration of substrate, 2 wt %; concentration of Tris, 20 mM; pH 7.0. The reaction conditions and analysis results of the product are shown in Table 14 below.

TABLE 14

| | | Reaction conditions | | | Product | | | |
| | | | | | Average molecular weight | | | |
| Example | Substrate | Concentration of substrate (wt %) | Amount of BE (U/g substrate) | Reaction temperature (° C.) | Mw (kDa) | Mn (kDa) | Mw/Mn | Yield of Glycogen (%) |
|---|---|---|---|---|---|---|---|---|
| 10 | Amylose A | 2 | 20000 | 45 | 6106 | 4278 | 1.43 | 7.6 |
| 10 | AS-10 | 2 | 20000 | 45 | 3450 | 2286 | 1.51 | 43.4 |

BE: *Bacillus caldolyticus*-derived BE

It was thus found that glycogen having an Mw of 1000 kDa or more can be produced using *Bacillus caldolyticus*-derived BE.

The present invention has been illustrated by reference to preferable embodiments of the invention as above, but it should not be construed that the present invention is limited to such embodiments. It is understood that the scope of the invention should be construed by only the claims. It is understood that from the description of specific preferred embodiments of the invention, those skilled in the art can carry out the equivalent scope on the basis of the description of the invention and technical common knowledge. It is understood that the disclosure of the patents, patent applications and documents cited in this specification should be incorporated herein by reference in their entirety as with the contents specifically described in this specification.

INDUSTRIAL APPLICABILITY

According to the present invention, there is provided a method of producing inexpensively highly branched and high molecular weight α-glucan having the same properties as those of native glycogen. The glycogen produced by the method of the present invention, similar to conventional native glycogen, can be utilized in a broad scope of applications. Native glycogen is utilized in various fields in industry. For example, the glycogen produced according to the method of the present invention can be expected to be useful as an immunostimulant, health food material and the like. The glycogen produced by the method of the present invention can also be expected for use in a cosmetic material, a food material (flavoring material), and other industrial materials. Uses of the glycogen produced by the method of the present invention can include, for example, a therapeutic agent for microbial infections, a humectant (for example, a cosmetic effective for improving the moisture retention of skin, a cosmetic for prevention of roughening of lips), a complex seasoning (for example, a complex seasoning having the taste of the eye of a scallop), an antitumor agent, an accelerator for formation of fermented milk, a colloid particle aggregate, a substance improving abrasion resistance of the hair surface, which influences ease in combing and luster of hair, a cell activator (an epidermal cell activator, a fibroblast growth stimulant, or the like), an ATP production accelerator, an agent for ameliorating skin aging symptoms such as wrinkles, an agent for ameliorating skin roughening, a surface treatment agent for fluorescent material, and a substrate for the synthesis of cyclic tetrasaccharide (CTS; cyclo{→6}-α-D-glcp-(1→3)-α-D-glcp-(1→6)-α-D-glcp-(1→3)-α-D-glcp-(1→}). Glycogen produced in the method of the present invention can be used in external preparations for skin (for example, skin lotion, emulsion, cream, essence, hair-growth medicine, hair growth tonic, mask, lip stick, lip cream, makeup base lotion, makeup base cream, foundation, eye color, cheek color, shampoo, rinse, hair liquid, hair tonic, permanent wave agent, hair color, treatment, bath agent, hand cream, leg cream, neck cream, body lotion, and the like) or in a solution for eyes.

According to the method of the present invention, glycogen can be obtained (similar to native glycogen) having high solubility and low degradation with pullulanase and α-amylase. This is considered to be due to the specific properties of BE (particularly, thermostable BE) having the ability to synthesize glycogen.

The low digestibility of the resulting glycogen with the enzymes mentioned above is important, for example, for exhibiting the immunostimulant activity of the glycogen, and thus the present invention is particularly useful.

The invention claimed is:

1. A method of producing glycogen comprising a step of:
allowing a branching enzyme having the ability to synthesize glycogen to act on a substrate in a solution to produce a glycogen, wherein the substrate is an α-glucan being linked mainly with α-1,4-glycosides bond and having a degree of polymerization of 4 or more;
wherein the substrate is debranched starch, debranched dextrin or enzymatically synthesized amylose;
the number-average molecular weight of saccharides in the solution before initiation of the reaction is more than 180 but not more than 150,000;
the weight-average molecular weight of the glycogen is 1,000,000 Da or more;
the weight-average molecular weight of the product produced by subjecting the glycogen to reaction with pullulanase in an amount of 50 U/g substrate at 60° C. C. for 30 minutes is 500,000 Da or more as analyzed by the MALLS method;
the weight-average molecular weight of the product produced by subjecting the glycogen to reaction with α-amylase in an amount of 300 U/g substrate at 37° C. for 30 minutes is 500,000 Da or more as analyzed by the MALLS method;
in the method, neither α-glucan phosphorylase nor glycogen synthase is used; and
wherein the branching enzyme comprises an amino acid sequence having at least about 95% identity with the amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16 and SEQ ID NO: 18.

2. The method according to claim 1, wherein (the branching enzyme activity of the branching enzyme)/(the amylopectin molecular-weight-decreasing activity of the branching enzyme) is 500 or less.

3. The method according to claim 1, wherein the branching enzyme is a thermostable branching enzyme.

4. The method according to claim 1, wherein the branching enzyme is derived from a thermophilic bacterium or mesophilic bacterium.

5. The method according to claim 1, wherein the branching enzyme is derived from a bacterium belonging to a genus selected from the group consisting of the genera *Aquifex, Rhodothermus, Bacillus, Thermosynechococcus* and *Escherichia*.

6. The method according to claim 1, wherein the branching enzyme is derived from a bacterium selected from the group consisting of *Aquifex aeolicus, Aquifex pyrophilus, Rhodothermus obamensis, Rhodothermus marinus, Bacillus stearothermophilus, Bacillus caldovelox, Bacillus thermocatenulatus, Bacillus caldolyticus, Bacillus flavothermus, Bacillus acidocaldarius, Bacillus caldotenax, Bacillus smithii, Thermosynechococcus elongatus* and *Escherichia coli*.

7. The method according to claim 1, wherein the branching enzyme is derived from a bacterium selected from the group consisting of *Aquifex aeolicus, Rhodothermus obamensis, Bacillus stearothermophilus, Bacillus caldovelox, Bacillus thermocatenulatus, Bacillus caldolyticus* and *Escherichia coli*.

8. The method according to claim 1, wherein the optimum reaction temperature of the branching enzyme is not less than 45° C. and no more than 90° C.

9. The method according to claim 1, wherein the number-average molecular weight of the saccharides in the solution before initiation of the reaction is greater than 180 and less than 4,000.

10. The method according to claim 1, wherein the number-average molecular weight of the saccharides in the solution before initiation of the reaction is 4,000 or more and less than 8,000, and the amount of the branching enzyme used and the reaction time are adjusted such that the product of the amount of the branching enzyme used and the reaction time becomes 25,000 U·hour/g substrate or more.

11. The method according to claim 1, wherein the number-average molecular weight of the saccharides in the solution before initiation of the reaction is 8,000 or more and less than 100,000, and the amount of the branching enzyme used and the reaction time are adjusted such that the product of the amount of the branching enzyme used and the reaction time becomes 40,000 U·hour/g substrate or more.

12. The method according to claim 1, wherein the number-average molecular weight of the saccharides in the solution before initiation of the reaction is 100,000 or more and 150,000 or less, and the amount of the branching enzyme used and the reaction time are adjusted such that the product of the amount of the branching enzyme used and the reaction time becomes 150,000 U·hour/g substrate or more.

13. The method according to claim 1, which further comprises a step of allowing a 4-α-glucanotransferase to act on α-glucan having a number-average molecular weight of greater than 180 and less than 1,500 to produce the substrate.

14. The method according to claim 13, wherein the 4-α-glucanotranferase is amylomaltase derived from *Thermus aquaticus*.

15. The method according to claim 13, wherein the α-glucan having the number-average molecular weight of greater than 180 and less than 1,500 contains a maltooligosaccharide having a degree of polymerization of 4 to 7.

16. The method according to claim 1, which further comprises a step of allowing a debranching enzyme to act on low-branched α-glucans having a number-average molecular weight of 500 or more to produce the substrate.

17. The method according to claim 1, wherein a 4-α-glucanotranferase is coexistent with the branching enzyme.

18. The method according to claim 17, wherein the 4-α-glucanotranferase is an amylomaltase derived from *Thermus aquaticus*.

19. The method according to claim 1, wherein the branching enzyme is encoded by a nucleic acid molecule which hybridizes under stringent condition with a nucleic acid molecule consisting of a base sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15 and SEQ ID NO: 17, wherein the stringent condition is a hybridization at 65° C. in a solution containing 50% formamide, 5×SSC (750 mM NaCl, 75 mM trisodium citrate), 50 mM sodium phosphate (pH 7.6), 5× Denhardt's solution (0.2% BSA, 0.2% Ficoll 400 and 0.2% polyvinyl pyrrolidone), 10% dextran sulfate, and 20 µg/ml denatured sheared salmon sperm DNA, and washing under the condition of 65° C. using a SSC (saline-sodium citrate) solution having a 0.1 to 2-fold concentration, and wherein the composition of the SSC solution having a 1-fold concentration is 150 mM sodium chloride, 15 mM sodium citrate.

20. The method according to claim 1, wherein the branching enzyme comprises an amino acid sequence having a deletion, a substitution, or an insertion of one or several amino acids compared to the amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16 and SEQ ID NO: 18.

21. The method according to claim 1, wherein the branching enzyme comprises an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16 and SEQ ID NO: 18.

* * * * *

SEQUENCE LISTING

```
<160> NUMBER OF SEQ ID NOS: 24

<210> SEQ ID NO 1
<211> LENGTH: 1893
<212> TYPE: DNA
<213> ORGANISM: Aquifex aeolicus
<220> FEATURE:
<221> NAME/KEY: CDS
<222> LOCATION: (1)..(1893)

<400> SEQUENCE: 1 atg aag aag ttc agt ctc atc agt gat tac gac gtt tac ctc ttt aag      48
Met Lys Lys Phe Ser Leu Ile Ser Asp Tyr Asp Val Tyr Leu Phe Lys
1               5                   10                  15 gag gga acg cac acg aga ctt tac gat aaa ctt ggc tcc cac gtt ata      96
Glu Gly Thr His Thr Arg Leu Tyr Asp Lys Leu Gly Ser His Val Ile
                20                  25                  30 gaa cta aac ggg aaa agg tat acc ttc ttt gcg gtt tgg gca ccc cac     144
Glu Leu Asn Gly Lys Arg Tyr Thr Phe Phe Ala Val Trp Ala Pro His
            35                  40                  45 gcg gat tac gta tca ctt ata ggc gat ttt aac gaa tgg gat aaa ggt     192
Ala Asp Tyr Val Ser Leu Ile Gly Asp Phe Asn Glu Trp Asp Lys Gly
        50                  55                  60 tct act ccc atg gta aag agg gag gac ggc tcc gga ata tgg gag gtt     240
Ser Thr Pro Met Val Lys Arg Glu Asp Gly Ser Gly Ile Trp Glu Val
65                  70                  75                  80 tta ctt gaa gga gac ctg act ggt tca aag tac aag tac ttt ata aag     288
```

```
Leu Leu Glu Gly Asp Leu Thr Gly Ser Lys Tyr Lys Tyr Phe Ile Lys
            85                  90                  95 aac ggg aat tac gaa gtt gat aag tcc gat ccc ttc gca ttt ttc tgt      336
Asn Gly Asn Tyr Glu Val Asp Lys Ser Asp Pro Phe Ala Phe Phe Cys
                100                 105                 110 gag caa ccc ccc gga aac gct tcc gta gtg tgg aag ctc aat tac agg      384
Glu Gln Pro Pro Gly Asn Ala Ser Val Val Trp Lys Leu Asn Tyr Arg
            115                 120                 125 tgg aac gac tcc gaa tac atg aaa aag agg aaa aga gta aac tca cac      432
Trp Asn Asp Ser Glu Tyr Met Lys Lys Arg Lys Arg Val Asn Ser His
        130                 135                 140 gac tcg cct ata tcc ata tac gaa gtt cac gtg ggt tct tgg agg aga      480
Asp Ser Pro Ile Ser Ile Tyr Glu Val His Val Gly Ser Trp Arg Arg
145                 150                 155                 160 gtt cca gaa gag gga aac aga ttt ttg agc tat agg gaa ctt gcc gaa      528
Val Pro Glu Glu Gly Asn Arg Phe Leu Ser Tyr Arg Glu Leu Ala Glu
                165                 170                 175 tac ctc cca tac tac gta aaa gag atg gga ttt act cac gtt gag ttc      576
Tyr Leu Pro Tyr Tyr Val Lys Glu Met Gly Phe Thr His Val Glu Phe
            180                 185                 190 tta ccc gtt atg gaa cat ccc ttt tac ggc tct tgg ggc tac cag ata      624
Leu Pro Val Met Glu His Pro Phe Tyr Gly Ser Trp Gly Tyr Gln Ile
        195                 200                 205 acg ggc tac ttc gct ccg act tcc aga tac gga act cct cag gac ttt      672
Thr Gly Tyr Phe Ala Pro Thr Ser Arg Tyr Gly Thr Pro Gln Asp Phe
    210                 215                 220 atg tac tta ata gac aaa ctt cat caa gaa ggg ata ggt gtg ata cta      720
Met Tyr Leu Ile Asp Lys Leu His Gln Glu Gly Ile Gly Val Ile Leu
225                 230                 235                 240 gac tgg gtt ccc tct cac ttt ccc acc gat gcc cac ggg ctc gca tac      768
Asp Trp Val Pro Ser His Phe Pro Thr Asp Ala His Gly Leu Ala Tyr
                245                 250                 255 ttt gac ggg act cac ctt tac gag tac gag gac tgg aga aag agg tgg      816
Phe Asp Gly Thr His Leu Tyr Glu Tyr Glu Asp Trp Arg Lys Arg Trp
            260                 265                 270 cat ccc gac tgg aac agc ttt gtt ttt gat tac gga aaa ccg gaa gtt      864
His Pro Asp Trp Asn Ser Phe Val Phe Asp Tyr Gly Lys Pro Glu Val
        275                 280                 285 cgc tcc ttt ctc ctg agt tct gcc cac ttc tgg ctc gac aag tac cac      912
Arg Ser Phe Leu Leu Ser Ser Ala His Phe Trp Leu Asp Lys Tyr His
    290                 295                 300 gca gac ggt ctc aga gtg gat gca gtt gct tca atg ctt tac cta gat      960
Ala Asp Gly Leu Arg Val Asp Ala Val Ala Ser Met Leu Tyr Leu Asp
305                 310                 315                 320 tac tct agg aaa gaa tgg gtt cca aac ata tac gga ggg aaa gaa aac     1008
Tyr Ser Arg Lys Glu Trp Val Pro Asn Ile Tyr Gly Gly Lys Glu Asn
                325                 330                 335 ctc gag gct ata gaa ttc ctc agg aag ttt aac gaa agc gtt tac aga     1056
Leu Glu Ala Ile Glu Phe Leu Arg Lys Phe Asn Glu Ser Val Tyr Arg
            340                 345                 350 aat ttt cca gac gtc cag aca ata gcg gag gaa tca aca gcc tgg cct     1104
Asn Phe Pro Asp Val Gln Thr Ile Ala Glu Glu Ser Thr Ala Trp Pro
        355                 360                 365 atg gtg tcc aga cct aca tac gtg ggg gga ctg gga ttt gga atg aag     1152
Met Val Ser Arg Pro Thr Tyr Val Gly Gly Leu Gly Phe Gly Met Lys
    370                 375                 380 tgg aat atg ggt tgg atg aac gac aca ctc ttt tac ttt tca aag gat     1200
Trp Asn Met Gly Trp Met Asn Asp Thr Leu Phe Tyr Phe Ser Lys Asp
385                 390                 395                 400
```

```
ccc atc tac agg aag tac cac cat gaa gtc ctc act ttc agt ata tgg     1248
Pro Ile Tyr Arg Lys Tyr His His Glu Val Leu Thr Phe Ser Ile Trp
                405                 410                 415 tac gct ttt tcc gag aac ttc gtc ctt cca cta tcc cac gat gaa gtt     1296
Tyr Ala Phe Ser Glu Asn Phe Val Leu Pro Leu Ser His Asp Glu Val
            420                 425                 430 gtt cac gga aag ggt tct ctg ata ggg aag atg cca gga gat tac tgg     1344
Val His Gly Lys Gly Ser Leu Ile Gly Lys Met Pro Gly Asp Tyr Trp
        435                 440                 445 cag aag ttt gca aac ctt aga gcc ctt ttc gga tac atg tgg gca cac     1392
Gln Lys Phe Ala Asn Leu Arg Ala Leu Phe Gly Tyr Met Trp Ala His
    450                 455                 460 cca ggg aaa aaa ctc ctc ttt atg ggg gga gag ttc gga cag ttt aag     1440
Pro Gly Lys Lys Leu Leu Phe Met Gly Gly Glu Phe Gly Gln Phe Lys
465                 470                 475                 480 gaa tgg gat cac gaa acg agt ctc gac tgg cac ctc ttg gaa tac cct     1488
Glu Trp Asp His Glu Thr Ser Leu Asp Trp His Leu Leu Glu Tyr Pro
                485                 490                 495 tct cac aga ggt att cag aga tta gtt aag gac tta aac gaa gtt tac     1536
Ser His Arg Gly Ile Gln Arg Leu Val Lys Asp Leu Asn Glu Val Tyr
            500                 505                 510 agg agg gaa aag gct ttg cac gaa acg gat ttt tca cct gag ggc ttt     1584
Arg Arg Glu Lys Ala Leu His Glu Thr Asp Phe Ser Pro Glu Gly Phe
        515                 520                 525 gag tgg gta gac ttc cac gac tgg gaa aag agc gtt ata tcc ttc ttg     1632
Glu Trp Val Asp Phe His Asp Trp Glu Lys Ser Val Ile Ser Phe Leu
    530                 535                 540 aga aag gac aaa agc ggt aag gaa att ata ctc gta gtt tgc aac ttc     1680
Arg Lys Asp Lys Ser Gly Lys Glu Ile Ile Leu Val Val Cys Asn Phe
545                 550                 555                 560 aca ccc gtt ccg aga tac gat tac agg gta ggt gta ccg aaa ggc gga     1728
Thr Pro Val Pro Arg Tyr Asp Tyr Arg Val Gly Val Pro Lys Gly Gly
                565                 570                 575 tac tgg agg gag ata atg aat acc gat gca aag gag tac tgg ggc tcc     1776
Tyr Trp Arg Glu Ile Met Asn Thr Asp Ala Lys Glu Tyr Trp Gly Ser
            580                 585                 590 gga atg gga aat ctg ggt gga aaa gag gct gat aaa atc ccg tgg cac     1824
Gly Met Gly Asn Leu Gly Gly Lys Glu Ala Asp Lys Ile Pro Trp His
        595                 600                 605 gga aga aaa ttc tca ctt tca ctt acc ctg cct ccc ctt tcc gtg atc     1872
Gly Arg Lys Phe Ser Leu Ser Leu Thr Leu Pro Pro Leu Ser Val Ile
    610                 615                 620 tat tta aag cac gaa gga tga                                         1893
Tyr Leu Lys His Glu Gly
625                 630

<210> SEQ ID NO 2
<211> LENGTH: 630
<212> TYPE: PRT
<213> ORGANISM: Aquifex aeolicus

<400> SEQUENCE: 2

Met Lys Lys Phe Ser Leu Ile Ser Asp Tyr Asp Val Tyr Leu Phe Lys
1               5                   10                  15

Glu Gly Thr His Thr Arg Leu Tyr Asp Lys Leu Gly Ser His Val Ile
            20                  25                  30

Glu Leu Asn Gly Lys Arg Tyr Thr Phe Phe Ala Val Trp Ala Pro His
        35                  40                  45

Ala Asp Tyr Val Ser Leu Ile Gly Asp Phe Asn Glu Trp Asp Lys Gly
    50                  55                  60
```

```
Ser Thr Pro Met Val Lys Arg Glu Asp Gly Ser Gly Ile Trp Glu Val
 65                  70                  75                  80

Leu Leu Glu Gly Asp Leu Thr Gly Ser Lys Tyr Lys Tyr Phe Ile Lys
                 85                  90                  95

Asn Gly Asn Tyr Glu Val Asp Lys Ser Asp Pro Phe Ala Phe Phe Cys
            100                 105                 110

Glu Gln Pro Pro Gly Asn Ala Ser Val Val Trp Lys Leu Asn Tyr Arg
        115                 120                 125

Trp Asn Asp Ser Glu Tyr Met Lys Lys Arg Lys Arg Val Asn Ser His
    130                 135                 140

Asp Ser Pro Ile Ser Ile Tyr Glu Val His Val Gly Ser Trp Arg Arg
145                 150                 155                 160

Val Pro Glu Glu Gly Asn Arg Phe Leu Ser Tyr Arg Glu Leu Ala Glu
                165                 170                 175

Tyr Leu Pro Tyr Tyr Val Lys Glu Met Gly Phe Thr His Val Glu Phe
            180                 185                 190

Leu Pro Val Met Glu His Pro Phe Tyr Gly Ser Trp Gly Tyr Gln Ile
        195                 200                 205

Thr Gly Tyr Phe Ala Pro Thr Ser Arg Tyr Gly Thr Pro Gln Asp Phe
    210                 215                 220

Met Tyr Leu Ile Asp Lys Leu His Gln Glu Gly Ile Gly Val Ile Leu
225                 230                 235                 240

Asp Trp Val Pro Ser His Phe Pro Thr Asp Ala His Gly Leu Ala Tyr
                245                 250                 255

Phe Asp Gly Thr His Leu Tyr Glu Tyr Glu Asp Trp Arg Lys Arg Trp
            260                 265                 270

His Pro Asp Trp Asn Ser Phe Val Phe Asp Tyr Gly Lys Pro Glu Val
        275                 280                 285

Arg Ser Phe Leu Leu Ser Ser Ala His Phe Trp Leu Asp Lys Tyr His
    290                 295                 300

Ala Asp Gly Leu Arg Val Asp Ala Val Ala Ser Met Leu Tyr Leu Asp
305                 310                 315                 320

Tyr Ser Arg Lys Glu Trp Val Pro Asn Ile Tyr Gly Gly Lys Glu Asn
                325                 330                 335

Leu Glu Ala Ile Glu Phe Leu Arg Lys Phe Asn Glu Ser Val Tyr Arg
            340                 345                 350

Asn Phe Pro Asp Val Gln Thr Ile Ala Glu Glu Ser Thr Ala Trp Pro
        355                 360                 365

Met Val Ser Arg Pro Thr Tyr Val Gly Gly Leu Gly Phe Gly Met Lys
    370                 375                 380

Trp Asn Met Gly Trp Met Asn Asp Thr Leu Phe Tyr Phe Ser Lys Asp
385                 390                 395                 400

Pro Ile Tyr Arg Lys Tyr His His Glu Val Leu Thr Phe Ser Ile Trp
                405                 410                 415

Tyr Ala Phe Ser Glu Asn Phe Val Leu Pro Leu Ser His Asp Glu Val
            420                 425                 430

Val His Gly Lys Gly Ser Leu Ile Gly Lys Met Pro Gly Asp Tyr Trp
        435                 440                 445

Gln Lys Phe Ala Asn Leu Arg Ala Leu Phe Gly Tyr Met Trp Ala His
    450                 455                 460

Pro Gly Lys Lys Leu Leu Phe Met Gly Gly Glu Phe Gly Gln Phe Lys
465                 470                 475                 480
```

```
Glu Trp Asp His Glu Thr Ser Leu Asp Trp His Leu Glu Tyr Pro
            485                 490                 495

Ser His Arg Gly Ile Gln Arg Leu Val Lys Asp Leu Asn Glu Val Tyr
            500                 505                 510

Arg Arg Glu Lys Ala Leu His Glu Thr Asp Phe Ser Pro Glu Gly Phe
            515                 520                 525

Glu Trp Val Asp Phe His Asp Trp Glu Lys Ser Val Ile Ser Phe Leu
            530                 535                 540

Arg Lys Asp Lys Ser Gly Lys Glu Ile Ile Leu Val Val Cys Asn Phe
545                 550                 555                 560

Thr Pro Val Pro Arg Tyr Asp Tyr Arg Val Gly Val Pro Lys Gly Gly
                565                 570                 575

Tyr Trp Arg Glu Ile Met Asn Thr Asp Ala Lys Glu Tyr Trp Gly Ser
            580                 585                 590

Gly Met Gly Asn Leu Gly Gly Lys Glu Ala Asp Lys Ile Pro Trp His
            595                 600                 605

Gly Arg Lys Phe Ser Leu Ser Leu Thr Leu Pro Pro Leu Ser Val Ile
            610                 615                 620

Tyr Leu Lys His Glu Gly
625                 630

<210> SEQ ID NO 3
<211> LENGTH: 1866
<212> TYPE: DNA
<213> ORGANISM: Rhodothermus obamensis
<220> FEATURE:
<221> NAME/KEY: CDS
<222> LOCATION: (1)..(1866)

<400> SEQUENCE: 3
```

```
atg agc tgg ctc acg gaa gaa gac atc cgg cgc tgg gaa agc ggt acg      48
Met Ser Trp Leu Thr Glu Glu Asp Ile Arg Arg Trp Glu Ser Gly Thr
1               5                   10                  15 ttc tac gac agt tac cga aag ctg ggc gcc cat ccc gac gac gaa ggc      96
Phe Tyr Asp Ser Tyr Arg Lys Leu Gly Ala His Pro Asp Asp Glu Gly
                20                  25                  30 acc tgg ttc tgc gtc tgg gcg ccg cat gcc gat ggc gtc tcg gtg ctc     144
Thr Trp Phe Cys Val Trp Ala Pro His Ala Asp Gly Val Ser Val Leu
            35                  40                  45 gga gcg ttc aac gac tgg aat ccg gag gcc aac ccg ctg gag cgc tac     192
Gly Ala Phe Asn Asp Trp Asn Pro Glu Ala Asn Pro Leu Glu Arg Tyr
        50                  55                  60 ggc ggc ggc ctg tgg gcc ggt tac gta ccg gga gcg cgc ccg ggc cac     240
Gly Gly Gly Leu Trp Ala Gly Tyr Val Pro Gly Ala Arg Pro Gly His
65                  70                  75                  80 acc tac aag tat cgc atc cgg cac ggc ttc tat cag gcc gac aag acg     288
Thr Tyr Lys Tyr Arg Ile Arg His Gly Phe Tyr Gln Ala Asp Lys Thr
                85                  90                  95 gat ccc tac gcc ttc gcc atg gag ccg cct acc ggc agt ccc atc gaa     336
Asp Pro Tyr Ala Phe Ala Met Glu Pro Pro Thr Gly Ser Pro Ile Glu
                100                 105                 110 ggg ctg gcc tcc atc atc acg cgg ctc gac tac acc tgg cac gac gac     384
Gly Leu Ala Ser Ile Ile Thr Arg Leu Asp Tyr Thr Trp His Asp Asp
            115                 120                 125 gaa tgg atg cgg cgc cgg aag ggt ccg gcc agc ctt tac gag ccg gtt     432
Glu Trp Met Arg Arg Arg Lys Gly Pro Ala Ser Leu Tyr Glu Pro Val
        130                 135                 140 tcc atc tac gag gta cat ctg ggc tcc tgg cgt cac aaa cgg ccc ggc     480
Ser Ile Tyr Glu Val His Leu Gly Ser Trp Arg His Lys Arg Pro Gly
```

-continued

| | | |
|---|---|---|
| 145 | 150 | 155 | 160 |

| | | |
|---|---|
| gag tcc ttc tct tac cgg gag att gcc gag ccg ctg gcc gac tac gtg<br>Glu Ser Phe Ser Tyr Arg Glu Ile Ala Glu Pro Leu Ala Asp Tyr Val<br>165                              170                            175 | 528 |
| cag gag atg ggc ttc acg cac gtg gag ctg ctc ccc gtc atg gaa cat<br>Gln Glu Met Gly Phe Thr His Val Glu Leu Leu Pro Val Met Glu His<br>              180                            185                            190 | 576 |
| ccc tac tac ggc tcc tgg ggc tat cag gtg gtg ggc tac tac gcc cca<br>Pro Tyr Tyr Gly Ser Trp Gly Tyr Gln Val Val Gly Tyr Tyr Ala Pro<br>              195                            200                            205 | 624 |
| acg ttt cgc tac gga tca ccc cag gac ctg atg tac ctg atc gac tac<br>Thr Phe Arg Tyr Gly Ser Pro Gln Asp Leu Met Tyr Leu Ile Asp Tyr<br>210                              215                            220 | 672 |
| ctg cac cag cgc ggc atc ggc gtc atc ctc gac tgg gtc ccg agc cac<br>Leu His Gln Arg Gly Ile Gly Val Ile Leu Asp Trp Val Pro Ser His<br>225                              230                            235                            240 | 720 |
| ttt gcg gcc gat ccc cag gga ctg gtt ttc ttc gac ggg acc aca ctc<br>Phe Ala Ala Asp Pro Gln Gly Leu Val Phe Phe Asp Gly Thr Thr Leu<br>              245                            250                            255 | 768 |
| ttc gaa tac gac gat ccc aag atg cgc tat cac cct gac tgg ggt acg<br>Phe Glu Tyr Asp Asp Pro Lys Met Arg Tyr His Pro Asp Trp Gly Thr<br>              260                            265                            270 | 816 |
| tat gtg ttc gat tac aac aag ccg ggc gta cgc aac ttt ctg att tcc<br>Tyr Val Phe Asp Tyr Asn Lys Pro Gly Val Arg Asn Phe Leu Ile Ser<br>275                              280                            285 | 864 |
| aac gca ctt ttc tgg ctc gaa aag tac cac gtc gac ggg ctg cgc gtc<br>Asn Ala Leu Phe Trp Leu Glu Lys Tyr His Val Asp Gly Leu Arg Val<br>              290                            295                            300 | 912 |
| gat gcg gtg gct tct atg ctc tac cgg gac tac tca cgc aag gag tgg<br>Asp Ala Val Ala Ser Met Leu Tyr Arg Asp Tyr Ser Arg Lys Glu Trp<br>305                              310                            315                            320 | 960 |
| aca ccc aac atc ttc ggc ggc cgt gaa aac ctg gag gcc att gat ttc<br>Thr Pro Asn Ile Phe Gly Gly Arg Glu Asn Leu Glu Ala Ile Asp Phe<br>              325                            330                            335 | 1008 |
| atc aag aaa ttc aac gaa acg gtc tac ctg cac ttc ccc gag gcc atg<br>Ile Lys Lys Phe Asn Glu Thr Val Tyr Leu His Phe Pro Glu Ala Met<br>                      340                            345                            350 | 1056 |
| acg atc gcc gag gag tcg acg gcc tgg ccc ggc gtg tcg gcc ccc acc<br>Thr Ile Ala Glu Glu Ser Thr Ala Trp Pro Gly Val Ser Ala Pro Thr<br>355                              360                            365 | 1104 |
| tac aac aac ggt ctg ggc ttc ctc tac aag tgg aac atg ggc tgg atg<br>Tyr Asn Asn Gly Leu Gly Phe Leu Tyr Lys Trp Asn Met Gly Trp Met<br>370                              375                            380 | 1152 |
| cac gac acg ctg gac tac atc cag cgc gat ccc atc tac cgc aag tat<br>His Asp Thr Leu Asp Tyr Ile Gln Arg Asp Pro Ile Tyr Arg Lys Tyr<br>385                              390                            395                            400 | 1200 |
| cac cac gac gag ctg acc ttc tcg ctc tgg tac gcc ttt tcg gag cac<br>His His Asp Glu Leu Thr Phe Ser Leu Trp Tyr Ala Phe Ser Glu His<br>              405                            410                            415 | 1248 |
| tac gtc ctg ccg ctc tcg cac gac gag gtg gtg cac ggc aag ggc tcg<br>Tyr Val Leu Pro Leu Ser His Asp Glu Val Val His Gly Lys Gly Ser<br>                      420                            425                            430 | 1296 |
| ctc tgg ggt aaa atg ccc ggc gac gac tgg cag aag gca gcc aac ttg<br>Leu Trp Gly Lys Met Pro Gly Asp Asp Trp Gln Lys Ala Ala Asn Leu<br>435                              440                            445 | 1344 |
| cgc ctg ctc ttt ggc cac atg tgg ggc cat ccg ggc aaa aaa ctg ctc<br>Arg Leu Leu Phe Gly His Met Trp Gly His Pro Gly Lys Lys Leu Leu<br>450                              455                            460 | 1392 |
| ttc atg ggc ggc gag ttc ggc cag cac cac gag tgg aac cac gac acg | 1440 |

```
Phe Met Gly Gly Glu Phe Gly Gln His His Glu Trp Asn His Asp Thr
465                 470                 475                 480 cag ctc gaa tgg cac ctg ctg gac cag ccc tac cat cga ggt att cag      1488
Gln Leu Glu Trp His Leu Leu Asp Gln Pro Tyr His Arg Gly Ile Gln
                485                 490                 495 ctg tgg gtg tgc gat ctg aac cac ctc tac cgt acg aat ccg gcc ctc      1536
Leu Trp Val Cys Asp Leu Asn His Leu Tyr Arg Thr Asn Pro Ala Leu
                500                 505                 510 tgg cac gac gga ccg gaa ggg ttc gag tgg atc gac ttc agc gac cgc      1584
Trp His Asp Gly Pro Glu Gly Phe Glu Trp Ile Asp Phe Ser Asp Arg
                515                 520                 525 gac cag agc gtg atc tgt tac ctg cgc aag aat gcc ggc cgc atg ctg      1632
Asp Gln Ser Val Ile Cys Tyr Leu Arg Lys Asn Ala Gly Arg Met Leu
        530                 535                 540 ctg ttc gtg ctg aac ttt acg ccc gtg cca cgc gag cac tac cgc gtg      1680
Leu Phe Val Leu Asn Phe Thr Pro Val Pro Arg Glu His Tyr Arg Val
545                 550                 555                 560 ggc gtg ccg atc ggt ggc ccc tgg cac gag gtg ctc aac agc gac gcg      1728
Gly Val Pro Ile Gly Gly Pro Trp His Glu Val Leu Asn Ser Asp Ala
                565                 570                 575 gtg gcc tac ggc ggg agc ggg atg ggc aac ttc ggc cgc gtc gag gcg      1776
Val Ala Tyr Gly Gly Ser Gly Met Gly Asn Phe Gly Arg Val Glu Ala
                580                 585                 590 gtg ccc gag tcc tgg cac ggc cgc ccc ttc cac tta gag ctg acg ctt      1824
Val Pro Glu Ser Trp His Gly Arg Pro Phe His Leu Glu Leu Thr Leu
                595                 600                 605 ccc ccg ctg gcc gcc ctc atc ctg gag ccg gag cac ggg tag              1866
Pro Pro Leu Ala Ala Leu Ile Leu Glu Pro Glu His Gly
        610                 615                 620

<210> SEQ ID NO 4
<211> LENGTH: 621
<212> TYPE: PRT
<213> ORGANISM: Rhodothermus obamensis

<400> SEQUENCE: 4

Met Ser Trp Leu Thr Glu Glu Asp Ile Arg Arg Trp Glu Ser Gly Thr
1               5                   10                  15

Phe Tyr Asp Ser Tyr Arg Lys Leu Gly Ala His Pro Asp Asp Glu Gly
                20                  25                  30

Thr Trp Phe Cys Val Trp Ala Pro His Ala Asp Gly Val Ser Val Leu
            35                  40                  45

Gly Ala Phe Asn Asp Trp Asn Pro Glu Ala Asn Pro Leu Glu Arg Tyr
        50                  55                  60

Gly Gly Gly Leu Trp Ala Gly Tyr Val Pro Gly Ala Arg Pro Gly His
65                  70                  75                  80

Thr Tyr Lys Tyr Arg Ile Arg His Gly Phe Tyr Gln Ala Asp Lys Thr
                85                  90                  95

Asp Pro Tyr Ala Phe Ala Met Glu Pro Pro Thr Gly Ser Pro Ile Glu
                100                 105                 110

Gly Leu Ala Ser Ile Ile Thr Arg Leu Asp Tyr Thr Trp His Asp Asp
            115                 120                 125

Glu Trp Met Arg Arg Arg Lys Gly Pro Ala Ser Leu Tyr Glu Pro Val
        130                 135                 140

Ser Ile Tyr Glu Val His Leu Gly Ser Trp Arg His Lys Arg Pro Gly
145                 150                 155                 160

Glu Ser Phe Ser Tyr Arg Glu Ile Ala Glu Pro Leu Ala Asp Tyr Val
                165                 170                 175
```

-continued

```
Gln Glu Met Gly Phe Thr His Val Glu Leu Leu Pro Val Met Glu His
            180                 185                 190

Pro Tyr Tyr Gly Ser Trp Gly Tyr Gln Val Val Gly Tyr Tyr Ala Pro
            195                 200                 205

Thr Phe Arg Tyr Gly Ser Pro Gln Asp Leu Met Tyr Leu Ile Asp Tyr
            210                 215                 220

Leu His Gln Arg Gly Ile Gly Val Ile Leu Asp Trp Val Pro Ser His
225                 230                 235                 240

Phe Ala Ala Asp Pro Gln Gly Leu Val Phe Phe Asp Gly Thr Thr Leu
                245                 250                 255

Phe Glu Tyr Asp Asp Pro Lys Met Arg Tyr His Pro Asp Trp Gly Thr
                260                 265                 270

Tyr Val Phe Asp Tyr Asn Lys Pro Gly Val Arg Asn Phe Leu Ile Ser
                275                 280                 285

Asn Ala Leu Phe Trp Leu Glu Lys Tyr His Val Asp Gly Leu Arg Val
            290                 295                 300

Asp Ala Val Ala Ser Met Leu Tyr Arg Asp Tyr Ser Arg Lys Glu Trp
305                 310                 315                 320

Thr Pro Asn Ile Phe Gly Gly Arg Glu Asn Leu Glu Ala Ile Asp Phe
                325                 330                 335

Ile Lys Lys Phe Asn Glu Thr Val Tyr Leu His Phe Pro Glu Ala Met
                340                 345                 350

Thr Ile Ala Glu Glu Ser Thr Ala Trp Pro Gly Val Ser Ala Pro Thr
            355                 360                 365

Tyr Asn Asn Gly Leu Gly Phe Leu Tyr Lys Trp Asn Met Gly Trp Met
            370                 375                 380

His Asp Thr Leu Asp Tyr Ile Gln Arg Asp Pro Ile Tyr Arg Lys Tyr
385                 390                 395                 400

His His Asp Glu Leu Thr Phe Ser Leu Trp Tyr Ala Phe Ser Glu His
                405                 410                 415

Tyr Val Leu Pro Leu Ser His Asp Glu Val Val His Gly Lys Gly Ser
                420                 425                 430

Leu Trp Gly Lys Met Pro Gly Asp Asp Trp Gln Lys Ala Ala Asn Leu
            435                 440                 445

Arg Leu Leu Phe Gly His Met Trp Gly His Pro Gly Lys Lys Leu Leu
            450                 455                 460

Phe Met Gly Gly Glu Phe Gly Gln His His Glu Trp Asn His Asp Thr
465                 470                 475                 480

Gln Leu Glu Trp His Leu Leu Asp Gln Pro Tyr His Arg Gly Ile Gln
                485                 490                 495

Leu Trp Val Cys Asp Leu Asn His Leu Tyr Arg Thr Asn Pro Ala Leu
            500                 505                 510

Trp His Asp Gly Pro Glu Gly Phe Glu Trp Ile Asp Phe Ser Asp Arg
            515                 520                 525

Asp Gln Ser Val Ile Cys Tyr Leu Arg Lys Asn Ala Gly Arg Met Leu
530                 535                 540

Leu Phe Val Leu Asn Phe Thr Pro Val Pro Arg Glu His Tyr Arg Val
545                 550                 555                 560

Gly Val Pro Ile Gly Gly Pro Trp His Glu Val Leu Asn Ser Asp Ala
                565                 570                 575

Val Ala Tyr Gly Gly Ser Gly Met Gly Asn Phe Gly Arg Val Glu Ala
            580                 585                 590
```

Val Pro Glu Ser Trp His Gly Arg Pro Phe His Leu Glu Leu Thr Leu
        595                 600                 605

Pro Pro Leu Ala Ala Leu Ile Leu Glu Pro Glu His Gly
        610                 615                 620

<210> SEQ ID NO 5
<211> LENGTH: 1959
<212> TYPE: DNA
<213> ORGANISM: Bacillus stearothermophilus TRBE14
<220> FEATURE:
<221> NAME/KEY: CDS
<222> LOCATION: (1)..(1959)

<400> SEQUENCE: 5

| | | |
|---|---|---|
| ttg att gcg gcg aat ccg acg gat ttg gaa gtg tat ttg ttt cat gaa<br>Met Ile Ala Ala Asn Pro Thr Asp Leu Glu Val Tyr Leu Phe His Glu<br>1               5                   10                  15 | | 48 |
| ggc agc ttg tat aaa agt tac gag ctg ttt ggc gcc cat gtg att aat<br>Gly Ser Leu Tyr Lys Ser Tyr Glu Leu Phe Gly Ala His Val Ile Asn<br>            20                  25                  30 | | 96 |
| gag ggc ggg aag gtc ggc acc cgt ttt tgt gtt tgg gcg ccg cac gcg<br>Glu Gly Gly Lys Val Gly Thr Arg Phe Cys Val Trp Ala Pro His Ala<br>        35                  40                  45 | | 144 |
| cgc gag gtg cgt ctt gtc ggc agt ttc aac gat tgg gac ggg acg gat<br>Arg Glu Val Arg Leu Val Gly Ser Phe Asn Asp Trp Asp Gly Thr Asp<br>    50                  55                  60 | | 192 |
| ttt cgc ctt gag aaa gtg aat gat gaa ggg gta tgg acg att gtt gtc<br>Phe Arg Leu Glu Lys Val Asn Asp Glu Gly Val Trp Thr Ile Val Val<br>65                  70                  75                  80 | | 240 |
| ccc gaa aac ttg gaa ggg cat tta tat aag tat gag att gtt acg ccg<br>Pro Glu Asn Leu Glu Gly His Leu Tyr Lys Tyr Glu Ile Val Thr Pro<br>                85                  90                  95 | | 288 |
| gac gga cag gtg ctg ttc aaa gcc gac ccg tac gct ttt tac tcc gaa<br>Asp Gly Gln Val Leu Phe Lys Ala Asp Pro Tyr Ala Phe Tyr Ser Glu<br>            100                 105                 110 | | 336 |
| ttg cgt cct cat acc gcc tcg att gcc tac gat ctg aaa gga tac cag<br>Leu Arg Pro His Thr Ala Ser Ile Ala Tyr Asp Leu Lys Gly Tyr Gln<br>        115                 120                 125 | | 384 |
| tgg aac gat caa tct tgg aag cgg aag aag cga cga aaa cgg att tat<br>Trp Asn Asp Gln Ser Trp Lys Arg Lys Lys Arg Arg Lys Arg Ile Tyr<br>    130                 135                 140 | | 432 |
| gat cag ccc atg gtg att tat gaa ctc cat ttc ggt tcg tgg aag aaa<br>Asp Gln Pro Met Val Ile Tyr Glu Leu His Phe Gly Ser Trp Lys Lys<br>145                 150                 155                 160 | | 480 |
| aaa gat ggg cgt ttt tat acg tac cgt gag atg gcc gat gaa ctg atc<br>Lys Asp Gly Arg Phe Tyr Thr Tyr Arg Glu Met Ala Asp Glu Leu Ile<br>                165                 170                 175 | | 528 |
| tcg tat gtg ctc gat cat ggg ttt acg cac att gag ttg ctt cct ctc<br>Ser Tyr Val Leu Asp His Gly Phe Thr His Ile Glu Leu Leu Pro Leu<br>            180                 185                 190 | | 576 |
| gtc gag cat ccg ctc gac cgc tcg tgg ggc tat caa gga aca ggg tat<br>Val Glu His Pro Leu Asp Arg Ser Trp Gly Tyr Gln Gly Thr Gly Tyr<br>        195                 200                 205 | | 624 |
| tat gcg gta acg agt cgc tat ggt acg cca cac gac ttc atg tac ttc<br>Tyr Ala Val Thr Ser Arg Tyr Gly Thr Pro His Asp Phe Met Tyr Phe<br>    210                 215                 220 | | 672 |
| gtc gac cgt tgc cat cag gcg gga atc ggg gtc att atg gac tgg gtg<br>Val Asp Arg Cys His Gln Ala Gly Ile Gly Val Ile Met Asp Trp Val<br>225                 230                 235                 240 | | 720 |
| ccg ggg cat ttt tgc aag gac gcc cat ggg tta tat atg ttt gat ggc<br>Pro Gly His Phe Cys Lys Asp Ala His Gly Leu Tyr Met Phe Asp Gly | | 768 |

-continued

```
                    245                 250                 255
gcc ccg acg tat gaa tac gcg aat gaa aaa gac cga gaa aat tac gtt    816
Ala Pro Thr Tyr Glu Tyr Ala Asn Glu Lys Asp Arg Glu Asn Tyr Val
            260                 265                 270 tgg ggg acg gcc aat ttt gat tta ggc aag ccg gaa gtg cgc agt ttt    864
Trp Gly Thr Ala Asn Phe Asp Leu Gly Lys Pro Glu Val Arg Ser Phe
        275                 280                 285 ctc atc tcg aac gca ttg ttt tgg ctc gag tat tac cat atc gac ggg    912
Leu Ile Ser Asn Ala Leu Phe Trp Leu Glu Tyr Tyr His Ile Asp Gly
    290                 295                 300 ttc cgg gtc gat gcg gtt gcc aat atg ctt tat tgg ccg aac aat gac    960
Phe Arg Val Asp Ala Val Ala Asn Met Leu Tyr Trp Pro Asn Asn Asp
305                 310                 315                 320 agg ctg tac gag aac ccg tat gcg gtc gag ttt ttg cgc aag tta aac   1008
Arg Leu Tyr Glu Asn Pro Tyr Ala Val Glu Phe Leu Arg Lys Leu Asn
                325                 330                 335 gaa gcg gtg ttt gcc tat gat ccg aat gcg ctg atg att gcg gaa gat   1056
Glu Ala Val Phe Ala Tyr Asp Pro Asn Ala Leu Met Ile Ala Glu Asp
            340                 345                 350 tcg act gac tgg ccg aag gtg acc gcg ccg acg tat gaa ggc gga ctc   1104
Ser Thr Asp Trp Pro Lys Val Thr Ala Pro Thr Tyr Glu Gly Gly Leu
        355                 360                 365 ggc ttt aat tat aaa tgg aac atg ggc tgg atg aac gac atg ctg aag   1152
Gly Phe Asn Tyr Lys Trp Asn Met Gly Trp Met Asn Asp Met Leu Lys
    370                 375                 380 tac atg gaa aca ccg ccg tat gag cgg agg cat gtg cat aac caa gta   1200
Tyr Met Glu Thr Pro Pro Tyr Glu Arg Arg His Val His Asn Gln Val
385                 390                 395                 400 acg ttc tcc ctc ctt tat gcg tat tcg gaa aat ttc att ttg ccg ttt   1248
Thr Phe Ser Leu Leu Tyr Ala Tyr Ser Glu Asn Phe Ile Leu Pro Phe
                405                 410                 415 tcc cac gat gaa gtc gtg cat ggc aaa aaa tcg ctg ctc aat aaa atg   1296
Ser His Asp Glu Val Val His Gly Lys Lys Ser Leu Leu Asn Lys Met
            420                 425                 430 cca ggg tcg tat gaa gag aag ttc gcc cag ctg cgc ctc ttg tac ggc   1344
Pro Gly Ser Tyr Glu Glu Lys Phe Ala Gln Leu Arg Leu Leu Tyr Gly
        435                 440                 445 tac atg atg gct cat ccg ggg aaa aag ctg ttg ttt atg ggc aat gaa   1392
Tyr Met Met Ala His Pro Gly Lys Lys Leu Leu Phe Met Gly Asn Glu
    450                 455                 460 ttt gct cag ttt gat gaa tgg aag ttt gag gat gaa ctc gat tgg gtg   1440
Phe Ala Gln Phe Asp Glu Trp Lys Phe Glu Asp Glu Leu Asp Trp Val
465                 470                 475                 480 ctg ttt gat ttt gag ctg cac cgg aag atg aac gat tac atg aaa gag   1488
Leu Phe Asp Phe Glu Leu His Arg Lys Met Asn Asp Tyr Met Lys Glu
                485                 490                 495 tta atc gcc tgc tat aaa cgg tat aag ccg ttt tac gaa ttg gat cat   1536
Leu Ile Ala Cys Tyr Lys Arg Tyr Lys Pro Phe Tyr Glu Leu Asp His
            500                 505                 510 gac ccg caa gga ttt gaa tgg att gac gtt cac aac gct gaa caa agc   1584
Asp Pro Gln Gly Phe Glu Trp Ile Asp Val His Asn Ala Glu Gln Ser
        515                 520                 525 att ttc tca ttc atc cgc cgc ggg aaa aaa gaa gat gat gtg ctt gtt   1632
Ile Phe Ser Phe Ile Arg Arg Gly Lys Lys Glu Asp Asp Val Leu Val
    530                 535                 540 att gtt tgc aat ttc aca aat cag gcg tat gac gac tac aaa gtt gga   1680
Ile Val Cys Asn Phe Thr Asn Gln Ala Tyr Asp Asp Tyr Lys Val Gly
545                 550                 555                 560 gtg ccg ttg ctc gta ccg tat cgg gaa gtg ctg aat agc gat gcg gtc   1728
```

```
Val Pro Leu Leu Val Pro Tyr Arg Glu Val Leu Asn Ser Asp Ala Val
            565                 570                 575 acg ttt ggt gga tcg ggg cat gtc aat ggg aaa cgg ctt tcc gcc ttc     1776
Thr Phe Gly Gly Ser Gly His Val Asn Gly Lys Arg Leu Ser Ala Phe
            580                 585                 590 aat gag ccg ttt cat ggt aaa cca tac cac gtg cgc atg acg att ccg     1824
Asn Glu Pro Phe His Gly Lys Pro Tyr His Val Arg Met Thr Ile Pro
            595                 600                 605 cca ttt ggc att tcc att tta cgg cca gtg caa aaa cga ggg gag aga     1872
Pro Phe Gly Ile Ser Ile Leu Arg Pro Val Gln Lys Arg Gly Glu Arg
            610                 615                 620 aag cga aat gaa aaa gaa atg cat cgc cat gtt att ggc cgg cgg gca     1920
Lys Arg Asn Glu Lys Glu Met His Arg His Val Ile Gly Arg Arg Ala
625                 630                 635                 640 agg aag tcg gct tcg ctc gct gac gac aaa cat cgc taa                 1959
Arg Lys Ser Ala Ser Leu Ala Asp Asp Lys His Arg
            645                 650

<210> SEQ ID NO 6
<211> LENGTH: 652
<212> TYPE: PRT
<213> ORGANISM: Bacillus stearothermophilus TRBE14

<400> SEQUENCE: 6

Met Ile Ala Ala Asn Pro Thr Asp Leu Glu Val Tyr Leu Phe His Glu
1               5                   10                  15

Gly Ser Leu Tyr Lys Ser Tyr Glu Leu Phe Gly Ala His Val Ile Asn
            20                  25                  30

Glu Gly Gly Lys Val Gly Thr Arg Phe Cys Val Trp Ala Pro His Ala
        35                  40                  45

Arg Glu Val Arg Leu Val Gly Ser Phe Asn Asp Trp Asp Gly Thr Asp
    50                  55                  60

Phe Arg Leu Glu Lys Val Asn Asp Glu Gly Val Trp Thr Ile Val Val
65                  70                  75                  80

Pro Glu Asn Leu Glu Gly His Leu Tyr Lys Tyr Glu Ile Val Thr Pro
                85                  90                  95

Asp Gly Gln Val Leu Phe Lys Ala Asp Pro Tyr Ala Phe Tyr Ser Glu
            100                 105                 110

Leu Arg Pro His Thr Ala Ser Ile Ala Tyr Asp Leu Lys Gly Tyr Gln
        115                 120                 125

Trp Asn Asp Gln Ser Trp Lys Arg Lys Arg Arg Lys Arg Ile Tyr
    130                 135                 140

Asp Gln Pro Met Val Ile Tyr Glu Leu His Phe Gly Ser Trp Lys Lys
145                 150                 155                 160

Lys Asp Gly Arg Phe Tyr Thr Tyr Arg Glu Met Ala Asp Glu Leu Ile
                165                 170                 175

Ser Tyr Val Leu Asp His Gly Phe Thr His Ile Glu Leu Leu Pro Leu
            180                 185                 190

Val Glu His Pro Leu Asp Arg Ser Trp Gly Tyr Gln Gly Thr Gly Tyr
        195                 200                 205

Tyr Ala Val Thr Ser Arg Tyr Gly Thr Pro His Asp Phe Met Tyr Phe
    210                 215                 220

Val Asp Arg Cys His Gln Ala Gly Ile Gly Val Ile Met Asp Trp Val
225                 230                 235                 240

Pro Gly His Phe Cys Lys Asp Ala His Gly Leu Tyr Met Phe Asp Gly
                245                 250                 255
```

```
Ala Pro Thr Tyr Glu Tyr Ala Asn Glu Lys Asp Arg Glu Asn Tyr Val
            260                 265                 270

Trp Gly Thr Ala Asn Phe Asp Leu Gly Lys Pro Glu Val Arg Ser Phe
        275                 280                 285

Leu Ile Ser Asn Ala Leu Phe Trp Leu Glu Tyr Tyr His Ile Asp Gly
        290                 295                 300

Phe Arg Val Asp Ala Val Ala Asn Met Leu Tyr Trp Pro Asn Asn Asp
305                 310                 315                 320

Arg Leu Tyr Glu Asn Pro Tyr Ala Val Glu Phe Leu Arg Lys Leu Asn
                325                 330                 335

Glu Ala Val Phe Ala Tyr Asp Pro Asn Ala Leu Met Ile Ala Glu Asp
                340                 345                 350

Ser Thr Asp Trp Pro Lys Val Thr Ala Pro Thr Tyr Glu Gly Gly Leu
        355                 360                 365

Gly Phe Asn Tyr Lys Trp Asn Met Gly Trp Met Asn Asp Met Leu Lys
        370                 375                 380

Tyr Met Glu Thr Pro Tyr Glu Arg Arg His Val His Asn Gln Val
385                 390                 395                 400

Thr Phe Ser Leu Leu Tyr Ala Tyr Ser Glu Asn Phe Ile Leu Pro Phe
                405                 410                 415

Ser His Asp Glu Val Val His Gly Lys Lys Ser Leu Leu Asn Lys Met
                420                 425                 430

Pro Gly Ser Tyr Glu Glu Lys Phe Ala Gln Leu Arg Leu Leu Tyr Gly
            435                 440                 445

Tyr Met Met Ala His Pro Gly Lys Lys Leu Leu Phe Met Gly Asn Glu
        450                 455                 460

Phe Ala Gln Phe Asp Glu Trp Lys Phe Glu Asp Glu Leu Asp Trp Val
465                 470                 475                 480

Leu Phe Asp Phe Glu Leu His Arg Lys Met Asn Asp Tyr Met Lys Glu
                485                 490                 495

Leu Ile Ala Cys Tyr Lys Arg Tyr Lys Pro Phe Tyr Glu Leu Asp His
            500                 505                 510

Asp Pro Gln Gly Phe Glu Trp Ile Asp Val His Asn Ala Glu Gln Ser
        515                 520                 525

Ile Phe Ser Phe Ile Arg Arg Gly Lys Lys Glu Asp Asp Val Leu Val
        530                 535                 540

Ile Val Cys Asn Phe Thr Asn Gln Ala Tyr Asp Asp Tyr Lys Val Gly
545                 550                 555                 560

Val Pro Leu Leu Val Pro Tyr Arg Glu Val Leu Asn Ser Asp Ala Val
                565                 570                 575

Thr Phe Gly Gly Ser Gly His Val Asn Gly Lys Arg Leu Ser Ala Phe
            580                 585                 590

Asn Glu Pro Phe His Gly Lys Pro Tyr His Val Arg Met Thr Ile Pro
        595                 600                 605

Pro Phe Gly Ile Ser Ile Leu Arg Pro Val Gln Lys Arg Gly Glu Arg
        610                 615                 620

Lys Arg Asn Glu Lys Glu Met His Arg His Val Ile Gly Arg Arg Ala
625                 630                 635                 640

Arg Lys Ser Ala Ser Leu Ala Asp Asp Lys His Arg
                645                 650

<210> SEQ ID NO 7
<211> LENGTH: 1920
<212> TYPE: DNA
```

<213> ORGANISM: Bacillus stearothermophilus 1503 | SR var.4
<220> FEATURE:
<221> NAME/KEY: CDS
<222> LOCATION: (1)..(1920)

<400> SEQUENCE: 7

| | | | | | | | | | | | | | | | | |
|---|---|---|---|---|---|---|---|---|---|---|---|---|---|---|---|---|
| ttg | atc | gcc | gtc | ggt | ccc | act | gat | tta | gaa | atc | tat | tta | ttt | cat | gaa | 48 |
| Met | Ile | Ala | Val | Gly | Pro | Thr | Asp | Leu | Glu | Ile | Tyr | Leu | Phe | His | Glu | |
| 1 | | | | 5 | | | | | 10 | | | | | 15 | | |

| ggc | agc | tta | tat | aaa | agt | tat | gaa | ttg | ttt | ggt | gca | cat | gtg | ata | aag | 96 |
|---|---|---|---|---|---|---|---|---|---|---|---|---|---|---|---|---|
| Gly | Ser | Leu | Tyr | Lys | Ser | Tyr | Glu | Leu | Phe | Gly | Ala | His | Val | Ile | Lys | |
| | | | 20 | | | | | 25 | | | | | 30 | | | |

| aaa | aat | ggc | atg | gtc | gga | acc | cgg | ttt | tgt | gta | tgg | gca | ccc | cat | gcg | 144 |
|---|---|---|---|---|---|---|---|---|---|---|---|---|---|---|---|---|
| Lys | Asn | Gly | Met | Val | Gly | Thr | Arg | Phe | Cys | Val | Trp | Ala | Pro | His | Ala | |
| | | 35 | | | | | 40 | | | | | 45 | | | | |

| cgg | gaa | gtg | cga | tta | gtc | ggc | agt | ttt | aat | gaa | tgg | aac | gga | act | aat | 192 |
|---|---|---|---|---|---|---|---|---|---|---|---|---|---|---|---|---|
| Arg | Glu | Val | Arg | Leu | Val | Gly | Ser | Phe | Asn | Glu | Trp | Asn | Gly | Thr | Asn | |
| 50 | | | | | 55 | | | | | 60 | | | | | | |

| ttt | aac | ctt | atg | aaa | gta | agt | aat | caa | ggc | gta | tgg | atg | att | ttt | att | 240 |
|---|---|---|---|---|---|---|---|---|---|---|---|---|---|---|---|---|
| Phe | Asn | Leu | Met | Lys | Val | Ser | Asn | Gln | Gly | Val | Trp | Met | Ile | Phe | Ile | |
| 65 | | | | 70 | | | | | 75 | | | | | 80 | | |

| cct | gaa | aac | tta | gaa | ggg | cat | tta | tat | aaa | tac | gaa | att | acg | acg | aac | 288 |
|---|---|---|---|---|---|---|---|---|---|---|---|---|---|---|---|---|
| Pro | Glu | Asn | Leu | Glu | Gly | His | Leu | Tyr | Lys | Tyr | Glu | Ile | Thr | Thr | Asn | |
| | | | 85 | | | | | 90 | | | | | 95 | | | |

| gat | ggg | aat | gtt | ctg | tta | aaa | tcg | gat | cca | tac | gcg | ttt | tac | tcc | gag | 336 |
|---|---|---|---|---|---|---|---|---|---|---|---|---|---|---|---|---|
| Asp | Gly | Asn | Val | Leu | Leu | Lys | Ser | Asp | Pro | Tyr | Ala | Phe | Tyr | Ser | Glu | |
| | | 100 | | | | | 105 | | | | | 110 | | | | |

| ttg | cgt | ccc | cat | act | gct | tcc | att | gtc | tac | aac | ata | aaa | gga | tat | caa | 384 |
|---|---|---|---|---|---|---|---|---|---|---|---|---|---|---|---|---|
| Leu | Arg | Pro | His | Thr | Ala | Ser | Ile | Val | Tyr | Asn | Ile | Lys | Gly | Tyr | Gln | |
| | | 115 | | | | | 120 | | | | | 125 | | | | |

| tgg | aat | gac | cag | aca | tgg | cga | cgg | aag | aaa | cag | cga | aag | cga | att | tat | 432 |
|---|---|---|---|---|---|---|---|---|---|---|---|---|---|---|---|---|
| Trp | Asn | Asp | Gln | Thr | Trp | Arg | Arg | Lys | Lys | Gln | Arg | Lys | Arg | Ile | Tyr | |
| | 130 | | | | | 135 | | | | | 140 | | | | | |

| gac | cag | cct | ttg | ttc | att | tat | gaa | ctt | cac | ttt | ggt | tcg | tgg | aaa | aag | 480 |
|---|---|---|---|---|---|---|---|---|---|---|---|---|---|---|---|---|
| Asp | Gln | Pro | Leu | Phe | Ile | Tyr | Glu | Leu | His | Phe | Gly | Ser | Trp | Lys | Lys | |
| 145 | | | | | 150 | | | | | 155 | | | | | 160 | |

| aaa | gag | gac | ggc | agt | ttt | tat | aca | tat | caa | gag | atg | gca | gag | gag | cta | 528 |
|---|---|---|---|---|---|---|---|---|---|---|---|---|---|---|---|---|
| Lys | Glu | Asp | Gly | Ser | Phe | Tyr | Thr | Tyr | Gln | Glu | Met | Ala | Glu | Glu | Leu | |
| | | | | 165 | | | | | 170 | | | | | 175 | | |

| atc | cct | tat | gtt | ctc | gaa | cat | ggg | ttt | act | cat | att | gag | ctg | ctc | cca | 576 |
|---|---|---|---|---|---|---|---|---|---|---|---|---|---|---|---|---|
| Ile | Pro | Tyr | Val | Leu | Glu | His | Gly | Phe | Thr | His | Ile | Glu | Leu | Leu | Pro | |
| | | | 180 | | | | | 185 | | | | | 190 | | | |

| ctc | gtc | gag | cat | ccg | ttc | gat | cgt | tct | tgg | gga | tat | cag | gga | ata | ggt | 624 |
|---|---|---|---|---|---|---|---|---|---|---|---|---|---|---|---|---|
| Leu | Val | Glu | His | Pro | Phe | Asp | Arg | Ser | Trp | Gly | Tyr | Gln | Gly | Ile | Gly | |
| | | 195 | | | | | 200 | | | | | 205 | | | | |

| tat | tat | tca | gca | aca | agc | cgc | tac | gga | aca | ccg | cat | gat | ttg | atg | tat | 672 |
|---|---|---|---|---|---|---|---|---|---|---|---|---|---|---|---|---|
| Tyr | Tyr | Ser | Ala | Thr | Ser | Arg | Tyr | Gly | Thr | Pro | His | Asp | Leu | Met | Tyr | |
| | 210 | | | | | 215 | | | | | 220 | | | | | |

| ttt | att | gac | cgc | tgt | cac | caa | gct | gga | ata | ggc | gtc | att | ctc | gat | tgg | 720 |
|---|---|---|---|---|---|---|---|---|---|---|---|---|---|---|---|---|
| Phe | Ile | Asp | Arg | Cys | His | Gln | Ala | Gly | Ile | Gly | Val | Ile | Leu | Asp | Trp | |
| 225 | | | | | 230 | | | | | 235 | | | | | 240 | |

| gtt | cct | ggc | cac | ttt | tgt | aaa | gat | tcc | cat | ggg | tta | tat | atg | ttt | gat | 768 |
|---|---|---|---|---|---|---|---|---|---|---|---|---|---|---|---|---|
| Val | Pro | Gly | His | Phe | Cys | Lys | Asp | Ser | His | Gly | Leu | Tyr | Met | Phe | Asp | |
| | | | | 245 | | | | | 250 | | | | | 255 | | |

| ggc | gca | ccg | gca | tat | gaa | tat | gcc | aac | atg | caa | gac | cgg | gaa | aat | tac | 816 |
|---|---|---|---|---|---|---|---|---|---|---|---|---|---|---|---|---|
| Gly | Ala | Pro | Ala | Tyr | Glu | Tyr | Ala | Asn | Met | Gln | Asp | Arg | Glu | Asn | Tyr | |
| | | | 260 | | | | | 265 | | | | | 270 | | | |

| gta | tgg | gga | acg | gca | aac | ttt | gac | ctt | ggc | aag | ccg | gaa | gtc | cgc | agc | 864 |
|---|---|---|---|---|---|---|---|---|---|---|---|---|---|---|---|---|
| Val | Trp | Gly | Thr | Ala | Asn | Phe | Asp | Leu | Gly | Lys | Pro | Glu | Val | Arg | Ser | |
| | | 275 | | | | | 280 | | | | | 285 | | | | |

-continued

| | | |
|---|---|---|
| ttt ttg att tcc aat gcg tta ttt tgg atg gaa tat ttc cat gtg gac<br>Phe Leu Ile Ser Asn Ala Leu Phe Trp Met Glu Tyr Phe His Val Asp<br>290                   295                     300 | 912 |
| ggg ttt cgt gta gat gct gtt gcc aat atg tta tat tgg cca aac agc<br>Gly Phe Arg Val Asp Ala Val Ala Asn Met Leu Tyr Trp Pro Asn Ser<br>305                  310                   315                  320 | 960 |
| gac gta cta tac aaa aat acg tat gcc gtg gag ttc ttg caa aaa tta<br>Asp Val Leu Tyr Lys Asn Thr Tyr Ala Val Glu Phe Leu Gln Lys Leu<br>                       325                     330                  335 | 1008 |
| aat gaa acg gta ttc gcc tat gat ccg aac ata tta atg att gcc gaa<br>Asn Glu Thr Val Phe Ala Tyr Asp Pro Asn Ile Leu Met Ile Ala Glu<br>                  340                   345                  350 | 1056 |
| gat tcg aca gac tgg ccg cgc gtc act gct cca aca tac gac gga gga<br>Asp Ser Thr Asp Trp Pro Arg Val Thr Ala Pro Thr Tyr Asp Gly Gly<br>355                   360                     365 | 1104 |
| tta gga ttt aac tat aaa tgg aac atg gga tgg atg aac gat att tta<br>Leu Gly Phe Asn Tyr Lys Trp Asn Met Gly Trp Met Asn Asp Ile Leu<br>370                   375                   380 | 1152 |
| act tat atg gaa acg ccg cct gaa cat cga aaa tac gtg cac aat aaa<br>Thr Tyr Met Glu Thr Pro Pro Glu His Arg Lys Tyr Val His Asn Lys<br>385                     390                   395                  400 | 1200 |
| gta aca ttt tcc ctc ttg tat gcg tat tcg gaa aat ttc att tta cct<br>Val Thr Phe Ser Leu Leu Tyr Ala Tyr Ser Glu Asn Phe Ile Leu Pro<br>                       405                     410                  415 | 1248 |
| ttt tcc cat gac gag gtc gta cat gga aaa aaa tcg ctg tta agt aaa<br>Phe Ser His Asp Glu Val Val His Gly Lys Lys Ser Leu Leu Ser Lys<br>                  420                   425                  430 | 1296 |
| atg ccg ggg aca tat gag gaa aag ttt gcg caa tta agg ttg ctg tat<br>Met Pro Gly Thr Tyr Glu Glu Lys Phe Ala Gln Leu Arg Leu Leu Tyr<br>435                   440                   445 | 1344 |
| gga tat ttg ttg acg cat cct ggt aag aaa tta ttg ttt atg ggc ggc<br>Gly Tyr Leu Leu Thr His Pro Gly Lys Lys Leu Leu Phe Met Gly Gly<br>450                   455                   460 | 1392 |
| gaa ttt ggc cag ttt gat gaa tgg aaa gat tta gag cag ctg gat tgg<br>Glu Phe Gly Gln Phe Asp Glu Trp Lys Asp Leu Glu Gln Leu Asp Trp<br>465                   470                   475                  480 | 1440 |
| atg ctt ttt gat ttt gat atg cat cgg aat atg aat atg tat gtg aaa<br>Met Leu Phe Asp Phe Asp Met His Arg Asn Met Asn Met Tyr Val Lys<br>                  485                   490                  495 | 1488 |
| gaa ttg ttg aaa tgt tat aag cgc tat aaa ccg ctt tat gag tta gac<br>Glu Leu Leu Lys Cys Tyr Lys Arg Tyr Lys Pro Leu Tyr Glu Leu Asp<br>                     500                   505                  510 | 1536 |
| cac tct cca gat gga ttc gag tgg att gat gtt cat aac gcc gaa caa<br>His Ser Pro Asp Gly Phe Glu Trp Ile Asp Val His Asn Ala Glu Gln<br>                  515                   520                  525 | 1584 |
| agt att ttc tca ttc att cgc aga gga aaa aaa gag gat gat ttg ctt<br>Ser Ile Phe Ser Phe Ile Arg Arg Gly Lys Lys Glu Asp Asp Leu Leu<br>530                   535                   540 | 1632 |
| att gtt gtg tgt aat ttc aca aat aaa gta tac cac ggt tat aaa gtt<br>Ile Val Val Cys Asn Phe Thr Asn Lys Val Tyr His Gly Tyr Lys Val<br>545                   550                   555                  560 | 1680 |
| ggt gtt ccg tta ttt aca aga tat cgg gaa gta atc aat agc gat gca<br>Gly Val Pro Leu Phe Thr Arg Tyr Arg Glu Val Ile Asn Ser Asp Ala<br>                  565                   570                  575 | 1728 |
| atc caa ttc ggc ggc ttt ggg aat atc aat cca aaa ccg att gcg gcg<br>Ile Gln Phe Gly Gly Phe Gly Asn Ile Asn Pro Lys Pro Ile Ala Ala<br>                     580                   585                  590 | 1776 |
| atg gaa ggg ccg ttt cac gga aag cca tat cat att cag atg acg atc<br>Met Glu Gly Pro Phe His Gly Lys Pro Tyr His Ile Gln Met Thr Ile<br>                  595                   600                  605 | 1824 |

```
ccg ccg ttt ggc att tct att tta aga cca gta aaa aaa ggt agc gtc    1872
Pro Pro Phe Gly Ile Ser Ile Leu Arg Pro Val Lys Lys Gly Ser Val
    610             615             620 aaa agt ttt atg aaa act cca cat ccg cca tcc cat gga gca tcg taa    1920
Lys Ser Phe Met Lys Thr Pro His Pro Pro Ser His Gly Ala Ser
625             630             635
```

<210> SEQ ID NO 8
<211> LENGTH: 639
<212> TYPE: PRT
<213> ORGANISM: Bacillus stearothermophilus 1503 | SR var.4

<400> SEQUENCE: 8

```
Met Ile Ala Val Gly Pro Thr Asp Leu Glu Ile Tyr Leu Phe His Glu
1               5                   10                  15

Gly Ser Leu Tyr Lys Ser Tyr Glu Leu Phe Gly Ala His Val Ile Lys
            20                  25                  30

Lys Asn Gly Met Val Gly Thr Arg Phe Cys Val Trp Ala Pro His Ala
        35                  40                  45

Arg Glu Val Arg Leu Val Gly Ser Phe Asn Glu Trp Asn Gly Thr Asn
    50                  55                  60

Phe Asn Leu Met Lys Val Ser Asn Gln Gly Val Trp Met Ile Phe Ile
65                  70                  75                  80

Pro Glu Asn Leu Glu Gly His Leu Tyr Lys Tyr Glu Ile Thr Thr Asn
                85                  90                  95

Asp Gly Asn Val Leu Leu Lys Ser Asp Pro Tyr Ala Phe Tyr Ser Glu
            100                 105                 110

Leu Arg Pro His Thr Ala Ser Ile Val Tyr Asn Ile Lys Gly Tyr Gln
        115                 120                 125

Trp Asn Asp Gln Thr Trp Arg Arg Lys Lys Gln Arg Lys Arg Ile Tyr
    130                 135                 140

Asp Gln Pro Leu Phe Ile Tyr Glu Leu His Phe Gly Ser Trp Lys Lys
145                 150                 155                 160

Lys Glu Asp Gly Ser Phe Tyr Thr Tyr Gln Glu Met Ala Glu Glu Leu
                165                 170                 175

Ile Pro Tyr Val Leu Glu His Gly Phe Thr His Ile Glu Leu Leu Pro
            180                 185                 190

Leu Val Glu His Pro Phe Asp Arg Ser Trp Gly Tyr Gln Gly Ile Gly
        195                 200                 205

Tyr Tyr Ser Ala Thr Ser Arg Tyr Gly Thr Pro His Asp Leu Met Tyr
    210                 215                 220

Phe Ile Asp Arg Cys His Gln Ala Gly Ile Gly Val Ile Leu Asp Trp
225                 230                 235                 240

Val Pro Gly His Phe Cys Lys Asp Ser His Gly Leu Tyr Met Phe Asp
                245                 250                 255

Gly Ala Pro Ala Tyr Glu Tyr Ala Asn Met Gln Asp Arg Glu Asn Tyr
            260                 265                 270

Val Trp Gly Thr Ala Asn Phe Asp Leu Gly Lys Pro Glu Val Arg Ser
        275                 280                 285

Phe Leu Ile Ser Asn Ala Leu Phe Trp Met Glu Tyr Phe His Val Asp
    290                 295                 300

Gly Phe Arg Val Asp Ala Val Ala Asn Met Leu Tyr Trp Pro Asn Ser
305                 310                 315                 320

Asp Val Leu Tyr Lys Asn Thr Tyr Ala Val Glu Phe Leu Gln Lys Leu
                325                 330                 335
```

-continued

```
Asn Glu Thr Val Phe Ala Tyr Asp Pro Asn Ile Leu Met Ile Ala Glu
            340                 345                 350

Asp Ser Thr Asp Trp Pro Arg Val Thr Ala Pro Thr Tyr Asp Gly Gly
        355                 360                 365

Leu Gly Phe Asn Tyr Lys Trp Asn Met Gly Trp Met Asn Asp Ile Leu
    370                 375                 380

Thr Tyr Met Glu Thr Pro Pro Glu His Arg Lys Tyr Val His Asn Lys
385                 390                 395                 400

Val Thr Phe Ser Leu Leu Tyr Ala Tyr Ser Glu Asn Phe Ile Leu Pro
                405                 410                 415

Phe Ser His Asp Glu Val Val His Gly Lys Lys Ser Leu Leu Ser Lys
            420                 425                 430

Met Pro Gly Thr Tyr Glu Glu Lys Phe Ala Gln Leu Arg Leu Leu Tyr
        435                 440                 445

Gly Tyr Leu Leu Thr His Pro Gly Lys Lys Leu Leu Phe Met Gly Gly
    450                 455                 460

Glu Phe Gly Gln Phe Asp Glu Trp Lys Asp Leu Glu Gln Leu Asp Trp
465                 470                 475                 480

Met Leu Phe Asp Phe Asp Met His Arg Asn Met Asn Met Tyr Val Lys
                485                 490                 495

Glu Leu Leu Lys Cys Tyr Lys Arg Tyr Lys Pro Leu Tyr Glu Leu Asp
            500                 505                 510

His Ser Pro Asp Gly Phe Glu Trp Ile Asp Val His Asn Ala Glu Gln
        515                 520                 525

Ser Ile Phe Ser Phe Ile Arg Arg Gly Lys Lys Glu Asp Asp Leu Leu
    530                 535                 540

Ile Val Val Cys Asn Phe Thr Asn Lys Val Tyr His Gly Tyr Lys Val
545                 550                 555                 560

Gly Val Pro Leu Phe Thr Arg Tyr Arg Glu Val Ile Asn Ser Asp Ala
                565                 570                 575

Ile Gln Phe Gly Gly Phe Gly Asn Ile Asn Pro Lys Pro Ile Ala Ala
            580                 585                 590

Met Glu Gly Pro Phe His Gly Lys Pro Tyr His Ile Gln Met Thr Ile
        595                 600                 605

Pro Pro Phe Gly Ile Ser Ile Leu Arg Pro Val Lys Lys Gly Ser Val
    610                 615                 620

Lys Ser Phe Met Lys Thr Pro His Pro Ser His Gly Ala Ser
625                 630                 635
```

<210> SEQ ID NO 9
<211> LENGTH: 2001
<212> TYPE: DNA
<213> ORGANISM: Bacillus caldovelox IFO15315
<220> FEATURE:
<221> NAME/KEY: CDS
<222> LOCATION: (1)..(2001)

<400> SEQUENCE: 9

```
ttg att gcg gcg aat ccg aca gat tta gaa gtg tat ttg ttt cat gaa    48
Met Ile Ala Ala Asn Pro Thr Asp Leu Glu Val Tyr Leu Phe His Glu
1               5                  10                  15 ggc cgt ttg tat caa agt tat gag ttg ttc ggc gct cat gtc atc cgc    96
Gly Arg Leu Tyr Gln Ser Tyr Glu Leu Phe Gly Ala His Val Ile Arg
                20                  25                  30 gac ggc gga gcg gtc ggc act cgc ttt tgc gtg tgg gcg ccc cat gcg   144
Asp Gly Gly Ala Val Gly Thr Arg Phe Cys Val Trp Ala Pro His Ala
```

|  |  |  |  |  |  |  |  |  |  |  |  |  |  |  |  |
|---|---|---|---|---|---|---|---|---|---|---|---|---|---|---|---|
|  |  | 35 |  |  |  | 40 |  |  |  | 45 |  |  |  |  |  |

```
cgg gaa gtc cgt ctt gtc ggc agt ttc aac gat tgg aat ggg gcg aat       192
Arg Glu Val Arg Leu Val Gly Ser Phe Asn Asp Trp Asn Gly Ala Asn
     50                  55                  60 tcc ccc ctg acg aag gtg aac gac gaa ggg gta tgg acg atc gtt gtt       240
Ser Pro Leu Thr Lys Val Asn Asp Glu Gly Val Trp Thr Ile Val Val
 65                  70                  75                  80 cca gaa aac ttg gaa ggg cat ctc tat aaa tat gag atc atc aca ccg       288
Pro Glu Asn Leu Glu Gly His Leu Tyr Lys Tyr Glu Ile Ile Thr Pro
                 85                  90                  95 gat ggc cgt gtt ctg ttg aaa gcc gac ccg tac gcc ttt tac tcc gaa       336
Asp Gly Arg Val Leu Leu Lys Ala Asp Pro Tyr Ala Phe Tyr Ser Glu
            100                 105                 110 ttg cgc cct cat acc gcc tcg att gtc tac gat ttg aaa gga tac gag       384
Leu Arg Pro His Thr Ala Ser Ile Val Tyr Asp Leu Lys Gly Tyr Glu
        115                 120                 125 tgg aat gat tca tct tgg cag cgg aag aaa cgg cga aag cgg att tat       432
Trp Asn Asp Ser Ser Trp Gln Arg Lys Lys Arg Arg Lys Arg Ile Tyr
    130                 135                 140 gac caa ccg atg gtc att tat gaa ctt cat ttc ggt tcg tgg aaa aag       480
Asp Gln Pro Met Val Ile Tyr Glu Leu His Phe Gly Ser Trp Lys Lys
145                 150                 155                 160 aaa ccg gac ggc cgc ttt tat acg tac cgt gag atg gcc gac gaa ctt       528
Lys Pro Asp Gly Arg Phe Tyr Thr Tyr Arg Glu Met Ala Asp Glu Leu
                165                 170                 175 atc ccg tac gtg cta gag cgt gga ttt acg cac att gag ctg ctt ccg       576
Ile Pro Tyr Val Leu Glu Arg Gly Phe Thr His Ile Glu Leu Leu Pro
            180                 185                 190 ctt gtc gag cat ccg ctc gac cgt tcg tgg ggg tat caa ggg acc ggc       624
Leu Val Glu His Pro Leu Asp Arg Ser Trp Gly Tyr Gln Gly Thr Gly
        195                 200                 205 tat tat gcg gtg aca agc cgc tac ggt gcg ccg cat gat ttc atg tat       672
Tyr Tyr Ala Val Thr Ser Arg Tyr Gly Ala Pro His Asp Phe Met Tyr
    210                 215                 220 ttc gtc gac cgc tgc cat cag gca gga atc ggg gtc att ctc gat tgg       720
Phe Val Asp Arg Cys His Gln Ala Gly Ile Gly Val Ile Leu Asp Trp
225                 230                 235                 240 gtg ccg ggg cat ttt tgc aag gac gcc cac ggg tta tat atg ttt gac       768
Val Pro Gly His Phe Cys Lys Asp Ala His Gly Leu Tyr Met Phe Asp
                245                 250                 255 ggc gcc ccg acg tac gaa tat gcg aac gaa aaa gac cgg gaa aat tac       816
Gly Ala Pro Thr Tyr Glu Tyr Ala Asn Glu Lys Asp Arg Glu Asn Tyr
            260                 265                 270 gtc tgg ggg acg gcg aat ttt gac ttg ggc aaa ccg gaa gtg cgc agt       864
Val Trp Gly Thr Ala Asn Phe Asp Leu Gly Lys Pro Glu Val Arg Ser
        275                 280                 285 ttt ctc atc tcc aac gcc ttg ttt tgg ctc gag tat tac cac gtc gac       912
Phe Leu Ile Ser Asn Ala Leu Phe Trp Leu Glu Tyr Tyr His Val Asp
    290                 295                 300 gga ttc cgc gtc gat gcg gtc gcg aac atg ctg tat tgg ccg aac aac       960
Gly Phe Arg Val Asp Ala Val Ala Asn Met Leu Tyr Trp Pro Asn Asn
305                 310                 315                 320 gac cag ctc tat gaa aac ccg tat gcg gtc gag ttt ttg cgc aag tta      1008
Asp Gln Leu Tyr Glu Asn Pro Tyr Ala Val Glu Phe Leu Arg Lys Leu
                325                 330                 335 aac gaa gcg gtg ttt gcc tat gac ccc aac gtc ttg atg atc gcc gaa      1056
Asn Glu Ala Val Phe Ala Tyr Asp Pro Asn Val Leu Met Ile Ala Glu
            340                 345                 350 gat tcg acc gat tgg ccg cgg gtg acg gcg ccg acg tat gac ggc ggg      1104
Asp Ser Thr Asp Trp Pro Arg Val Thr Ala Pro Thr Tyr Asp Gly Gly
```

```
Asp Ser Thr Asp Trp Pro Arg Val Thr Ala Pro Thr Tyr Asp Gly Gly
        355                 360                 365 ctt ggc ttt aac tac aag tgg aac atg ggc tgg atg aac gac atg ctg    1152
Leu Gly Phe Asn Tyr Lys Trp Asn Met Gly Trp Met Asn Asp Met Leu
370                 375                 380 aag tat atg gaa acg ccg ccg cat gag cgg aaa tac gcc cat aac caa    1200
Lys Tyr Met Glu Thr Pro Pro His Glu Arg Lys Tyr Ala His Asn Gln
385                 390                 395                 400 gtc agt ttt tcc ctc ctt tat gcg tat tca gaa aat ttc att ttg ccg    1248
Val Ser Phe Ser Leu Leu Tyr Ala Tyr Ser Glu Asn Phe Ile Leu Pro
                405                 410                 415 ttt tct cat gat gaa gtt gtg cat ggc aaa aag tcg ctg ctc aac aaa    1296
Phe Ser His Asp Glu Val Val His Gly Lys Lys Ser Leu Leu Asn Lys
            420                 425                 430 atg ccg ggg tcg tac gag gag aag ttc gcc cag ctg agg ctg ttg tac    1344
Met Pro Gly Ser Tyr Glu Glu Lys Phe Ala Gln Leu Arg Leu Leu Tyr
        435                 440                 445 ggc tac atg atg gcc cac ccc ggg aaa aag ttg ttg ttt atg ggc aac    1392
Gly Tyr Met Met Ala His Pro Gly Lys Lys Leu Leu Phe Met Gly Asn
    450                 455                 460 gaa ttc gcc cag ttt gac gaa tgg aag ttt gag gga gag ctc gac tgg    1440
Glu Phe Ala Gln Phe Asp Glu Trp Lys Phe Glu Gly Glu Leu Asp Trp
465                 470                 475                 480 gtg ctg ttt gat ttt gac ttg cac cgg aag atg gat gag tat gtc aag    1488
Val Leu Phe Asp Phe Asp Leu His Arg Lys Met Asp Glu Tyr Val Lys
                485                 490                 495 caa ttg atc gcc tgc tac aag cgg tat aag ccg ttt tac gag ctt gat    1536
Gln Leu Ile Ala Cys Tyr Lys Arg Tyr Lys Pro Phe Tyr Glu Leu Asp
            500                 505                 510 cat gat ccg agg ggg ttt gaa tgg att gac gtt cat aat gcc gag caa    1584
His Asp Pro Arg Gly Phe Glu Trp Ile Asp Val His Asn Ala Glu Gln
        515                 520                 525 agt att ttc tca ttc atc cgc cgc ggg aaa aaa gac ggc gat cta ttg    1632
Ser Ile Phe Ser Phe Ile Arg Arg Gly Lys Lys Asp Gly Asp Leu Leu
    530                 535                 540 gta att gtt tgc aat ttc aca aat cag gcg tat gac gat tac aaa gtc    1680
Val Ile Val Cys Asn Phe Thr Asn Gln Ala Tyr Asp Asp Tyr Lys Val
545                 550                 555                 560 ggc gtg ccg ctt ttg gcg ccg tac cgc gaa gtg ctg agc agc gat gca    1728
Gly Val Pro Leu Leu Ala Pro Tyr Arg Glu Val Leu Ser Ser Asp Ala
                565                 570                 575 gcg gag ttt ggc gga tca ggg cat gtc aat tcg aag cgg ctt tcc gct    1776
Ala Glu Phe Gly Gly Ser Gly His Val Asn Ser Lys Arg Leu Ser Ala
            580                 585                 590 ttc cat gag ccg ttt cat gga aaa ccg tac cat gtg cgc atg acg att    1824
Phe His Glu Pro Phe His Gly Lys Pro Tyr His Val Arg Met Thr Ile
        595                 600                 605 ccg ccg ttt ggc att tcc att ttg cgg cca gtg caa aaa cga ggg gag    1872
Pro Pro Phe Gly Ile Ser Ile Leu Arg Pro Val Gln Lys Arg Gly Glu
    610                 615                 620 aga aag cag aat gaa gaa gaa gtg cat cgc cat gtt att ggc cgg cgg    1920
Arg Lys Gln Asn Glu Glu Glu Val His Arg His Val Ile Gly Arg Arg
625                 630                 635                 640 gca agg aag ccg gct tcg ctc gct gac gaa aaa cat cgc gaa acc agc    1968
Ala Arg Lys Pro Ala Ser Leu Ala Asp Glu Lys His Arg Glu Thr Ser
                645                 650                 655 cgt gcc gtt tgg ggg gaa gta ccg gat cat tga                        2001
Arg Ala Val Trp Gly Glu Val Pro Asp His
            660                 665
```

<210> SEQ ID NO 10
<211> LENGTH: 666
<212> TYPE: PRT
<213> ORGANISM: Bacillus caldovelox IFO15315

<400> SEQUENCE: 10

Met Ile Ala Ala Asn Pro Thr Asp Leu Glu Val Tyr Leu Phe His Glu
1               5                   10                  15

Gly Arg Leu Tyr Gln Ser Tyr Glu Leu Phe Gly Ala His Val Ile Arg
            20                  25                  30

Asp Gly Gly Ala Val Gly Thr Arg Phe Cys Val Trp Ala Pro His Ala
        35                  40                  45

Arg Glu Val Arg Leu Val Gly Ser Phe Asn Asp Trp Asn Gly Ala Asn
    50                  55                  60

Ser Pro Leu Thr Lys Val Asn Asp Glu Gly Val Trp Thr Ile Val Val
65                  70                  75                  80

Pro Glu Asn Leu Glu Gly His Leu Tyr Lys Tyr Glu Ile Ile Thr Pro
                85                  90                  95

Asp Gly Arg Val Leu Leu Lys Ala Asp Pro Tyr Ala Phe Tyr Ser Glu
            100                 105                 110

Leu Arg Pro His Thr Ala Ser Ile Val Tyr Asp Leu Lys Gly Tyr Glu
        115                 120                 125

Trp Asn Asp Ser Ser Trp Gln Arg Lys Lys Arg Lys Arg Ile Tyr
    130                 135                 140

Asp Gln Pro Met Val Ile Tyr Glu Leu His Phe Gly Ser Trp Lys Lys
145                 150                 155                 160

Lys Pro Asp Gly Arg Phe Tyr Thr Tyr Arg Glu Met Ala Asp Glu Leu
                165                 170                 175

Ile Pro Tyr Val Leu Glu Arg Gly Phe Thr His Ile Glu Leu Leu Pro
            180                 185                 190

Leu Val Glu His Pro Leu Asp Arg Ser Trp Gly Tyr Gln Gly Thr Gly
        195                 200                 205

Tyr Tyr Ala Val Thr Ser Arg Tyr Gly Ala Pro His Asp Phe Met Tyr
    210                 215                 220

Phe Val Asp Arg Cys His Gln Ala Gly Ile Gly Val Ile Leu Asp Trp
225                 230                 235                 240

Val Pro Gly His Phe Cys Lys Asp Ala His Gly Leu Tyr Met Phe Asp
                245                 250                 255

Gly Ala Pro Thr Tyr Glu Tyr Ala Asn Glu Lys Asp Arg Glu Asn Tyr
            260                 265                 270

Val Trp Gly Thr Ala Asn Phe Asp Leu Gly Lys Pro Glu Val Arg Ser
        275                 280                 285

Phe Leu Ile Ser Asn Ala Leu Phe Trp Leu Glu Tyr Tyr His Val Asp
    290                 295                 300

Gly Phe Arg Val Asp Ala Val Ala Asn Met Leu Tyr Trp Pro Asn Asn
305                 310                 315                 320

Asp Gln Leu Tyr Glu Asn Pro Tyr Ala Val Glu Phe Leu Arg Lys Leu
                325                 330                 335

Asn Glu Ala Val Phe Ala Tyr Asp Pro Asn Val Leu Met Ile Ala Glu
            340                 345                 350

Asp Ser Thr Asp Trp Pro Arg Val Thr Ala Pro Thr Tyr Asp Gly Gly
        355                 360                 365

Leu Gly Phe Asn Tyr Lys Trp Asn Met Gly Trp Met Asn Asp Met Leu
    370                 375                 380

```
Lys Tyr Met Glu Thr Pro Pro His Glu Arg Lys Tyr Ala His Asn Gln
385                 390                 395                 400

Val Ser Phe Ser Leu Leu Tyr Ala Tyr Ser Glu Asn Phe Ile Leu Pro
            405                 410                 415

Phe Ser His Asp Glu Val Val His Gly Lys Lys Ser Leu Leu Asn Lys
        420                 425                 430

Met Pro Gly Ser Tyr Glu Glu Lys Phe Ala Gln Leu Arg Leu Leu Tyr
    435                 440                 445

Gly Tyr Met Met Ala His Pro Gly Lys Lys Leu Leu Phe Met Gly Asn
450                 455                 460

Glu Phe Ala Gln Phe Asp Glu Trp Lys Phe Glu Gly Glu Leu Asp Trp
465                 470                 475                 480

Val Leu Phe Asp Phe Asp Leu His Arg Lys Met Asp Glu Tyr Val Lys
            485                 490                 495

Gln Leu Ile Ala Cys Tyr Lys Arg Tyr Lys Pro Phe Tyr Glu Leu Asp
        500                 505                 510

His Asp Pro Arg Gly Phe Glu Trp Ile Asp Val His Asn Ala Glu Gln
    515                 520                 525

Ser Ile Phe Ser Phe Ile Arg Arg Gly Lys Lys Asp Gly Asp Leu Leu
530                 535                 540

Val Ile Val Cys Asn Phe Thr Asn Gln Ala Tyr Asp Asp Tyr Lys Val
545                 550                 555                 560

Gly Val Pro Leu Leu Ala Pro Tyr Arg Glu Val Leu Ser Ser Asp Ala
            565                 570                 575

Ala Glu Phe Gly Gly Ser Gly His Val Asn Ser Lys Arg Leu Ser Ala
        580                 585                 590

Phe His Glu Pro Phe His Gly Lys Pro Tyr His Val Arg Met Thr Ile
    595                 600                 605

Pro Pro Phe Gly Ile Ser Ile Leu Arg Pro Val Gln Lys Arg Gly Glu
610                 615                 620

Arg Lys Gln Asn Glu Glu Val His Arg His Val Ile Gly Arg Arg
625                 630                 635                 640

Ala Arg Lys Pro Ala Ser Leu Ala Asp Glu Lys His Arg Glu Thr Ser
            645                 650                 655

Arg Ala Val Trp Gly Glu Val Pro Asp His
        660                 665

<210> SEQ ID NO 11
<211> LENGTH: 2001
<212> TYPE: DNA
<213> ORGANISM: Bacillus thermocatenulatus IFO15316
<220> FEATURE:
<221> NAME/KEY: CDS
<222> LOCATION: (1)..(2001)

<400> SEQUENCE: 11 ttg att gcg gcg aat ccg aca gat tta gaa gtg tat ttg ttt cat gaa      48
Met Ile Ala Ala Asn Pro Thr Asp Leu Glu Val Tyr Leu Phe His Glu
1               5                   10                  15 ggc cgt ttg tat caa agt tat gag ctg ttc ggc gct cat gtc atc cgc      96
Gly Arg Leu Tyr Gln Ser Tyr Glu Leu Phe Gly Ala His Val Ile Arg
            20                  25                  30 gac ggc gga gcg atc ggt act cgc ttt tgc gtg tgg gcg ccc cat gcg     144
Asp Gly Gly Ala Ile Gly Thr Arg Phe Cys Val Trp Ala Pro His Ala
        35                  40                  45 cgg gaa gtc cgt ctt gtc ggt agt ttc aac gat tgg aat ggg gcg aat     192
```

```
                Arg Glu Val Arg Leu Val Gly Ser Phe Asn Asp Trp Asn Gly Ala Asn
                 50                  55                  60 tcc ccc ctg acg aag gtg aac gac gaa ggg gta tgg acg atc gtt gtt       240
Ser Pro Leu Thr Lys Val Asn Asp Glu Gly Val Trp Thr Ile Val Val
 65                  70                  75                  80 cca gaa aac ttg gaa ggg cat ctc tat aaa tat gag atc atc aca ccg       288
Pro Glu Asn Leu Glu Gly His Leu Tyr Lys Tyr Glu Ile Ile Thr Pro
                 85                  90                  95 gat ggc cgt gtt ctg ttg aaa gcg gac ccg tac gcc ttt tgc tcc gaa       336
Asp Gly Arg Val Leu Leu Lys Ala Asp Pro Tyr Ala Phe Cys Ser Glu
            100                 105                 110 ttg cgc cct cat acc gcc tcg att gtc tac gat ttg aaa gga tac gag       384
Leu Arg Pro His Thr Ala Ser Ile Val Tyr Asp Leu Lys Gly Tyr Glu
            115                 120                 125 tgg aat gat tca tct tgg cag cgg aag aaa cgg cga aag cgg att tat       432
Trp Asn Asp Ser Ser Trp Gln Arg Lys Lys Arg Arg Lys Arg Ile Tyr
        130                 135                 140 gac caa ccg atg gtc att tat gaa ctt cat ttc ggt tcg tgg aaa aag       480
Asp Gln Pro Met Val Ile Tyr Glu Leu His Phe Gly Ser Trp Lys Lys
145                 150                 155                 160 aaa ccg gac ggc cgc ttt tat aca tac cgt gag atg gcg gac gaa ctc       528
Lys Pro Asp Gly Arg Phe Tyr Thr Tyr Arg Glu Met Ala Asp Glu Leu
                165                 170                 175 att ccg tac gtg ctg gag cgc gga ttt acg cac att gag ctg ctt ccg       576
Ile Pro Tyr Val Leu Glu Arg Gly Phe Thr His Ile Glu Leu Leu Pro
            180                 185                 190 ctt gtc gag cat ccg ctc gat cgt tcg tgg gga tat caa ggg act ggc       624
Leu Val Glu His Pro Leu Asp Arg Ser Trp Gly Tyr Gln Gly Thr Gly
            195                 200                 205 tat tat tcg gtg aca agc cgc tat ggc aca ccg cac gat ttc atg tat       672
Tyr Tyr Ser Val Thr Ser Arg Tyr Gly Thr Pro His Asp Phe Met Tyr
        210                 215                 220 ttc gtc gac cgc tgc cat caa gcg agg ctt ggc gtc atc atc gac tgg       720
Phe Val Asp Arg Cys His Gln Ala Arg Leu Gly Val Ile Ile Asp Trp
225                 230                 235                 240 gtg ccg ggg cat ttt tgc aag gac gcc cac ggg ctg tac atg ttt gac       768
Val Pro Gly His Phe Cys Lys Asp Ala His Gly Leu Tyr Met Phe Asp
                245                 250                 255 ggc gcg ccg acg tat gaa tac gcg aat gaa aaa gac cga gaa aat tac       816
Gly Ala Pro Thr Tyr Glu Tyr Ala Asn Glu Lys Asp Arg Glu Asn Tyr
            260                 265                 270 gtc tgg ggg acg gcg aat ttt gac ttg ggc aag ccg gaa gtg cgc agt       864
Val Trp Gly Thr Ala Asn Phe Asp Leu Gly Lys Pro Glu Val Arg Ser
        275                 280                 285 ttt ctg atc tcc aat gcg ttg ttt tgg ctg gag tat tac cat gtg gac       912
Phe Leu Ile Ser Asn Ala Leu Phe Trp Leu Glu Tyr Tyr His Val Asp
        290                 295                 300 ggg ttt cgc gtc gat gcg gtc gcc aat atg ctt tat tgg ccg aac aat       960
Gly Phe Arg Val Asp Ala Val Ala Asn Met Leu Tyr Trp Pro Asn Asn
305                 310                 315                 320 gat agg ctg tac gaa aat ccg tat gcg gtc gag ttt ttg cgc cag ttg      1008
Asp Arg Leu Tyr Glu Asn Pro Tyr Ala Val Glu Phe Leu Arg Gln Leu
                325                 330                 335 aat gag gcg gtg ttt gcc tat gac ccg aat gtc ttg atg att gcg gaa      1056
Asn Glu Ala Val Phe Ala Tyr Asp Pro Asn Val Leu Met Ile Ala Glu
            340                 345                 350 gat tcg acc gac tgg cct cgg gtg acc gcg ccg acg tac gat ggc ggc      1104
Asp Ser Thr Asp Trp Pro Arg Val Thr Ala Pro Thr Tyr Asp Gly Gly
        355                 360                 365
```

-continued

```
ctt ggg ttt aac tac aag tgg aac atg ggc tgg atg aac gac atg ctg      1152
Leu Gly Phe Asn Tyr Lys Trp Asn Met Gly Trp Met Asn Asp Met Leu
    370                 375                 380 aag tat atg gaa acg ccg ccg cat gag cgg aaa tac gcc cat aac caa      1200
Lys Tyr Met Glu Thr Pro Pro His Glu Arg Lys Tyr Ala His Asn Gln
385                 390                 395                 400 gtc agt ttt tcc ctc ctt tat gcg tat tcg gaa aat ttc att ttg cca      1248
Val Ser Phe Ser Leu Leu Tyr Ala Tyr Ser Glu Asn Phe Ile Leu Pro
                405                 410                 415 ttt tcc cat gat gaa gtt gtg cat ggc aaa aaa tcg ctg ctc aat aaa      1296
Phe Ser His Asp Glu Val Val His Gly Lys Lys Ser Leu Leu Asn Lys
            420                 425                 430 atg cct ggg tcg tac gaa gag aag ttc gcc cag ctg cgc cta ttg tat      1344
Met Pro Gly Ser Tyr Glu Glu Lys Phe Ala Gln Leu Arg Leu Leu Tyr
        435                 440                 445 ggc tac atg atg gcc cac cct ggg aaa aag ctg ctg ttt atg ggc agt      1392
Gly Tyr Met Met Ala His Pro Gly Lys Lys Leu Leu Phe Met Gly Ser
    450                 455                 460 gag ttt gcc cag ttt gat gaa tgg aag ttt gag gga gag ctc gac tgg      1440
Glu Phe Ala Gln Phe Asp Glu Trp Lys Phe Glu Gly Glu Leu Asp Trp
465                 470                 475                 480 gtg ctg ttc gat ttt gac ttg cac cgg aaa atg gac gaa tat gtg aag      1488
Val Leu Phe Asp Phe Asp Leu His Arg Lys Met Asp Glu Tyr Val Lys
                485                 490                 495 caa ctg atc gcc tgc tat aaa cgg tat aag ccg ttt tac gag ctt gat      1536
Gln Leu Ile Ala Cys Tyr Lys Arg Tyr Lys Pro Phe Tyr Glu Leu Asp
            500                 505                 510 cat gat ccg agg ggg ttt gaa tgg att gac gtt cat aat gcc gaa caa      1584
His Asp Pro Arg Gly Phe Glu Trp Ile Asp Val His Asn Ala Glu Gln
        515                 520                 525 agc att ttc tcg ttc gtc cgc cgc ggg aaa aaa gac ggc gat cta ttg      1632
Ser Ile Phe Ser Phe Val Arg Arg Gly Lys Lys Asp Gly Asp Leu Leu
    530                 535                 540 gta att gtt tgc aat ttc aca aat cag gcg tat gac gat tac aaa gtc      1680
Val Ile Val Cys Asn Phe Thr Asn Gln Ala Tyr Asp Asp Tyr Lys Val
545                 550                 555                 560 ggc gtg ccg ctt ttg gcg ccg tac cgc gaa gtg ctg aac agc gat gca      1728
Gly Val Pro Leu Leu Ala Pro Tyr Arg Glu Val Leu Asn Ser Asp Ala
                565                 570                 575 gcg gag ttt ggc gga tca ggg cat gtc aat tcg aag cgg ctt tcc gct      1776
Ala Glu Phe Gly Gly Ser Gly His Val Asn Ser Lys Arg Leu Ser Ala
            580                 585                 590 ttc cat gag ccg ttt cat gga aaa ccg tgc cat gtg cgc atg acg att      1824
Phe His Glu Pro Phe His Gly Lys Pro Cys His Val Arg Met Thr Ile
        595                 600                 605 ccg ccg ttt ggc att tcc att ttg cgg cca gtg caa aaa cga ggg gag      1872
Pro Pro Phe Gly Ile Ser Ile Leu Arg Pro Val Gln Lys Arg Gly Glu
    610                 615                 620 aga aag cag aat gaa gaa gac gtg cat cgc cat gtt att ggc cgg cgg      1920
Arg Lys Gln Asn Glu Glu Asp Val His Arg His Val Ile Gly Arg Arg
625                 630                 635                 640 cca agg aag ccg gct tcg ctc gct gac gaa aaa cat cgc gaa acc ggc      1968
Pro Arg Lys Pro Ala Ser Leu Ala Asp Glu Lys His Arg Glu Thr Gly
                645                 650                 655 cgt gcc gtt tgg ggg gaa gta ccg gat cat tga                          2001
Arg Ala Val Trp Gly Glu Val Pro Asp His
            660                 665

<210> SEQ ID NO 12
<211> LENGTH: 666
```

```
<212> TYPE: PRT
<213> ORGANISM: Bacillus thermocatenulatus IFO15316

<400> SEQUENCE: 12

Met Ile Ala Ala Asn Pro Thr Asp Leu Glu Val Tyr Leu Phe His Glu
1               5                   10                  15

Gly Arg Leu Tyr Gln Ser Tyr Glu Leu Phe Gly Ala His Val Ile Arg
            20                  25                  30

Asp Gly Gly Ala Ile Gly Thr Arg Phe Cys Val Trp Ala Pro His Ala
        35                  40                  45

Arg Glu Val Arg Leu Val Gly Ser Phe Asn Asp Trp Asn Gly Ala Asn
    50                  55                  60

Ser Pro Leu Thr Lys Val Asn Asp Glu Gly Val Trp Thr Ile Val Val
65                  70                  75                  80

Pro Glu Asn Leu Glu Gly His Leu Tyr Lys Tyr Glu Ile Ile Thr Pro
                85                  90                  95

Asp Gly Arg Val Leu Leu Lys Ala Asp Pro Tyr Ala Phe Cys Ser Glu
            100                 105                 110

Leu Arg Pro His Thr Ala Ser Ile Val Tyr Asp Leu Lys Gly Tyr Glu
        115                 120                 125

Trp Asn Asp Ser Ser Trp Gln Arg Lys Lys Arg Lys Arg Ile Tyr
    130                 135                 140

Asp Gln Pro Met Val Ile Tyr Glu Leu His Phe Gly Ser Trp Lys Lys
145                 150                 155                 160

Lys Pro Asp Gly Arg Phe Tyr Thr Tyr Arg Glu Met Ala Asp Glu Leu
                165                 170                 175

Ile Pro Tyr Val Leu Glu Arg Gly Phe Thr His Ile Glu Leu Leu Pro
            180                 185                 190

Leu Val Glu His Pro Leu Asp Arg Ser Trp Gly Tyr Gln Gly Thr Gly
        195                 200                 205

Tyr Tyr Ser Val Thr Ser Arg Tyr Gly Thr Pro His Asp Phe Met Tyr
    210                 215                 220

Phe Val Asp Arg Cys His Gln Ala Arg Leu Gly Val Ile Ile Asp Trp
225                 230                 235                 240

Val Pro Gly His Phe Cys Lys Asp Ala His Gly Leu Tyr Met Phe Asp
                245                 250                 255

Gly Ala Pro Thr Tyr Glu Tyr Ala Asn Glu Lys Asp Arg Glu Asn Tyr
            260                 265                 270

Val Trp Gly Thr Ala Asn Phe Asp Leu Gly Lys Pro Glu Val Arg Ser
        275                 280                 285

Phe Leu Ile Ser Asn Ala Leu Phe Trp Leu Glu Tyr Tyr His Val Asp
    290                 295                 300

Gly Phe Arg Val Asp Ala Val Ala Asn Met Leu Tyr Trp Pro Asn Asn
305                 310                 315                 320

Asp Arg Leu Tyr Glu Asn Pro Tyr Ala Val Glu Phe Leu Arg Gln Leu
                325                 330                 335

Asn Glu Ala Val Phe Ala Tyr Asp Pro Asn Val Leu Met Ile Ala Glu
            340                 345                 350

Asp Ser Thr Asp Trp Pro Arg Val Thr Ala Pro Thr Tyr Asp Gly Gly
        355                 360                 365

Leu Gly Phe Asn Tyr Lys Trp Asn Met Gly Trp Met Asn Asp Met Leu
    370                 375                 380

Lys Tyr Met Glu Thr Pro Pro His Glu Arg Lys Tyr Ala His Asn Gln
385                 390                 395                 400
```

```
Val Ser Phe Ser Leu Leu Tyr Ala Tyr Ser Glu Asn Phe Ile Leu Pro
            405                 410                 415

Phe Ser His Asp Glu Val Val His Gly Lys Lys Ser Leu Leu Asn Lys
            420                 425                 430

Met Pro Gly Ser Tyr Glu Glu Lys Phe Ala Gln Leu Arg Leu Leu Tyr
            435                 440                 445

Gly Tyr Met Met Ala His Pro Gly Lys Lys Leu Leu Phe Met Gly Ser
            450                 455                 460

Glu Phe Ala Gln Phe Asp Glu Trp Lys Phe Glu Gly Glu Leu Asp Trp
465                 470                 475                 480

Val Leu Phe Asp Phe Asp Leu His Arg Lys Met Asp Glu Tyr Val Lys
                485                 490                 495

Gln Leu Ile Ala Cys Tyr Lys Arg Tyr Lys Pro Phe Tyr Glu Leu Asp
                500                 505                 510

His Asp Pro Arg Gly Phe Glu Trp Ile Asp Val His Asn Ala Glu Gln
            515                 520                 525

Ser Ile Phe Ser Phe Val Arg Arg Gly Lys Lys Asp Gly Asp Leu Leu
            530                 535                 540

Val Ile Val Cys Asn Phe Thr Asn Gln Ala Tyr Asp Asp Tyr Lys Val
545                 550                 555                 560

Gly Val Pro Leu Leu Ala Pro Tyr Arg Glu Val Leu Asn Ser Asp Ala
                565                 570                 575

Ala Glu Phe Gly Gly Ser Gly His Val Asn Ser Lys Arg Leu Ser Ala
            580                 585                 590

Phe His Glu Pro Phe His Gly Lys Pro Cys His Val Arg Met Thr Ile
            595                 600                 605

Pro Pro Phe Gly Ile Ser Ile Leu Arg Pro Val Gln Lys Arg Gly Glu
            610                 615                 620

Arg Lys Gln Asn Glu Glu Asp Val His Arg His Val Ile Gly Arg Arg
625                 630                 635                 640

Pro Arg Lys Pro Ala Ser Leu Ala Asp Glu Lys His Arg Glu Thr Gly
                645                 650                 655

Arg Ala Val Trp Gly Glu Val Pro Asp His
            660                 665

<210> SEQ ID NO 13
<211> LENGTH: 2001
<212> TYPE: DNA
<213> ORGANISM: Bacillus caldolyticus IFO15313
<220> FEATURE:
<221> NAME/KEY: CDS
<222> LOCATION: (1)..(2001)

<400> SEQUENCE: 13 ttg att gcg gcg aat ccg aca gat tta gaa gtg tat ttg ttt cat gaa      48
Met Ile Ala Ala Asn Pro Thr Asp Leu Glu Val Tyr Leu Phe His Glu
1               5                   10                  15 ggc cgt ttg tat caa agt tat gag ttg ttc ggc gct cat gtc atc cgc      96
Gly Arg Leu Tyr Gln Ser Tyr Glu Leu Phe Gly Ala His Val Ile Arg
            20                  25                  30 gac ggc gga gcg gtc ggc act cgc ttt tgc gtg tgg gcg ccc cat gcg     144
Asp Gly Gly Ala Val Gly Thr Arg Phe Cys Val Trp Ala Pro His Ala
        35                  40                  45 cgg gaa gtc cgt ctt gtc ggc agt ttc aac gat tgg aat ggg gcg aat     192
Arg Glu Val Arg Leu Val Gly Ser Phe Asn Asp Trp Asn Gly Ala Asn
    50                  55                  60
```

-continued

| | | |
|---|---|---|
| tcc ccc ctg acg aag gtg aac gac gaa ggg gta tgg acg atc gtt gtt<br>Ser Pro Leu Thr Lys Val Asn Asp Glu Gly Val Trp Thr Ile Val Val<br>65                        70                     75                   80 | 240 |
| cca gaa aac ttg gaa ggg cat ctc tat aaa tat gag atc atc aca ccg<br>Pro Glu Asn Leu Glu Gly His Leu Tyr Lys Tyr Glu Ile Ile Thr Pro<br>                   85                    90                   95 | 288 |
| gat ggc cgt gtt ctg ttg aaa gcc gac ccg tac gcc ttt tac tcc gaa<br>Asp Gly Arg Val Leu Leu Lys Ala Asp Pro Tyr Ala Phe Tyr Ser Glu<br>                100                  105                110 | 336 |
| ttg cgc cct cat acc gcc tcg att gtc tac gat ttg aaa gga tac cag<br>Leu Arg Pro His Thr Ala Ser Ile Val Tyr Asp Leu Lys Gly Tyr Gln<br>       115                  120                125 | 384 |
| tgg aat gat tca tct tgg cag cgg aag aaa cgg cga aag cgg att tat<br>Trp Asn Asp Ser Ser Trp Gln Arg Lys Lys Arg Arg Lys Arg Ile Tyr<br>130                       135                   140 | 432 |
| gac caa ccg atg gtc att tat gaa ctt cat ttc ggt tcg tgg aaa aag<br>Asp Gln Pro Met Val Ile Tyr Glu Leu His Phe Gly Ser Trp Lys Lys<br>145                       150                   155                160 | 480 |
| aaa ccg gac ggc cgc ttt tat acg tac cgt gag atg gcc gac gaa ctc<br>Lys Pro Asp Gly Arg Phe Tyr Thr Tyr Arg Glu Met Ala Asp Glu Leu<br>                165                  170                175 | 528 |
| att ccg tac gtg ctg gag cgc gga ttt acg cac att gag ctg ctt ccg<br>Ile Pro Tyr Val Leu Glu Arg Gly Phe Thr His Ile Glu Leu Leu Pro<br>               180                  185                190 | 576 |
| ctt gtc gag cat ccg ctc gat cgt tcg tgg gga tat caa ggg acc ggc<br>Leu Val Glu His Pro Leu Asp Arg Ser Trp Gly Tyr Gln Gly Thr Gly<br>       195                  200                205 | 624 |
| tat tat tcg gtg aca agc cgc tat ggc acg ccg cac gat ttc atg tat<br>Tyr Tyr Ser Val Thr Ser Arg Tyr Gly Thr Pro His Asp Phe Met Tyr<br>210                       215                   220 | 672 |
| ttc gtc gac cgc tgc cat caa gcg ggg ctt ggc gtc atc atc gac tgg<br>Phe Val Asp Arg Cys His Gln Ala Gly Leu Gly Val Ile Ile Asp Trp<br>225                       230                   235                240 | 720 |
| gtg ccg ggg cat ttt tgc aag gac gcc cac ggg ctg tac atg ttt gac<br>Val Pro Gly His Phe Cys Lys Asp Ala His Gly Leu Tyr Met Phe Asp<br>               245                  250                255 | 768 |
| ggc gca ccg acg tat gaa tac gcg aat gaa aaa gac cga gaa aat tac<br>Gly Ala Pro Thr Tyr Glu Tyr Ala Asn Glu Lys Asp Arg Glu Asn Tyr<br>       260                  265                270 | 816 |
| gtc tgg ggg acg gcg aat ttt gac ttg ggc aag ccg gaa gtg cgc agt<br>Val Trp Gly Thr Ala Asn Phe Asp Leu Gly Lys Pro Glu Val Arg Ser<br>275                       280                   285 | 864 |
| ttt ctg atc tcc aat gcg ttg ttt tgg ctg gag tat tac cat gtg gac<br>Phe Leu Ile Ser Asn Ala Leu Phe Trp Leu Glu Tyr Tyr His Val Asp<br>290                       295                   300 | 912 |
| ggg ttt cgc gtc gat gcg gtc gcc aat atg ctt tat tgg ccg aac aat<br>Gly Phe Arg Val Asp Ala Val Ala Asn Met Leu Tyr Trp Pro Asn Asn<br>305                       310                   315                320 | 960 |
| gac cgg ctc tat gaa aat ccg tat gcg gtc gag ttt ttg cgc cag ttg<br>Asp Arg Leu Tyr Glu Asn Pro Tyr Ala Val Glu Phe Leu Arg Gln Leu<br>               325                  330                335 | 1008 |
| aat gag gcg gtg ttt gcc tat gac ccg aac gtc ttg atg atc gct gaa<br>Asn Glu Ala Val Phe Ala Tyr Asp Pro Asn Val Leu Met Ile Ala Glu<br>             340                  345                350 | 1056 |
| gat tcg acc gac tgg cct cgg gtg acc gcg ccg acg tac gat ggc ggc<br>Asp Ser Thr Asp Trp Pro Arg Val Thr Ala Pro Thr Tyr Asp Gly Gly<br>     355                  360                365 | 1104 |
| ctt ggg ttt aac tac aag tgg aac atg ggc tgg atg aac gac atg ctg<br>Leu Gly Phe Asn Tyr Lys Trp Asn Met Gly Trp Met Asn Asp Met Leu<br>370                       375                   380 | 1152 |

```
aag tat atg gaa acg ccg ccg cat gag cgg aaa tac gcc cat aac caa      1200
Lys Tyr Met Glu Thr Pro Pro His Glu Arg Lys Tyr Ala His Asn Gln
385                 390                 395                 400 gtc agt ttt tcc ctc ctt tat gcg tat tcg gaa aat ttc att ttg cca      1248
Val Ser Phe Ser Leu Leu Tyr Ala Tyr Ser Glu Asn Phe Ile Leu Pro
                405                 410                 415 ttt tcc cat gat gaa gtt gtg cat ggc aaa aaa tcg ctg ctc aat aaa      1296
Phe Ser His Asp Glu Val Val His Gly Lys Lys Ser Leu Leu Asn Lys
                420                 425                 430 atg cct ggg tcg tac gaa gag aag ttc gcc cag ctg cgc cta ttg tat      1344
Met Pro Gly Ser Tyr Glu Glu Lys Phe Ala Gln Leu Arg Leu Leu Tyr
                435                 440                 445 ggc tac atg atg gcc cac cct ggg aaa aag ctg ctg ttt atg ggc agt      1392
Gly Tyr Met Met Ala His Pro Gly Lys Lys Leu Leu Phe Met Gly Ser
450                 455                 460 gag ttt gcc cag ttt gat gaa tgg aag ttt gag gga gag ctc gac tgg      1440
Glu Phe Ala Gln Phe Asp Glu Trp Lys Phe Glu Gly Glu Leu Asp Trp
465                 470                 475                 480 gtg ctg ttc gat ttt gaa ttg cac tgg aaa atg gac gaa tat gtg aag      1488
Val Leu Phe Asp Phe Glu Leu His Trp Lys Met Asp Glu Tyr Val Lys
                485                 490                 495 cag ctg atc gcc tgc tat aaa cgg tat aag ccg ttt tac gag ctt gat      1536
Gln Leu Ile Ala Cys Tyr Lys Arg Tyr Lys Pro Phe Tyr Glu Leu Asp
                500                 505                 510 cat gat ccg agg ggg ttt gaa tgg att gac gtt cat aat gcc gag caa      1584
His Asp Pro Arg Gly Phe Glu Trp Ile Asp Val His Asn Ala Glu Gln
                515                 520                 525 agt att ttc tca ttc atc cgc cgg ggg aaa aaa gaa ggt gat gtg ctg      1632
Ser Ile Phe Ser Phe Ile Arg Arg Gly Lys Lys Glu Gly Asp Val Leu
530                 535                 540 gtc att gtt tgt aat ttc aca aat cag gcg tat gac gat tac aaa gtc      1680
Val Ile Val Cys Asn Phe Thr Asn Gln Ala Tyr Asp Asp Tyr Lys Val
545                 550                 555                 560 ggc gtg ccg ctt ttg gcg ccg tac cgc gaa gtg ctg aac agc gat gca      1728
Gly Val Pro Leu Leu Ala Pro Tyr Arg Glu Val Leu Asn Ser Asp Ala
                565                 570                 575 gcg gag ttt ggc gga tca ggg cat gtc aat tcg aag cgg ctt tcc gct      1776
Ala Glu Phe Gly Gly Ser Gly His Val Asn Ser Lys Arg Leu Ser Ala
                580                 585                 590 ttc cat gag ccg ttt cat gga aaa ccg tac cat gtg cgc atg acg att      1824
Phe His Glu Pro Phe His Gly Lys Pro Tyr His Val Arg Met Thr Ile
                595                 600                 605 ccg ccg ttt ggc att tcc att ttg cgg cca gtg caa aaa cga ggg gag      1872
Pro Pro Phe Gly Ile Ser Ile Leu Arg Pro Val Gln Lys Arg Gly Glu
610                 615                 620 aga aag cag aat gaa gaa gaa gtg cat cgc cat gtt att ggc cgg cgg      1920
Arg Lys Gln Asn Glu Glu Glu Val His Arg His Val Ile Gly Arg Arg
625                 630                 635                 640 gca agg aag ccg gct tcg ctc gct gac gaa aaa cat cgc gaa acc agc      1968
Ala Arg Lys Pro Ala Ser Leu Ala Asp Glu Lys His Arg Glu Thr Ser
                645                 650                 655 cgt gcc gtt tgg ggg gaa gta ccg gat cat tga                          2001
Arg Ala Val Trp Gly Glu Val Pro Asp His
                660                 665

<210> SEQ ID NO 14
<211> LENGTH: 666
<212> TYPE: PRT
<213> ORGANISM: Bacillus caldolyticus IFO15313
```

<400> SEQUENCE: 14

```
Met Ile Ala Ala Asn Pro Thr Asp Leu Glu Val Tyr Leu Phe His Glu
1               5                   10                  15

Gly Arg Leu Tyr Gln Ser Tyr Glu Leu Phe Gly Ala His Val Ile Arg
            20                  25                  30

Asp Gly Gly Ala Val Gly Thr Arg Phe Cys Val Trp Ala Pro His Ala
        35                  40                  45

Arg Glu Val Arg Leu Val Gly Ser Phe Asn Asp Trp Asn Gly Ala Asn
    50                  55                  60

Ser Pro Leu Thr Lys Val Asn Asp Glu Gly Val Trp Thr Ile Val Val
65                  70                  75                  80

Pro Glu Asn Leu Glu Gly His Leu Tyr Lys Tyr Glu Ile Ile Thr Pro
                85                  90                  95

Asp Gly Arg Val Leu Leu Lys Ala Asp Pro Tyr Ala Phe Tyr Ser Glu
            100                 105                 110

Leu Arg Pro His Thr Ala Ser Ile Val Tyr Asp Leu Lys Gly Tyr Gln
        115                 120                 125

Trp Asn Asp Ser Ser Trp Gln Arg Lys Lys Arg Lys Arg Ile Tyr
    130                 135                 140

Asp Gln Pro Met Val Ile Tyr Glu Leu His Phe Gly Ser Trp Lys Lys
145                 150                 155                 160

Lys Pro Asp Gly Arg Phe Tyr Thr Tyr Arg Glu Met Ala Asp Glu Leu
                165                 170                 175

Ile Pro Tyr Val Leu Glu Arg Gly Phe Thr His Ile Glu Leu Leu Pro
            180                 185                 190

Leu Val Glu His Pro Leu Asp Arg Ser Trp Gly Tyr Gln Gly Thr Gly
        195                 200                 205

Tyr Tyr Ser Val Thr Ser Arg Tyr Gly Thr Pro His Asp Phe Met Tyr
    210                 215                 220

Phe Val Asp Arg Cys His Gln Ala Gly Leu Gly Val Ile Ile Asp Trp
225                 230                 235                 240

Val Pro Gly His Phe Cys Lys Asp Ala His Gly Leu Tyr Met Phe Asp
                245                 250                 255

Gly Ala Pro Thr Tyr Glu Tyr Ala Asn Glu Lys Asp Arg Glu Asn Tyr
            260                 265                 270

Val Trp Gly Thr Ala Asn Phe Asp Leu Gly Lys Pro Glu Val Arg Ser
        275                 280                 285

Phe Leu Ile Ser Asn Ala Leu Phe Trp Leu Glu Tyr Tyr His Val Asp
    290                 295                 300

Gly Phe Arg Val Asp Ala Val Ala Asn Met Leu Tyr Trp Pro Asn Asn
305                 310                 315                 320

Asp Arg Leu Tyr Glu Asn Pro Tyr Ala Val Glu Phe Leu Arg Gln Leu
                325                 330                 335

Asn Glu Ala Val Phe Ala Tyr Asp Pro Asn Val Leu Met Ile Ala Glu
            340                 345                 350

Asp Ser Thr Asp Trp Pro Arg Val Thr Ala Pro Thr Tyr Asp Gly Gly
        355                 360                 365

Leu Gly Phe Asn Tyr Lys Trp Asn Met Gly Trp Met Asn Asp Met Leu
    370                 375                 380

Lys Tyr Met Glu Thr Pro Pro His Glu Arg Lys Tyr Ala His Asn Gln
385                 390                 395                 400

Val Ser Phe Ser Leu Leu Tyr Ala Tyr Ser Glu Asn Phe Ile Leu Pro
                405                 410                 415
```

```
Phe Ser His Asp Glu Val Val His Gly Lys Lys Ser Leu Leu Asn Lys
            420                 425                 430

Met Pro Gly Ser Tyr Glu Glu Lys Phe Ala Gln Leu Arg Leu Leu Tyr
            435                 440                 445

Gly Tyr Met Met Ala His Pro Gly Lys Lys Leu Leu Phe Met Gly Ser
            450                 455                 460

Glu Phe Ala Gln Phe Asp Glu Trp Lys Phe Gly Glu Leu Asp Trp
465                 470                 475                 480

Val Leu Phe Asp Phe Glu Leu His Trp Lys Met Asp Glu Tyr Val Lys
                485                 490                 495

Gln Leu Ile Ala Cys Tyr Lys Arg Tyr Lys Pro Phe Tyr Glu Leu Asp
            500                 505                 510

His Asp Pro Arg Gly Phe Glu Trp Ile Asp Val His Asn Ala Glu Gln
            515                 520                 525

Ser Ile Phe Ser Phe Ile Arg Arg Gly Lys Lys Glu Gly Asp Val Leu
            530                 535                 540

Val Ile Val Cys Asn Phe Thr Asn Gln Ala Tyr Asp Asp Tyr Lys Val
545                 550                 555                 560

Gly Val Pro Leu Leu Ala Pro Tyr Arg Glu Val Leu Asn Ser Asp Ala
                565                 570                 575

Ala Glu Phe Gly Gly Ser Gly His Val Asn Ser Lys Arg Leu Ser Ala
            580                 585                 590

Phe His Glu Pro Phe His Gly Lys Pro Tyr His Val Arg Met Thr Ile
            595                 600                 605

Pro Pro Phe Gly Ile Ser Ile Leu Arg Pro Val Gln Lys Arg Gly Glu
            610                 615                 620

Arg Lys Gln Asn Glu Glu Val His Arg His Val Ile Gly Arg Arg
625                 630                 635                 640

Ala Arg Lys Pro Ala Ser Leu Ala Asp Glu Lys His Arg Glu Thr Ser
                645                 650                 655

Arg Ala Val Trp Gly Glu Val Pro Asp His
            660                 665

<210> SEQ ID NO 15
<211> LENGTH: 2301
<212> TYPE: DNA
<213> ORGANISM: Thermosynechococcus elongatus BP-1
<220> FEATURE:
<221> NAME/KEY: CDS
<222> LOCATION: (1)..(2301)

<400> SEQUENCE: 15 atg acc gtt tcg cct gag cag att gac cgc att gtt tcc aac cag cac      48
Met Thr Val Ser Pro Glu Gln Ile Asp Arg Ile Val Ser Asn Gln His
1               5                   10                  15 cac gat ccc ttt gaa att tta ggg tgt cat cag att cag caa aat ggc      96
His Asp Pro Phe Glu Ile Leu Gly Cys His Gln Ile Gln Gln Asn Gly
                20                  25                  30 caa tcc gtt tgg gcg gta cgt gcc tac tta ccc aat gcc gag cgg gtg     144
Gln Ser Val Trp Ala Val Arg Ala Tyr Leu Pro Asn Ala Glu Arg Val
            35                  40                  45 agt gtc ctc tgt ccg gag cag cgg caa gaa tat cca atg aca ccg gtg     192
Ser Val Leu Cys Pro Glu Gln Arg Gln Glu Tyr Pro Met Thr Pro Val
        50                  55                  60 cac cac cct cac ttt ttt gag tgc cac att ccc gta gcg gaa ctc aat     240
His His Pro His Phe Phe Glu Cys His Ile Pro Val Ala Glu Leu Asn
65                  70                  75                  80
```

-continued

```
aac tat caa ctg aaa atc tac gaa aat ggc cac gag cgg gtt atc tat    288
Asn Tyr Gln Leu Lys Ile Tyr Glu Asn Gly His Glu Arg Val Ile Tyr
             85                  90                  95 gac cct tat gcc ttt cgc tcc ccc aag ttg acc gac ttt gat att cac    336
Asp Pro Tyr Ala Phe Arg Ser Pro Lys Leu Thr Asp Phe Asp Ile His
        100                 105                 110 ctt ttt gcc gag ggc aat cat cac cgc atc tac gaa aaa ctg ggg gct    384
Leu Phe Ala Glu Gly Asn His His Arg Ile Tyr Glu Lys Leu Gly Ala
            115                 120                 125 cat ctg ctg aca gtg gat ggg gta gag ggg gtc tat ttt gcc gtc tgg    432
His Leu Leu Thr Val Asp Gly Val Glu Gly Val Tyr Phe Ala Val Trp
    130                 135                 140 gca ccc aat gcc cgc aat gtt tct gtc att ggt gac ttt aac cac tgg    480
Ala Pro Asn Ala Arg Asn Val Ser Val Ile Gly Asp Phe Asn His Trp
145                 150                 155                 160 gac ggc cgc aaa cat caa atg gca cga cgg ggc aat ggc atc tgg gaa    528
Asp Gly Arg Lys His Gln Met Ala Arg Arg Gly Asn Gly Ile Trp Glu
                165                 170                 175 ctg ttt att ccc ggc ttg agc gtc ggc gag cgc tat aag tac gaa atc    576
Leu Phe Ile Pro Gly Leu Ser Val Gly Glu Arg Tyr Lys Tyr Glu Ile
            180                 185                 190 aag aac caa gag ggc cac atc tac gaa aaa tca gat ccc tac ggc ttc    624
Lys Asn Gln Glu Gly His Ile Tyr Glu Lys Ser Asp Pro Tyr Gly Phe
        195                 200                 205 tac caa gaa ccg cgt ccc aag act gct tcc att gtc acc gac ctc aat    672
Tyr Gln Glu Pro Arg Pro Lys Thr Ala Ser Ile Val Thr Asp Leu Asn
    210                 215                 220 agc tac gaa tgg ggg gac agc gac tgg cta gaa aaa cgg cgc cac acc    720
Ser Tyr Glu Trp Gly Asp Ser Asp Trp Leu Glu Lys Arg Arg His Thr
225                 230                 235                 240 gac ccc ctc aac caa ccg att tct gtc tat gag gtg cac cta gga tct    768
Asp Pro Leu Asn Gln Pro Ile Ser Val Tyr Glu Val His Leu Gly Ser
                245                 250                 255 tgg ctc cat gcc tcg atg gag gat ccc ccc att ggt gcc gat ggc caa    816
Trp Leu His Ala Ser Met Glu Asp Pro Pro Ile Gly Ala Asp Gly Gln
            260                 265                 270 ccc caa gaa ccc gta cag gcg gca gaa ctc aag ccc tgg gca cgc ttc    864
Pro Gln Glu Pro Val Gln Ala Ala Glu Leu Lys Pro Trp Ala Arg Phe
        275                 280                 285 ctg acc tat cgt gaa ttg gca gcc aaa ctc att ccc tac gtc aag gaa    912
Leu Thr Tyr Arg Glu Leu Ala Ala Lys Leu Ile Pro Tyr Val Lys Glu
    290                 295                 300 ttg ggc tac acc cac att gaa ctt ttg cct gtt gct gag cat ccc ttc    960
Leu Gly Tyr Thr His Ile Glu Leu Leu Pro Val Ala Glu His Pro Phe
305                 310                 315                 320 gat ggc tct tgg ggc tat caa gtg act ggc tac tat gcc ccc aca tcc   1008
Asp Gly Ser Trp Gly Tyr Gln Val Thr Gly Tyr Tyr Ala Pro Thr Ser
                325                 330                 335 cgc tat ggc agt ccc cac gac ttt atg tat ttt gtg gat cag tgc cac   1056
Arg Tyr Gly Ser Pro His Asp Phe Met Tyr Phe Val Asp Gln Cys His
            340                 345                 350 caa aac ggc att ggc gtc att gtc gat tgg gta ccg ggg cac ttt ccc   1104
Gln Asn Gly Ile Gly Val Ile Val Asp Trp Val Pro Gly His Phe Pro
        355                 360                 365 aag gac ggc cat ggg ctg gcg ttc ttt gat ggc acc cac ctc tac gaa   1152
Lys Asp Gly His Gly Leu Ala Phe Phe Asp Gly Thr His Leu Tyr Glu
    370                 375                 380 cac gcg gat ccc cgc aag ggt gaa cat aag gaa tgg ggc acc ctt gtc   1200
His Ala Asp Pro Arg Lys Gly Glu His Lys Glu Trp Gly Thr Leu Val
```

-continued

```
            385                 390                 395                 400
ttt aac tat ggt cgc cac gaa gtg cgc aat ttt ctc gtc gcc aat gcc      1248
Phe Asn Tyr Gly Arg His Glu Val Arg Asn Phe Leu Val Ala Asn Ala
                    405                 410                 415 ctg ttt tgg ttt gac aag tac cac att gac ggt att cgc gtg gat gcc      1296
Leu Phe Trp Phe Asp Lys Tyr His Ile Asp Gly Ile Arg Val Asp Ala
                420                 425                 430 gtc gcc tca atg ctc tat ctc gac tat ggc cgc aaa gag gga gag tgg      1344
Val Ala Ser Met Leu Tyr Leu Asp Tyr Gly Arg Lys Glu Gly Glu Trp
            435                 440                 445 ata ccc aat gaa tac ggt gga cgg gag aat tta gag gcg gcc aac ttc      1392
Ile Pro Asn Glu Tyr Gly Gly Arg Glu Asn Leu Glu Ala Ala Asn Phe
        450                 455                 460 ctg cgc caa gtc aac cat gtt atc ttt agc tac ttt ccg ggg att ctc      1440
Leu Arg Gln Val Asn His Val Ile Phe Ser Tyr Phe Pro Gly Ile Leu
    465                 470                 475                 480 tcg atc gcc gag gag tca acc gcc tgg ccg atg gtc tcc tgg ccg acc      1488
Ser Ile Ala Glu Glu Ser Thr Ala Trp Pro Met Val Ser Trp Pro Thr
                    485                 490                 495 tac atg ggg gga ttg ggc ttt aac ctg aag tgg aac atg ggt tgg atg      1536
Tyr Met Gly Gly Leu Gly Phe Asn Leu Lys Trp Asn Met Gly Trp Met
                500                 505                 510 cac gat atg ctt gac tac ttc agc atg gat ccg tgg ttc cgc cag ttc      1584
His Asp Met Leu Asp Tyr Phe Ser Met Asp Pro Trp Phe Arg Gln Phe
            515                 520                 525 cat cac aac aat gtc acc ttc agt atg tgg tac cac cac agc gag aac      1632
His His Asn Asn Val Thr Phe Ser Met Trp Tyr His His Ser Glu Asn
        530                 535                 540 ttc atg ctg gca ctt tcc cac gat gag gtg gtt cac ggc aag agt cac      1680
Phe Met Leu Ala Leu Ser His Asp Glu Val Val His Gly Lys Ser His
545                 550                 555                 560 atc att ggc aaa atg ccg ggc gat cgc tgg caa aaa ttt gcg aac ctg      1728
Ile Ile Gly Lys Met Pro Gly Asp Arg Trp Gln Lys Phe Ala Asn Leu
                    565                 570                 575 cgc tgt tta ttt gcc tat atg ttc acc cac ccc ggt aag aaa aca atg      1776
Arg Cys Leu Phe Ala Tyr Met Phe Thr His Pro Gly Lys Lys Thr Met
                580                 585                 590 ttc atg ggc atg gag ttt gcc caa tgg agc gag tgg aat gtc tgg agc      1824
Phe Met Gly Met Glu Phe Ala Gln Trp Ser Glu Trp Asn Val Trp Ser
            595                 600                 605 gat cta gag tgg cac ctg ctg caa tac gaa ccc cac cag caa atc aaa      1872
Asp Leu Glu Trp His Leu Leu Gln Tyr Glu Pro His Gln Gln Ile Lys
        610                 615                 620 cgc ttc ttt ggg gat ctg aat cac ctc tac cgt tcc caa ccc gca ctc      1920
Arg Phe Phe Gly Asp Leu Asn His Leu Tyr Arg Ser Gln Pro Ala Leu
625                 630                 635                 640 tat agc caa gat ttc aaa cag gag ggc ttt gag tgg att gac tgt agc      1968
Tyr Ser Gln Asp Phe Lys Gln Glu Gly Phe Glu Trp Ile Asp Cys Ser
                    645                 650                 655 gat aac cgc cac agc gtt gtg tcc ttt atc cgc tgg gac aag gac tac      2016
Asp Asn Arg His Ser Val Val Ser Phe Ile Arg Trp Asp Lys Asp Tyr
                660                 665                 670 caa gat ttt gta gtt gtc gtc tgt aac ttt aca cca cag ccc cat agc      2064
Gln Asp Phe Val Val Val Val Cys Asn Phe Thr Pro Gln Pro His Ser
            675                 680                 685 cac tac cgt atc ggg gtg cct gag cat ggc ttc tat agg gaa ctg ttt      2112
His Tyr Arg Ile Gly Val Pro Glu His Gly Phe Tyr Arg Glu Leu Phe
        690                 695                 700 aac agt gat gcc cgc gag tac ggc ggc agc aat atg ggc aac tta ggc      2160
```

-continued

```

Asn Ser Asp Ala Arg Glu Tyr Gly Gly Ser Asn Met Gly Asn Leu Gly
705                 710                 715                 720 ggc aag tgg gca gat gag tgg ccc tat cac cag cgt cgc tat tcc ctt      2208
Gly Lys Trp Ala Asp Glu Trp Pro Tyr His Gln Arg Arg Tyr Ser Leu
                725                 730                 735 gat ctg tgc tta ccc ccc ttg gca gtg ctc att ttg aaa ctg gat cgg      2256
Asp Leu Cys Leu Pro Pro Leu Ala Val Leu Ile Leu Lys Leu Asp Arg
            740                 745                 750 gag aaa aca gtg gca gag cgg gca cgc tat aac ctt cag tcc taa          2301
Glu Lys Thr Val Ala Glu Arg Ala Arg Tyr Asn Leu Gln Ser
        755                 760                 765
```

<210> SEQ ID NO 16
<211> LENGTH: 766
<212> TYPE: PRT
<213> ORGANISM: Thermosynechococcus elongatus BP-1

<400> SEQUENCE: 16

```
Met Thr Val Ser Pro Glu Gln Ile Asp Arg Ile Val Ser Asn Gln His
1               5                   10                  15

His Asp Pro Phe Glu Ile Leu Gly Cys His Gln Ile Gln Gln Asn Gly
                20                  25                  30

Gln Ser Val Trp Ala Val Arg Ala Tyr Leu Pro Asn Ala Glu Arg Val
            35                  40                  45

Ser Val Leu Cys Pro Glu Gln Arg Gln Glu Tyr Pro Met Thr Pro Val
        50                  55                  60

His His Pro His Phe Phe Glu Cys His Ile Pro Val Ala Glu Leu Asn
65                  70                  75                  80

Asn Tyr Gln Leu Lys Ile Tyr Glu Asn Gly His Glu Arg Val Ile Tyr
                85                  90                  95

Asp Pro Tyr Ala Phe Arg Ser Pro Lys Leu Thr Asp Phe Asp Ile His
            100                 105                 110

Leu Phe Ala Glu Gly Asn His His Arg Ile Tyr Glu Lys Leu Gly Ala
        115                 120                 125

His Leu Leu Thr Val Asp Gly Val Glu Gly Val Tyr Phe Ala Val Trp
130                 135                 140

Ala Pro Asn Ala Arg Asn Val Ser Val Ile Gly Asp Phe Asn His Trp
145                 150                 155                 160

Asp Gly Arg Lys His Gln Met Ala Arg Arg Gly Asn Gly Ile Trp Glu
                165                 170                 175

Leu Phe Ile Pro Gly Leu Ser Val Gly Glu Arg Tyr Lys Tyr Glu Ile
            180                 185                 190

Lys Asn Gln Glu Gly His Ile Tyr Glu Lys Ser Asp Pro Tyr Gly Phe
        195                 200                 205

Tyr Gln Glu Pro Arg Pro Lys Thr Ala Ser Ile Val Thr Asp Leu Asn
    210                 215                 220

Ser Tyr Glu Trp Gly Asp Ser Asp Trp Leu Glu Lys Arg Arg His Thr
225                 230                 235                 240

Asp Pro Leu Asn Gln Pro Ile Ser Val Tyr Glu Val His Leu Gly Ser
                245                 250                 255

Trp Leu His Ala Ser Met Glu Asp Pro Pro Ile Gly Ala Asp Gly Gln
            260                 265                 270

Pro Gln Glu Pro Val Gln Ala Ala Glu Leu Lys Pro Trp Ala Arg Phe
        275                 280                 285

Leu Thr Tyr Arg Glu Leu Ala Ala Lys Leu Ile Pro Tyr Val Lys Glu
    290                 295                 300
```

```
Leu Gly Tyr Thr His Ile Glu Leu Leu Pro Val Ala Glu His Pro Phe
305                 310                 315                 320

Asp Gly Ser Trp Gly Tyr Gln Val Thr Gly Tyr Tyr Ala Pro Thr Ser
                325                 330                 335

Arg Tyr Gly Ser Pro His Asp Phe Met Tyr Phe Val Asp Gln Cys His
            340                 345                 350

Gln Asn Gly Ile Gly Val Ile Val Asp Trp Val Pro Gly His Phe Pro
                355                 360                 365

Lys Asp Gly His Gly Leu Ala Phe Phe Asp Gly Thr His Leu Tyr Glu
370                 375                 380

His Ala Asp Pro Arg Lys Gly Glu His Lys Glu Trp Gly Thr Leu Val
385                 390                 395                 400

Phe Asn Tyr Gly Arg His Glu Val Arg Asn Phe Leu Val Ala Asn Ala
                405                 410                 415

Leu Phe Trp Phe Asp Lys Tyr His Ile Asp Gly Ile Arg Val Asp Ala
                420                 425                 430

Val Ala Ser Met Leu Tyr Leu Asp Tyr Gly Arg Lys Glu Gly Glu Trp
            435                 440                 445

Ile Pro Asn Glu Tyr Gly Gly Arg Glu Asn Leu Glu Ala Ala Asn Phe
450                 455                 460

Leu Arg Gln Val Asn His Val Ile Phe Ser Tyr Phe Pro Gly Ile Leu
465                 470                 475                 480

Ser Ile Ala Glu Glu Ser Thr Ala Trp Pro Met Val Ser Trp Pro Thr
                485                 490                 495

Tyr Met Gly Gly Leu Gly Phe Asn Leu Lys Trp Asn Met Gly Trp Met
            500                 505                 510

His Asp Met Leu Asp Tyr Phe Ser Met Asp Pro Trp Phe Arg Gln Phe
                515                 520                 525

His His Asn Asn Val Thr Phe Ser Met Trp Tyr His Ser Glu Asn
                530                 535                 540

Phe Met Leu Ala Leu Ser His Asp Glu Val Val His Gly Lys Ser His
545                 550                 555                 560

Ile Ile Gly Lys Met Pro Gly Asp Arg Trp Gln Lys Phe Ala Asn Leu
                565                 570                 575

Arg Cys Leu Phe Ala Tyr Met Phe Thr His Pro Gly Lys Lys Thr Met
                580                 585                 590

Phe Met Gly Met Glu Phe Ala Gln Trp Ser Glu Trp Asn Val Trp Ser
                595                 600                 605

Asp Leu Glu Trp His Leu Leu Gln Tyr Glu Pro His Gln Gln Ile Lys
            610                 615                 620

Arg Phe Phe Gly Asp Leu Asn His Leu Tyr Arg Ser Gln Pro Ala Leu
625                 630                 635                 640

Tyr Ser Gln Asp Phe Lys Gln Glu Gly Phe Glu Trp Ile Asp Cys Ser
                645                 650                 655

Asp Asn Arg His Ser Val Val Ser Phe Ile Arg Trp Asp Lys Asp Tyr
            660                 665                 670

Gln Asp Phe Val Val Val Val Cys Asn Phe Thr Pro Gln Pro His Ser
            675                 680                 685

His Tyr Arg Ile Gly Val Pro Glu His Gly Phe Tyr Arg Glu Leu Phe
            690                 695                 700

Asn Ser Asp Ala Arg Glu Tyr Gly Gly Ser Asn Met Gly Asn Leu Gly
705                 710                 715                 720
```

-continued

```
Gly Lys Trp Ala Asp Glu Trp Pro Tyr His Gln Arg Arg Tyr Ser Leu
            725                 730                 735

Asp Leu Cys Leu Pro Pro Leu Ala Val Leu Ile Leu Lys Leu Asp Arg
            740                 745                 750

Glu Lys Thr Val Ala Glu Arg Ala Arg Tyr Asn Leu Gln Ser
            755                 760                 765

<210> SEQ ID NO 17
<211> LENGTH: 2187
<212> TYPE: DNA
<213> ORGANISM: Escherichia coli
<220> FEATURE:
<221> NAME/KEY: CDS
<222> LOCATION: (1)..(2187)

<400> SEQUENCE: 17 atg tcc gat cgt atc gat aga gac gtg att aac gcg cta att gca ggc      48
Met Ser Asp Arg Ile Asp Arg Asp Val Ile Asn Ala Leu Ile Ala Gly
1               5                   10                  15 cat ttt gcg gat cct ttt tcc gta ctg gga atg cat aaa acc acc gcg      96
His Phe Ala Asp Pro Phe Ser Val Leu Gly Met His Lys Thr Thr Ala
                20                  25                  30 gga ctg gaa gtc cgt gcc ctt tta ccc gac gct acc gat gtg tgg gtg     144
Gly Leu Glu Val Arg Ala Leu Leu Pro Asp Ala Thr Asp Val Trp Val
            35                  40                  45 att gaa ccg aaa acc ggg cgc aaa ctc gca aaa ctg gag tgt ctc gac     192
Ile Glu Pro Lys Thr Gly Arg Lys Leu Ala Lys Leu Glu Cys Leu Asp
        50                  55                  60 tca cgg gga ttc ttt agc ggc gtc att ccg cga cgt aag aat ttt ttc     240
Ser Arg Gly Phe Phe Ser Gly Val Ile Pro Arg Arg Lys Asn Phe Phe
65                  70                  75                  80 cgc tat cag ttg gct gtt gtc tgg cat ggt cag caa aac ctg att gat     288
Arg Tyr Gln Leu Ala Val Val Trp His Gly Gln Gln Asn Leu Ile Asp
                85                  90                  95 gat cct tac cgt ttt ggt ccg cta atc cag gaa atg gat gcc tgg cta     336
Asp Pro Tyr Arg Phe Gly Pro Leu Ile Gln Glu Met Asp Ala Trp Leu
            100                 105                 110 tta tct gaa ggt act cac ctg cgc ccg tat gaa acc tta ggc gcg cat     384
Leu Ser Glu Gly Thr His Leu Arg Pro Tyr Glu Thr Leu Gly Ala His
        115                 120                 125 gca gat act atg gat ggc gtc aca ggt acg cgt ttc tct gtc tgg gct     432
Ala Asp Thr Met Asp Gly Val Thr Gly Thr Arg Phe Ser Val Trp Ala
    130                 135                 140 cca aac gcc cgt cgg gtc tcg gtg gtt ggg caa ttc aac tac tgg gac     480
Pro Asn Ala Arg Arg Val Ser Val Val Gly Gln Phe Asn Tyr Trp Asp
145                 150                 155                 160 ggt cgc cgt cac ccg atg cgc ctg cgt aaa gag agc ggc atc tgg gaa     528
Gly Arg Arg His Pro Met Arg Leu Arg Lys Glu Ser Gly Ile Trp Glu
                165                 170                 175 ctg ttt atc cct ggg gcg cat aac ggt cag ctc tat aaa tac gag atg     576
Leu Phe Ile Pro Gly Ala His Asn Gly Gln Leu Tyr Lys Tyr Glu Met
            180                 185                 190 att gat gcc aat ggc aac ttg cgt ctg aag tcc gac cct tat gcc ttt     624
Ile Asp Ala Asn Gly Asn Leu Arg Leu Lys Ser Asp Pro Tyr Ala Phe
        195                 200                 205 gaa gcg caa atg cgc ccg gaa acc gcg tct ctt att tgc ggg ctg ccg     672
Glu Ala Gln Met Arg Pro Glu Thr Ala Ser Leu Ile Cys Gly Leu Pro
    210                 215                 220 gaa aag gtt gta cag act gaa gag cgc aaa aaa gcg aat cag ttt gat     720
Glu Lys Val Val Gln Thr Glu Glu Arg Lys Lys Ala Asn Gln Phe Asp
225                 230                 235                 240
```

-continued

```
gcg cca atc tct att tat gaa gtt cac ctg ggt tcc tgg cgt cgc cac    768
Ala Pro Ile Ser Ile Tyr Glu Val His Leu Gly Ser Trp Arg Arg His
            245                 250                 255 acc gac aac aat ttc tgg ttg agc tac cgc gag ctg gcc gat caa ctg    816
Thr Asp Asn Asn Phe Trp Leu Ser Tyr Arg Glu Leu Ala Asp Gln Leu
        260                 265                 270 gtg cct tat gct aaa tgg atg ggc ttt acc cac ctc gaa cta ctg ccc    864
Val Pro Tyr Ala Lys Trp Met Gly Phe Thr His Leu Glu Leu Leu Pro
    275                 280                 285 att aac gag cat ccc ttc gat ggc agt tgg ggt tat cag cca acc ggc    912
Ile Asn Glu His Pro Phe Asp Gly Ser Trp Gly Tyr Gln Pro Thr Gly
290                 295                 300 ctg tat gcg cca acc cgc cgt ttt ggt act cgc gac gac ttc cgt tat    960
Leu Tyr Ala Pro Thr Arg Arg Phe Gly Thr Arg Asp Asp Phe Arg Tyr
305                 310                 315                 320 ttc att gat gcc gca cac gca gct ggt ctg aac gtg att ctc gac tgg   1008
Phe Ile Asp Ala Ala His Ala Ala Gly Leu Asn Val Ile Leu Asp Trp
                325                 330                 335 gtg cca ggc cac ttc ccg act gat gac ttt gcg ctt gcc gaa ttt gat   1056
Val Pro Gly His Phe Pro Thr Asp Asp Phe Ala Leu Ala Glu Phe Asp
            340                 345                 350 ggc acg aac ttg tat gaa cac agc gat ccg cgt gaa ggc tat cat cag   1104
Gly Thr Asn Leu Tyr Glu His Ser Asp Pro Arg Glu Gly Tyr His Gln
        355                 360                 365 gac tgg aac acg ctg atc tac aac tat ggt cgc cgt gaa gtc agt aac   1152
Asp Trp Asn Thr Leu Ile Tyr Asn Tyr Gly Arg Arg Glu Val Ser Asn
    370                 375                 380 ttc ctc gtc ggt aac gcg ctt tac tgg att gaa cgt ttt ggt att gat   1200
Phe Leu Val Gly Asn Ala Leu Tyr Trp Ile Glu Arg Phe Gly Ile Asp
385                 390                 395                 400 gcg ctg cgc gtc gat gcg gtg gcg tca atg att tat cgc gac tac agc   1248
Ala Leu Arg Val Asp Ala Val Ala Ser Met Ile Tyr Arg Asp Tyr Ser
                405                 410                 415 cgt aaa gag ggg gag tgg atc ccg aac gaa ttt ggc ggg cgc gag aat   1296
Arg Lys Glu Gly Glu Trp Ile Pro Asn Glu Phe Gly Gly Arg Glu Asn
            420                 425                 430 ctt gaa gcg att gaa ttc ttg cgt aat acc aac cgt att ctt ggt gag   1344
Leu Glu Ala Ile Glu Phe Leu Arg Asn Thr Asn Arg Ile Leu Gly Glu
        435                 440                 445 cag gtt tcc ggt gcg gtg aca atg gct gag gag tct acc gat ttc cct   1392
Gln Val Ser Gly Ala Val Thr Met Ala Glu Glu Ser Thr Asp Phe Pro
    450                 455                 460 ggc gtt tct cgt ccg cag gat atg ggc ggt ctg ggc ttc tgg tac aag   1440
Gly Val Ser Arg Pro Gln Asp Met Gly Gly Leu Gly Phe Trp Tyr Lys
465                 470                 475                 480 tgg aac ctc ggc tgg atg cat gac acc ctg gac tac atg aag ctc gac   1488
Trp Asn Leu Gly Trp Met His Asp Thr Leu Asp Tyr Met Lys Leu Asp
                485                 490                 495 ccg gtt tat cgt cag tat cat cac gat aaa ctg acc ttc ggg att ctc   1536
Pro Val Tyr Arg Gln Tyr His His Asp Lys Leu Thr Phe Gly Ile Leu
            500                 505                 510 tac aac tac act gaa aac ttc gtc ctg ccg ttg tcg cat gat gaa gtg   1584
Tyr Asn Tyr Thr Glu Asn Phe Val Leu Pro Leu Ser His Asp Glu Val
        515                 520                 525 gtc cac ggt aaa aaa tcg att ctc gac cgc atg ccg ggc gac gca tgg   1632
Val His Gly Lys Lys Ser Ile Leu Asp Arg Met Pro Gly Asp Ala Trp
    530                 535                 540 cag aaa ttc gcg aac ctg cgc gcc tac tat ggc tgg atg tgg gca ttc   1680
Gln Lys Phe Ala Asn Leu Arg Ala Tyr Tyr Gly Trp Met Trp Ala Phe
```

```
                    545                 550                 555                 560
ccg ggc aag aaa cta ctg ttc atg ggt aac gaa ttt gcc cag ggc cgc      1728
Pro Gly Lys Lys Leu Leu Phe Met Gly Asn Glu Phe Ala Gln Gly Arg
                565                 570                 575 gag tgg aac cat gac gcc agc ctc gac tgg cat ctg ttg gaa ggc ggc      1776
Glu Trp Asn His Asp Ala Ser Leu Asp Trp His Leu Leu Glu Gly Gly
            580                 585                 590 gat aac tgg cac cac ggt gtc cag cgt ctg gtg cgc gat ctg aac ctc      1824
Asp Asn Trp His His Gly Val Gln Arg Leu Val Arg Asp Leu Asn Leu
        595                 600                 605 acc tac cgc cac cat aaa gca atg cat gaa ctg gat ttt gac ccg tac      1872
Thr Tyr Arg His His Lys Ala Met His Glu Leu Asp Phe Asp Pro Tyr
    610                 615                 620 ggc ttt gaa tgg ctg gtg gtg gat gac aaa gaa cgc tcg gtg ctg atc      1920
Gly Phe Glu Trp Leu Val Val Asp Asp Lys Glu Arg Ser Val Leu Ile
625                 630                 635                 640 ttt gtg cgt cgc gat aaa gag ggt aac gaa atc atc gtt gcc agt aac      1968
Phe Val Arg Arg Asp Lys Glu Gly Asn Glu Ile Ile Val Ala Ser Asn
                645                 650                 655 ttt acg ccg gta ccg cgt cat gat tat cgc ttc ggc ata aac cag ccg      2016
Phe Thr Pro Val Pro Arg His Asp Tyr Arg Phe Gly Ile Asn Gln Pro
            660                 665                 670 ggc aaa tgg cgt gaa atc ctc aat acc gat tcc atg cac tat cac ggc      2064
Gly Lys Trp Arg Glu Ile Leu Asn Thr Asp Ser Met His Tyr His Gly
        675                 680                 685 agt aat gca ggc aat ggc ggc acg gta cac agc gat gag att gcc agc      2112
Ser Asn Ala Gly Asn Gly Gly Thr Val His Ser Asp Glu Ile Ala Ser
    690                 695                 700 cac ggt cgt cag cat tca cta agc ctg acg cta cca ccg ctg gcc act      2160
His Gly Arg Gln His Ser Leu Ser Leu Thr Leu Pro Pro Leu Ala Thr
705                 710                 715                 720 atc tgg ctg gtt cgg gag gca gaa tga                                  2187
Ile Trp Leu Val Arg Glu Ala Glu
                725

<210> SEQ ID NO 18
<211> LENGTH: 728
<212> TYPE: PRT
<213> ORGANISM: Escherichia coli

<400> SEQUENCE: 18

Met Ser Asp Arg Ile Asp Arg Asp Val Ile Asn Ala Leu Ile Ala Gly
1               5                   10                  15

His Phe Ala Asp Pro Phe Ser Val Leu Gly Met His Lys Thr Thr Ala
            20                  25                  30

Gly Leu Glu Val Arg Ala Leu Leu Pro Asp Ala Thr Asp Val Trp Val
        35                  40                  45

Ile Glu Pro Lys Thr Gly Arg Lys Leu Ala Lys Leu Glu Cys Leu Asp
    50                  55                  60

Ser Arg Gly Phe Phe Ser Gly Val Ile Pro Arg Arg Lys Asn Phe Phe
65                  70                  75                  80

Arg Tyr Gln Leu Ala Val Val Trp His Gly Gln Gln Asn Leu Ile Asp
                85                  90                  95

Asp Pro Tyr Arg Phe Gly Pro Leu Ile Gln Glu Met Asp Ala Trp Leu
            100                 105                 110

Leu Ser Glu Gly Thr His Leu Arg Pro Tyr Glu Thr Leu Gly Ala His
        115                 120                 125

Ala Asp Thr Met Asp Gly Val Thr Gly Thr Arg Phe Ser Val Trp Ala
```

-continued

```
            130                 135                 140
Pro Asn Ala Arg Arg Val Ser Val Gly Gln Phe Asn Tyr Trp Asp
145                 150                 155                 160
Gly Arg Arg His Pro Met Arg Leu Arg Lys Glu Ser Gly Ile Trp Glu
                165                 170                 175
Leu Phe Ile Pro Gly Ala His Asn Gly Gln Leu Tyr Lys Tyr Glu Met
                180                 185                 190
Ile Asp Ala Asn Gly Asn Leu Arg Leu Lys Ser Asp Pro Tyr Ala Phe
                195                 200                 205
Glu Ala Gln Met Arg Pro Glu Thr Ala Ser Leu Ile Cys Gly Leu Pro
210                 215                 220
Glu Lys Val Val Gln Thr Glu Arg Lys Lys Ala Asn Gln Phe Asp
225                 230                 235                 240
Ala Pro Ile Ser Ile Tyr Glu Val His Leu Gly Ser Trp Arg Arg His
                245                 250                 255
Thr Asp Asn Asn Phe Trp Leu Ser Tyr Arg Glu Leu Ala Asp Gln Leu
                260                 265                 270
Val Pro Tyr Ala Lys Trp Met Gly Phe Thr His Leu Glu Leu Leu Pro
                275                 280                 285
Ile Asn Glu His Pro Phe Asp Gly Ser Trp Gly Tyr Gln Pro Thr Gly
                290                 295                 300
Leu Tyr Ala Pro Thr Arg Arg Phe Gly Thr Arg Asp Asp Phe Arg Tyr
305                 310                 315                 320
Phe Ile Asp Ala Ala His Ala Ala Gly Leu Asn Val Ile Leu Asp Trp
                325                 330                 335
Val Pro Gly His Phe Pro Thr Asp Asp Phe Ala Leu Ala Glu Phe Asp
                340                 345                 350
Gly Thr Asn Leu Tyr Glu His Ser Asp Pro Arg Glu Gly Tyr His Gln
                355                 360                 365
Asp Trp Asn Thr Leu Ile Tyr Asn Tyr Gly Arg Arg Glu Val Ser Asn
                370                 375                 380
Phe Leu Val Gly Asn Ala Leu Tyr Trp Ile Glu Arg Phe Gly Ile Asp
385                 390                 395                 400
Ala Leu Arg Val Asp Ala Val Ala Ser Met Ile Tyr Arg Asp Tyr Ser
                405                 410                 415
Arg Lys Glu Gly Glu Trp Ile Pro Asn Glu Phe Gly Gly Arg Glu Asn
                420                 425                 430
Leu Glu Ala Ile Glu Phe Leu Arg Asn Thr Asn Arg Ile Leu Gly Glu
                435                 440                 445
Gln Val Ser Gly Ala Val Thr Met Ala Glu Ser Thr Asp Phe Pro
450                 455                 460
Gly Val Ser Arg Pro Gln Asp Met Gly Gly Leu Gly Phe Trp Tyr Lys
465                 470                 475                 480
Trp Asn Leu Gly Trp Met His Asp Thr Leu Asp Tyr Met Lys Leu Asp
                485                 490                 495
Pro Val Tyr Arg Gln Tyr His Asp Lys Leu Thr Phe Gly Ile Leu
                500                 505                 510
Tyr Asn Tyr Thr Glu Asn Phe Val Leu Pro Leu Ser His Asp Glu Val
                515                 520                 525
Val His Gly Lys Lys Ser Ile Leu Asp Arg Met Pro Gly Asp Ala Trp
                530                 535                 540
Gln Lys Phe Ala Asn Leu Arg Ala Tyr Tyr Gly Trp Met Trp Ala Phe
545                 550                 555                 560
```

```
Pro Gly Lys Lys Leu Leu Phe Met Gly Asn Glu Phe Ala Gln Gly Arg
              565                 570                 575

Glu Trp Asn His Asp Ala Ser Leu Asp Trp His Leu Glu Gly Gly
        580                 585                 590

Asp Asn Trp His His Gly Val Gln Arg Leu Val Arg Asp Leu Asn Leu
            595                 600                 605

Thr Tyr Arg His His Lys Ala Met His Glu Leu Asp Phe Asp Pro Tyr
        610                 615                 620

Gly Phe Glu Trp Leu Val Val Asp Asp Lys Glu Arg Ser Val Leu Ile
625                 630                 635                 640

Phe Val Arg Arg Asp Lys Glu Gly Asn Glu Ile Ile Val Ala Ser Asn
                645                 650                 655

Phe Thr Pro Val Pro Arg His Asp Tyr Arg Phe Gly Ile Asn Gln Pro
            660                 665                 670

Gly Lys Trp Arg Glu Ile Leu Asn Thr Asp Ser Met His Tyr His Gly
        675                 680                 685

Ser Asn Ala Gly Asn Gly Gly Thr Val His Ser Asp Glu Ile Ala Ser
    690                 695                 700

His Gly Arg Gln His Ser Leu Ser Leu Thr Leu Pro Pro Leu Ala Thr
705                 710                 715                 720

Ile Trp Leu Val Arg Glu Ala Glu
                725

<210> SEQ ID NO 19
<211> LENGTH: 1503
<212> TYPE: DNA
<213> ORGANISM: Thermus aquaticus Taq MalQ
<220> FEATURE:
<221> NAME/KEY: CDS
<222> LOCATION: (1)..(1503)

<400> SEQUENCE: 19 atg gag ctt ccc cgc gct ttc ggt ctg ctt ctc cac ccc acg agc ctc      48
Met Glu Leu Pro Arg Ala Phe Gly Leu Leu Leu His Pro Thr Ser Leu
1               5                   10                  15 ccc ggc ccc tac ggc gtc ggc gtc ctg ggc cgg gag gcc cgg gac ttc      96
Pro Gly Pro Tyr Gly Val Gly Val Leu Gly Arg Glu Ala Arg Asp Phe
            20                  25                  30 ctc cgc ttc ctc aag gag gcg ggg ggg cgg tac tgg cag gtc ctc ccc     144
Leu Arg Phe Leu Lys Glu Ala Gly Gly Arg Tyr Trp Gln Val Leu Pro
        35                  40                  45 ttg ggc ccc acg ggc tat ggc gac tcc ccc tac cag tcc ttc agc gcc     192
Leu Gly Pro Thr Gly Tyr Gly Asp Ser Pro Tyr Gln Ser Phe Ser Ala
    50                  55                  60 ttc gcc gga aac ccc tac ctc ata gac ctg agg ccc ctc gcg gaa agg     240
Phe Ala Gly Asn Pro Tyr Leu Ile Asp Leu Arg Pro Leu Ala Glu Arg
65                  70                  75                  80 ggc tac gtg cgc ctg gag gac ccc ggc ttc ccc caa ggc cgg gtg gac     288
Gly Tyr Val Arg Leu Glu Asp Pro Gly Phe Pro Gln Gly Arg Val Asp
                85                  90                  95 tac ggc ctc ctc tac gcc tgg aag tgg ccc gcc ctg aag gag gcc ttc     336
Tyr Gly Leu Leu Tyr Ala Trp Lys Trp Pro Ala Leu Lys Glu Ala Phe
            100                 105                 110 cgg ggc ttc aag gaa aag gcc tcc ccg gag gag cgg gag gcc ttc gcc     384
Arg Gly Phe Lys Glu Lys Ala Ser Pro Glu Glu Arg Glu Ala Phe Ala
        115                 120                 125 gcc ttc cgg gag agg gag gcc tgg tgg ctc gag gac tac gcc ctc ttc     432
Ala Phe Arg Glu Arg Glu Ala Trp Trp Leu Glu Asp Tyr Ala Leu Phe
```

```
          130                 135                 140
atg gcc ctg aag ggg gcg cac ggg ggg ctt ccc tgg aac cgg tgg ccc      480
Met Ala Leu Lys Gly Ala His Gly Gly Leu Pro Trp Asn Arg Trp Pro
145                 150                 155                 160 ctt ccc ctg cgg aag cgg gaa gag aag gcc ctt agg gag gcg aaa agc      528
Leu Pro Leu Arg Lys Arg Glu Glu Lys Ala Leu Arg Glu Ala Lys Ser
                165                 170                 175 gcc ttg gcc gag gag gtg gcc ttc cac gcc ttc acc cag tgg ctc ttc      576
Ala Leu Ala Glu Glu Val Ala Phe His Ala Phe Thr Gln Trp Leu Phe
            180                 185                 190 ttc cgc cag tgg ggg gcc ttg aag gcg gag gcc gag gcg ttg ggc atc      624
Phe Arg Gln Trp Gly Ala Leu Lys Ala Glu Ala Glu Ala Leu Gly Ile
        195                 200                 205 cgg atc atc ggg gac atg ccc atc ttc gtg gcc gag gac tcc gcc gag      672
Arg Ile Ile Gly Asp Met Pro Ile Phe Val Ala Glu Asp Ser Ala Glu
    210                 215                 220 gtc tgg gcc cac ccc gag tgg ttt cac ctg gac gag gag ggc cgc ccc      720
Val Trp Ala His Pro Glu Trp Phe His Leu Asp Glu Glu Gly Arg Pro
225                 230                 235                 240 acg gtg gtg gcg ggg gtg ccc ccc gac tac ttc tcg gag acg ggc cag      768
Thr Val Val Ala Gly Val Pro Pro Asp Tyr Phe Ser Glu Thr Gly Gln
                245                 250                 255 cgc tgg ggt aac ccc ctt tac cgc tgg gac gtt ttg gag cgc gag ggg      816
Arg Trp Gly Asn Pro Leu Tyr Arg Trp Asp Val Leu Glu Arg Glu Gly
            260                 265                 270 ttc tcc ttc tgg atc cgc cgt ctg gag aag gcc ctg gag ctc ttc cac      864
Phe Ser Phe Trp Ile Arg Arg Leu Glu Lys Ala Leu Glu Leu Phe His
        275                 280                 285 ctg gtg cgc ata gac cac ttc cgc ggc ttt gag gcc tac tgg gag atc      912
Leu Val Arg Ile Asp His Phe Arg Gly Phe Glu Ala Tyr Trp Glu Ile
    290                 295                 300 ccc gca agc tgc ccc acg gcg gtg gag ggg cgc tgg gtc aag gcc ccg      960
Pro Ala Ser Cys Pro Thr Ala Val Glu Gly Arg Trp Val Lys Ala Pro
305                 310                 315                 320 ggg gag aag ctc ttc cag aag atc cag gag gtc ttc ggc gag gtc ccc     1008
Gly Glu Lys Leu Phe Gln Lys Ile Gln Glu Val Phe Gly Glu Val Pro
                325                 330                 335 gtc ctc gcc gag gac ctg ggg gtc atc acc ccc gag gtg gag gcc ctg     1056
Val Leu Ala Glu Asp Leu Gly Val Ile Thr Pro Glu Val Glu Ala Leu
            340                 345                 350 cgc gac cgc ttc ggc ctt ccc ggg atg aag gtc ctg cag ttc gcc ttt     1104
Arg Asp Arg Phe Gly Leu Pro Gly Met Lys Val Leu Gln Phe Ala Phe
        355                 360                 365 gac gac ggg atg gaa aac ccc ttc ctc ccc cac aac tac cct gcc cac     1152
Asp Asp Gly Met Glu Asn Pro Phe Leu Pro His Asn Tyr Pro Ala His
    370                 375                 380 ggc cgg gtg gtg gtc tac acc ggc acc cac gac aac gac acc acc ctg     1200
Gly Arg Val Val Val Tyr Thr Gly Thr His Asp Asn Asp Thr Thr Leu
385                 390                 395                 400 ggc tgg tac cgc acg gcc acc ccc cac gag aag gcc ttc atg gcg cgg     1248
Gly Trp Tyr Arg Thr Ala Thr Pro His Glu Lys Ala Phe Met Ala Arg
                405                 410                 415 tac ctg gcg gac tgg ggg atc acc ttc cgg gaa gag gag gag gtg ccc     1296
Tyr Leu Ala Asp Trp Gly Ile Thr Phe Arg Glu Glu Glu Glu Val Pro
            420                 425                 430 tgg gcc ctg atg cac ctg ggg atg aag tcc gtg gcc cgg ctc gcc gtc     1344
Trp Ala Leu Met His Leu Gly Met Lys Ser Val Ala Arg Leu Ala Val
        435                 440                 445 tac ccg gtg cag gac gtc ctg gcc ctg ggc agc gag gcc cgg atg aac     1392
```

-continued

```
Tyr Pro Val Gln Asp Val Leu Ala Leu Gly Ser Glu Ala Arg Met Asn
450                 455                 460
tac ccg gga agg ccc tcg ggg aac tgg gcc tgg cgg ctc ctc ccg ggg    1440
Tyr Pro Gly Arg Pro Ser Gly Asn Trp Ala Trp Arg Leu Leu Pro Gly
465                 470                 475                 480 gag ctt tcc ccg gag cac ggg gcg agg ctt agg gcc atg gcc gag gcc    1488
Glu Leu Ser Pro Glu His Gly Ala Arg Leu Arg Ala Met Ala Glu Ala
                485                 490                 495 acg gaa cgg ctc tag                                                1503
Thr Glu Arg Leu
            500
```

<210> SEQ ID NO 20
<211> LENGTH: 500
<212> TYPE: PRT
<213> ORGANISM: Thermus aquaticus Taq MalQ

<400> SEQUENCE: 20

```
Met Glu Leu Pro Arg Ala Phe Gly Leu Leu His Pro Thr Ser Leu
1               5                   10                  15

Pro Gly Pro Tyr Gly Val Gly Val Leu Gly Arg Glu Ala Arg Asp Phe
                20                  25                  30

Leu Arg Phe Leu Lys Glu Ala Gly Gly Arg Tyr Trp Gln Val Leu Pro
        35                  40                  45

Leu Gly Pro Thr Gly Tyr Gly Asp Ser Pro Tyr Gln Ser Phe Ser Ala
    50                  55                  60

Phe Ala Gly Asn Pro Tyr Leu Ile Asp Leu Arg Pro Leu Ala Glu Arg
65                  70                  75                  80

Gly Tyr Val Arg Leu Glu Asp Pro Gly Phe Pro Gln Gly Arg Val Asp
                85                  90                  95

Tyr Gly Leu Leu Tyr Ala Trp Lys Trp Pro Ala Leu Lys Glu Ala Phe
            100                 105                 110

Arg Gly Phe Lys Glu Lys Ala Ser Pro Glu Glu Arg Glu Ala Phe Ala
        115                 120                 125

Ala Phe Arg Glu Arg Glu Ala Trp Trp Leu Glu Asp Tyr Ala Leu Phe
    130                 135                 140

Met Ala Leu Lys Gly Ala His Gly Gly Leu Pro Trp Asn Arg Trp Pro
145                 150                 155                 160

Leu Pro Leu Arg Lys Arg Glu Glu Lys Ala Leu Arg Glu Ala Lys Ser
                165                 170                 175

Ala Leu Ala Glu Glu Val Ala Phe His Ala Phe Thr Gln Trp Leu Phe
            180                 185                 190

Phe Arg Gln Trp Gly Ala Leu Lys Ala Glu Ala Glu Ala Leu Gly Ile
        195                 200                 205

Arg Ile Ile Gly Asp Met Pro Ile Phe Val Ala Glu Asp Ser Ala Glu
    210                 215                 220

Val Trp Ala His Pro Glu Trp Phe His Leu Asp Glu Glu Gly Arg Pro
225                 230                 235                 240

Thr Val Val Ala Gly Val Pro Pro Asp Tyr Phe Ser Glu Thr Gly Gln
                245                 250                 255

Arg Trp Gly Asn Pro Leu Tyr Arg Trp Asp Val Leu Glu Arg Glu Gly
            260                 265                 270

Phe Ser Phe Trp Ile Arg Arg Leu Glu Lys Ala Leu Glu Leu Phe His
        275                 280                 285

Leu Val Arg Ile Asp His Phe Arg Gly Phe Glu Ala Tyr Trp Glu Ile
    290                 295                 300
```

```
Pro Ala Ser Cys Pro Thr Ala Val Glu Gly Arg Trp Val Lys Ala Pro
305                 310                 315                 320

Gly Glu Lys Leu Phe Gln Lys Ile Gln Glu Val Phe Gly Glu Val Pro
            325                 330                 335

Val Leu Ala Glu Asp Leu Gly Val Ile Thr Pro Glu Val Glu Ala Leu
        340                 345                 350

Arg Asp Arg Phe Gly Leu Pro Gly Met Lys Val Leu Gln Phe Ala Phe
    355                 360                 365

Asp Asp Gly Met Glu Asn Pro Phe Leu Pro His Asn Tyr Pro Ala His
    370                 375                 380

Gly Arg Val Val Val Tyr Thr Gly Thr His Asp Asn Asp Thr Thr Leu
385                 390                 395                 400

Gly Trp Tyr Arg Thr Ala Thr Pro His Glu Lys Ala Phe Met Ala Arg
            405                 410                 415

Tyr Leu Ala Asp Trp Gly Ile Thr Phe Arg Glu Glu Glu Val Pro
        420                 425                 430

Trp Ala Leu Met His Leu Gly Met Lys Ser Val Ala Arg Leu Ala Val
    435                 440                 445

Tyr Pro Val Gln Asp Val Leu Ala Leu Gly Ser Glu Ala Arg Met Asn
    450                 455                 460

Tyr Pro Gly Arg Pro Ser Gly Asn Trp Ala Trp Arg Leu Leu Pro Gly
465                 470                 475                 480

Glu Leu Ser Pro Glu His Gly Ala Arg Leu Arg Ala Met Ala Glu Ala
            485                 490                 495

Thr Glu Arg Leu
            500

<210> SEQ ID NO 21
<211> LENGTH: 30
<212> TYPE: DNA
<213> ORGANISM: artificial sequence
<220> FEATURE:
<223> OTHER INFORMATION: primer ECBEN-NCO

<400> SEQUENCE: 21
gaaccatggc cgatcgtatc gatagagacg                                      30

<210> SEQ ID NO 22
<211> LENGTH: 27
<212> TYPE: DNA
<213> ORGANISM: artificial sequence
<220> FEATURE:
<223> OTHER INFORMATION: primer ECBEC-HIN

<400> SEQUENCE: 22
cccaagcttc attctgcctc ccgaacc                                         27

<210> SEQ ID NO 23
<211> LENGTH: 40
<212> TYPE: DNA
<213> ORGANISM: artificial sequence
<220> FEATURE:
<223> OTHER INFORMATION: primer ROBEN-ECO

<400> SEQUENCE: 23
aatccaacct tcgaattcag ctggctcacg gaagaagaca                           40

<210> SEQ ID NO 24
<211> LENGTH: 40
```

-continued

```
<212> TYPE: DNA
<213> ORGANISM: artificial sequence
<220> FEATURE:
<223> OTHER INFORMATION: primer ROBEC-PST

<400> SEQUENCE: 24
aatcaatcaa tcaactgcag acggttaccc gtgctccggc                              40
```